US009205137B2

(12) United States Patent
Pierzynowski et al.

(10) Patent No.: US 9,205,137 B2
(45) Date of Patent: Dec. 8, 2015

(54) MATURATION OF GASTROINTESTINAL TRACT

(75) Inventors: Stefan Pierzynowski, Trelleborg (SE); Olena Prykhod'ko, Lund (SE); Björn Weström, Ängelholm (SE)

(73) Assignee: ANARA AB, Malmo (SE)

(*) Notice: Subject to any disclaimer, the term of this patent is extended or adjusted under 35 U.S.C. 154(b) by 0 days.

(21) Appl. No.: 13/821,480

(22) PCT Filed: Sep. 8, 2011

(86) PCT No.: PCT/SE2011/051089
§ 371 (c)(1),
(2), (4) Date: Mar. 7, 2013

(87) PCT Pub. No.: WO2012/033459
PCT Pub. Date: Mar. 15, 2012

(65) Prior Publication Data
US 2013/0171121 A1 Jul. 4, 2013

Related U.S. Application Data

(60) Provisional application No. 61/380,740, filed on Sep. 8, 2010, provisional application No. 61/439,090, filed on Feb. 3, 2011.

(30) Foreign Application Priority Data

Sep. 8, 2010 (SE) ........................................ 1050928

(51) Int. Cl.
*A61K 38/54* (2006.01)
*A61K 38/46* (2006.01)
*A61K 38/47* (2006.01)
*A61K 38/48* (2006.01)

(52) U.S. Cl.
CPC ............. *A61K 38/54* (2013.01); *A61K 38/465* (2013.01); *A61K 38/47* (2013.01); *A61K 38/48* (2013.01)

(58) Field of Classification Search
None
See application file for complete search history.

(56) References Cited

U.S. PATENT DOCUMENTS

| 5,569,458 | A | * | 10/1996 | Greenberg | .................... 424/726 |
| 5,902,617 | A | * | 5/1999 | Pabst | ............................... 426/61 |
| 2001/0046493 | A1 | | 11/2001 | Margolin et al. | |
| 2009/0324572 | A1 | | 12/2009 | Fallon | |

FOREIGN PATENT DOCUMENTS

| CA | 2 555 516 | 1/2008 | ............. A61K 38/43 |
| EP | 2 198 880 | 6/2010 | |
| EP | 2198880 A1 | 6/2010 | |
| WO | WO 99/49882 | 10/1999 | ............. A61K 38/19 |
| WO | WO-9949882 A2 | 10/1999 | |
| WO | WO 03/051345 | 6/2003 | ............. A61K 31/00 |

OTHER PUBLICATIONS

Morrison et al. (Mothers and Babies and HIV: What is the Risk of Breastfeeding? Health e-Learning (2002) pp. 1-4.*
Nagin et al. What Are Some Specific Enzymes Present in Breast Milk? (2009) About.com.*
Noerr et al. (Current Controversies in the Understanding of Necrotizing Enterocolitis. Advances in Neonatal Care. (2003): 3(3) 1-2).*
Swanson Health Products. Pancreatin by Twinlab (http://www.swansonvitamins.com/twinlab-pancreatin-500-mg-50-caps).*
Nurse's Handbook (Jones & Bartlett Leaning, 2009 p. 784).*
International Search Report for PCT/SE2011/051089 dated Dec. 15, 2011.
Bin-Nun, A., et al. "Oral probiotics prevent necrotizing enterocolitis in very low birth weight neonates", (2005) *J Pediatr*, 147:192-196.
Lebenthal, E., et al. "Enzyme therapy for pancreatic insufficiency: present status and future needs", (1994) *Pancreas*, 9(1):1-12.
Neu, J. "Gastrointestinal maturation and implications for infant feeding", (2007) *Early Human Development*, 83:767-775.
Wood C.M., et al. "Pancreatic exocrine function and necrotising enterocolitis", (1993) *Early Human Development*, 35:145-149.
Extended European Search Report dated Dec. 20, 2013 issued in PCT Application No. PCT/SE2011051089.

* cited by examiner

*Primary Examiner* — Karen Cochrane Carlson
*Assistant Examiner* — Natalie Moss
(74) *Attorney, Agent, or Firm* — Harness, Dickey & Pierce, P.L.C.

(57) ABSTRACT

The present invention provides a method to induce maturation of an immature GI-tract, such as intestine, e.g. small intestine, the method comprising the steps of administering a mixture of enzymes to the immature GI-tract, said enzymes having a pancreatic activity or action, and/or pancreatic like activity or action, and analyzing the maturation process of the GI-tract to monitor said maturation process. Provided herein are also uses and kits to provide for GI-tract maturation.

6 Claims, 24 Drawing Sheets

MATURATION OF GASTROINTESTINAL TRACT

CROSS-REFERENCE TO RELATED APPLICATIONS

This application is the national phase application under 35 U.S.C. §371 of PCT International Application No. PCT/SE2011/051089 which has an International filing date of 8 Sep. 2011, and which claims the benefit under 35 U.S.C. §119 to US Application No. 61/380,740, filed 8 Sep. 2010, and 61/439,090, filed 3 Feb. 2011. This application also claims foreign priority under 35 U.S.C. §119 to Sweden Application No. 1050928-9, filed on 8 Sep. 2010. The contents of each application recited above are incorporated herein by reference in their entirety.

TECHNICAL FIELD

The present invention relates to the field of gastrointestinal function, particularly in a newborn. Particularly, the present invention relates to the maturation process of the gastrointestinal tract, such as the small intestine, induced by administration of a mixture of enzymes to a mammal such as a newborn.

BACKGROUND OF THE INVENTION

The gastrointestinal (GI) tract in humans refers to the stomach and the intestine and sometimes to all the structures from the mouth to the anus. The upper gastrointestinal tract consists of the esophagus, stomach and duodenum. Some sources also include the mouth cavity and pharnyx. The exact demarcation between "upper" and "lower" can vary. Upon gross dissection, the duodenum may appear to be a unified organ, but it is often divided into two parts based upon function, arterial supply, or embryology. The integrated part of GI tract is pancreas and liver named the accessory organs of GI tract.

The lower gastrointestinal tract includes most of the small intestine and all of the large intestine. According to some sources, it also includes the anus. The intestine—or bowel—is divided into the small intestine and the large intestine. The small intestine has three parts: i) duodenum where the digestive juices from pancreas and liver mix together, ii) jejenum which is the midsection of the intestine, connecting duodenum to ileum and iii) ileum which has villi in where all soluble molecules are absorbed into the blood. The large intestine also has three parts: i) cacum where the vermiform appendix is attached to the cecum, ii) colon which consists of the ascending colon, transverse colon, descending colon and sigmoid flexure, and iii) rectum.

The intestine has two main roles: digestion and absorption of nutrients, and maintenance of a barrier against the external environment. It also forms the largest endocrine organ in the body as well as the largest and most complex part of the immune system.

In human adults the intestinal surface area is large, about 100 m$^2$. This large area is continuously exposed to different antigens in the form of food constituents (the adult human encounter 12.5 kg of pure protein/year), normal intestinal microflora and pathogens.

The intestinal mucosal surface is lined by a single layer of epithelial cells (IEC) which are continuously and rapidly replaced by replication of undifferentiated cells within the crypt ($7 \times 10^6$ cell/min). The epithelial cell layer of the intestinal mucosa is very complex and unique. It secrets digestive enzymes from the apical part to lumen for food digestion. It also secretes different proteins from the second half to the lamina properia (LP).

Further, said epithelial cells are receiving signals from both the lumen (and then transmitting the information to the diverse populations of cells in the LP) and the basolateral side. On the basolateral side the intestinal epithelial cells (IECs) receive many signals from various immune cells, nerve cells and stromal cells. Signals on both sides are affected by their respective microenvironments, influencing the functional states, behaviours, and structures of enterocytes resulting in integrity and homeostasis of the gastrointestinal tract (5).

One divides the postnatal development of the intestines into different phases: early suckling (change from amniotic fluid to colostrum), suckling (change from colostrum to milk), weaning (change from liquid diet, milk, to solid feed) and adulthood (adaptive changes due to diet variation) (Walthal K, et al., Birth Defects Research, 2005, part B, 74:132-156, review). Thus, by manipulating the condition on one side of the epithelial cell layer of the intestinal mucosal surface, the process of postnatal development of gut—including the intestine—could be accelerated or delayed. Past research has confirmed the possibility of accelerating the rate of gut maturation by using exogenous material like PHA (Radberg K, Biernat M, Linderoth A, Zabielski R, Pierzynowski S G & Westrom B R (2001) Enteral exposure to crude red kidney bean lectin induces maturation of the gut in suckling pigs. J Anim Sci 2001; 79:2669-2678) and IL-2 (Peulen O, Dandrifosse G. Spermine-induced maturation in Wistar rat intestine: a cytokine-dependent mechanism. J Pediatr Gastroenterol Nutr 2004, 38:524-532), but at present it is not known in detail as to which types of compounds that could induce fast acceleration.

Mammals are born with intestine that is not fully mature. Depending on the species, the complete maturation varies, but it is always achieved during the weaning period indicating that for the first couple of weeks all mammals haven an immature intestine. In rats, for example, the complete maturation coincides with the dietary shift from milk to solid food. Simultaneous with the onset of the maturation process, changes in the function and architecture of the epithelial cells in the intestine are seen as well as in the weight of the organs, the latter, of which is increasing in most mammals. Such functional and architectural markers are used to identify and measure the onset of the gut and intestinal maturation.

Investigation of gut development is quite a challenge. However, it is an attractive objective for many researchers in gastrointestinal area due to the fact that immature intestine and intestinal diseases are interrelated. In humans, for example, necrotizing enterocolitis (NEC) is the most common gastrointestinal problem in the neonatal intensive care unit (NICU). NEC syndrome is characterized by rapid necrotic death of intestine, involving 75% or more of total length of jejunum, ileum and colon. Development of NEC relates to maturity of gastrointestinal tract and up to 90% of cases refer to preterm born babies. The more preterm the infant is, the higher risk for NEC, and unfortunately, no nonsurgical treatment for this syndrome is officially reported. Therefore, NEC-related morbidity remains unchanged over the past 50 years. First described over a century ago necrotising enterocolitis (NEC) is now the most common gastrointestinal emergency occurring in neonates. It is an acquired disorder with a mortality as high as 50% (10-44% in infants less than 1500 g, 0-20% in infants over 2500 g). Prematurity and low birthweight are the most important risk factors. Average yearly infant death rate from NEC has been reported as 12.4 deaths per 100,000 live births with an incidence of 0.5 to 5 patients per 1000 live births. NEC is characterized by an immature gastrointestinal tract and high mucosal permeability to antigen leading to systemic shock and rapid death in some cases (Kosloske, A. M. Epidemiology of necrotizing enterocolitis. *Acta Paediatr. Suppl.* 1994; 396: 2-7).

At present, there are a very limited number of therapies known of a condition originating form an immature gastrointestinal tract such as e.g. necrotizing enterocolitis. Further, it is desirable to use less toxic substances, particularly in newborns. PHA (phytohaemagglutinin), which has previously demonstrated effects on intestinal maturation, such as induction of mitosis, increase in cell membrane permeability and transport across a membrane, is a lectin found in plants, especially legumes. The substance has a number of physiological effects and is used in medical research. In high doses, however it is a toxin. As a toxin, it can cause poisoning.

IL2 is an interleukin normally produced by the body during an immune response. IL-2 is also necessary during T cell development in the thymus for the maturation of subsets of T cells.

It may thus be less favorable to use PHA or IL2 in infants with gastrointestinal problem in a neonatal intensive care unit.

There is thus an urgent need to develop novel therapies and prevent disease such as necrotizing enterocolitis, particularly in newborn. Thus, understanding gastrointestinal development and particularly maturation of the small intestine is of great importance in newborns. Accordingly, the present invention seeks to provide means and methods to address such needs and interests.

SUMMARY OF THE INVENTION

One aspect of the present invention provides a method to induce maturation of an immature GI-tract, such as intestine, e.g. small intestine, the method comprising the steps of
a) administering a mixture of enzymes to the immature GI-tract, such as intestine, e.g. small intestine, said enzymes having a pancreatic activity or action, and/or pancreatic like activity or action,
b) analysing the maturation process of the immature GI-tract, such as intestine, e.g. small intestine to monitor said maturation process.

Further embodiments are wherein the immature GI-tract, such as intestine, e.g. small intestine is of mammalian origin, such as a cat, cow, horse, pig, rat, dog, mouse, or primate.

Further embodiments are wherein the immature GI-tract, such as intestine, e.g. small intestine is of human origin.

Further embodiments are wherein the immature human GI-tract, such as intestine, e.g. small intestine, is of a newborn.

Further embodiments are wherein the immature GI-tract, such as intestine, e.g. small intestine, is of an avian species.

Further embodiments are wherein at least one of intestinal enterocyte morphology, intestinal enterocyte biomarkers and weight of the GI-tract, such as intestine, e.g. small intestine, are analysed to monitor the maturation process, and wherein a change in at least one of intestinal enterocyte morphology, intestinal enterocyte biomarkers and weight of the GI-tract, such as intestine, e.g. small intestine, are indicative of intestinal maturation.

Still further embodiments are wherein said intestinal enterocyte biomarkers in the maturation process analysed are enterocyte disaccharidase activity and where changes in disaccharidase activities from lactase activity to sucrase activity and maltase activity of enterocytes in the GI-tract, such as intestine, e.g. small intestine, are indicative of GI-tract, such as intestine, e.g. small intestine, maturation.

Further embodiments are wherein said changes in intestinal enterocyte morphology in the maturation process are changes from foetal-type intestinal enterocytes to adult type intestinal enterocytes, and wherein said changes in morphology are indicative of GI-tract, such as intestine, e.g. small intestine, maturation process.

Still further embodiments are wherein said weigh of parts of the GI-tract, such as intestine, e.g. small intestine, analysed in the maturation process are changes of GI-tract, such as intestine, e.g. small intestine, weigh and wherein an increase of GI-tract, such as intestine, e.g. small intestine, weigh is indicative of the maturation process.

Even further embodiments are wherein the mixture of enzymes is administered orally.

Still even further embodiments are wherein the mixture of enzyme comprises at least one of a protease, a lipase and an amylase.

Even further embodiments are wherein the enzyme mixture comprises the enzymes protease, lipase and amylase.

Even further embodiments are wherein the mixture of enzymes is a one enzyme mixture, i.e. comprising only one enzyme with pancreatic and/or pancreatic like action or activity. Thus, further embodiments are wherein the mixture of enzyme comprises or consists of a protease.

Even further embodiments are wherein the mixture of enzyme comprises or consists of a lipase.

Even further embodiments are wherein the mixture of enzymes comprises or consists of an amylase.

Still even further embodiments are wherein the amount of enzymes is about 25 000-500 000 Ph Eur/kg bodyweight and day of the enzyme lipase, about 600-20 000 Ph Eur/kg bodyweight and day of the enzyme protease, and about 14 000 to 600 000 Ph Eur/kg bodyweight and day of the enzyme amylase.

Still further embodiments are wherein the maturation process takes about 3-10 days.

Further aspects of the invention are uses of a mixture of enzymes having pancreatic activity or action to induce maturation of an immature GI-tract, such as intestine, e.g. small intestine.

Further aspects of the invention are uses of a mixture of enzymes having pancreatic like action or activity to induce maturation of an immature GI-tract, such as intestine, e.g. small intestine.

Further embodiments are wherein the immature GI-tract, such as intestine, e.g. small intestine, is of a newborn.

Further embodiments are wherein the immature GI-tract, such as intestine, e.g. small intestine, is of an avian species.

Further aspects of the invention are a mixture of enzymes having pancreatic and/or pancreatic like action or activity for inducing maturation of an immature GI-tract, such as intestine, e.g. small intestine.

Further aspects of the invention provide a mixture of enzymes having pancreatic and/or pancreatic like action or activity for treatment of a disorder relating to an immature GI-tract, such as intestine, e.g. small intestine.

Further embodiments are wherein said immature GI-tract, such as intestine, e.g. small intestine, disorder is necrotizing enterocolitis. Further embodiments are wherein said disorder is a gut involution, disorder or a disfunction of a GI-tract of an elderly subject.

Further aspects of the invention provide use of a mixture of enzymes having pancreatic and/or pancreatic like action or activity for the preparation of a medicament for treatment of an immature gastrointestinal tract disorder, such as an intestinal disorder e.g. small intestinal disorder.

Further embodiments are wherein said immature gastrointestinal tract disorder, such as an intestinal disorder e.g. small intestinal disorder is necrotizing enterocolitis. Further embodiments are wherein said disorder is a gut involution, disorder or a disfunction of a GI-tract of an elderly subject.

Further aspects of the invention provides a method of treating an individual with an immature gastrointestinal tract disorder, such as an intestinal disorder e.g. small intestinal disorder, said method comprising the steps of administering to a patient in the need thereof an effective amount of a mixture of enzymes with pancreatic and/or pancreatic like action or activity to induce gastrointestinal tract maturation, such as an intestinal e.g. small intestinal maturation.

Further embodiments are wherein said disorder of an immature GI-tract, such as intestine, e.g. small intestine, is necrotizing enterocolitis or a disfunction of a GI-tract of an elderly subject.

Further embodiments are wherein said patient in the need thereof is an infant or an elderly.

Further embodiments is improved body growth by amylase of newborn and new hatched avians as well as older and aging mammals including humans and older avians.

Further aspects of the present invention provides a kit for inducing maturation of an GI-tract, such as intestine, e.g. small intestine, said kit comprising
a) a mixture of enzymes with pancreatic and/or pancreatic like action or activity to induce gastrointestinal tract, such as an intestinal e.g. small intestinal maturation,
b) instructions to induce gastrointestinal tract, such as an intestinal e.g. small intestinal maturation according to any of the methods disclosed herein.

BIgG, bovine immunoglobulin G; BSA, bovine serum albumin.

Figure 7:
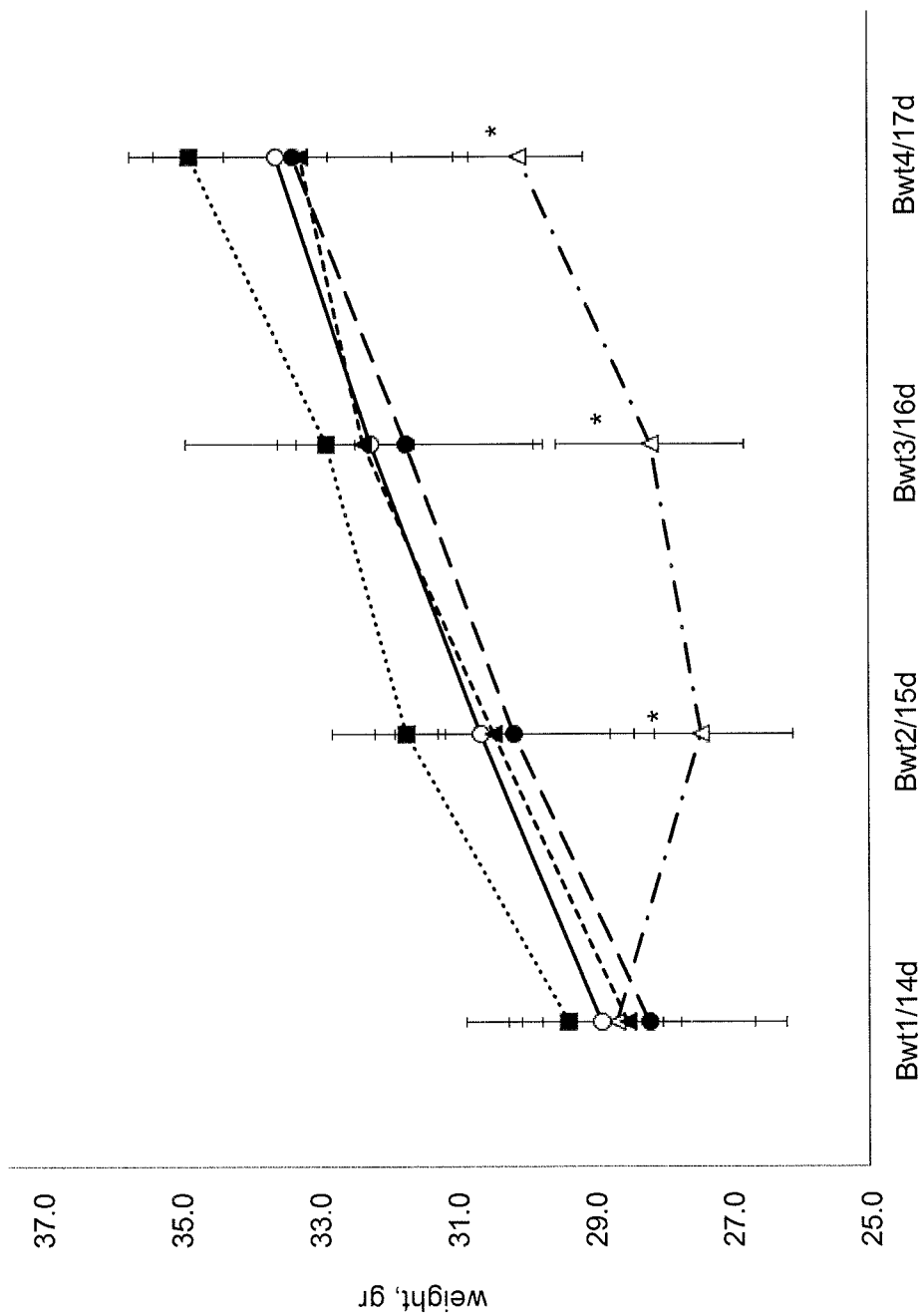

FIG. 7 shows the effects of different doses of protease on rat body weight gain during treatment (14, 15 and 16 days of age: Bwt1, Bwt2, Bwt3, respectively) and 24 hours after last feeding (Bwt4). Results are expressed as mean±SD. Treated groups were compared to control using Student t-test. *P<0.05

Bwt, body weight. Non-filled triangle—15 000 USP, non-filled circle—7 500 USP, filled triangle—3 750 USP, filled circle—1875 USP and filled square—control.

Figure 8:
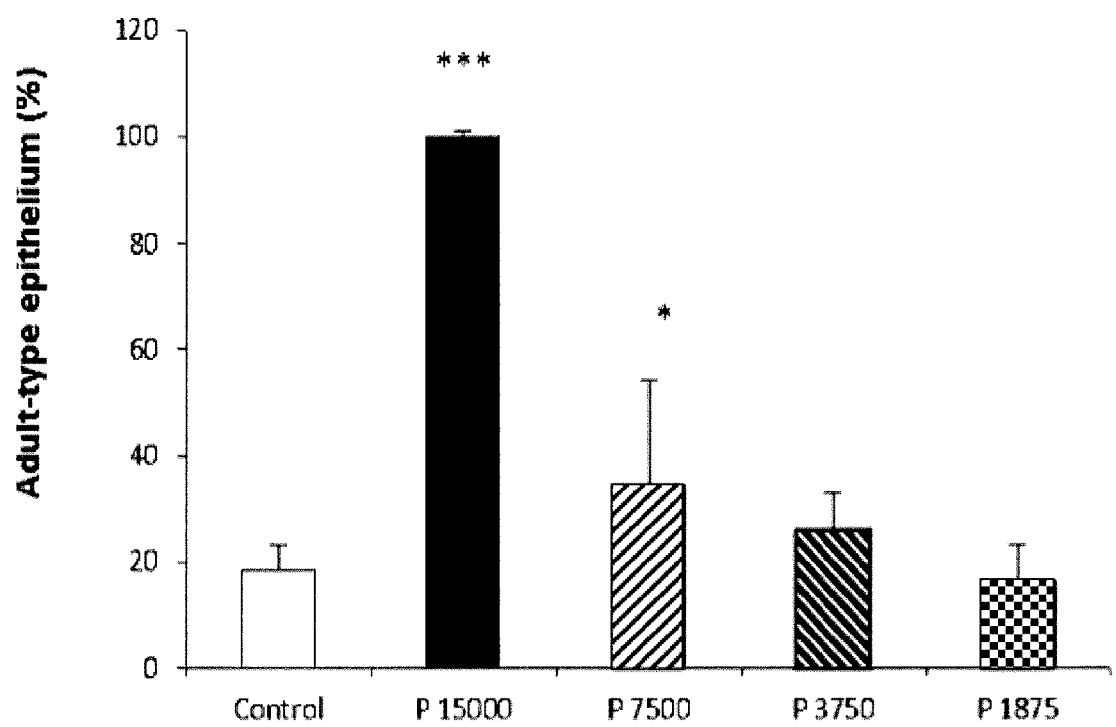

FIG. 8 shows the maturity of the rat intestinal epithelium in the distal small intestine after treatment with different doses of protease: (P 15 000=Protease 15 000 USP; P 7500=Protease 7 500 USP; P 3750=Protease 3 750 USP; P 1875=Protease 1 875 USP). Results are expressed as mean±SD. Treated groups were compared to control using Student t-test. * P<0.05, ** P<0.01.

USP, United States Pharmacopeia

Figure 9:
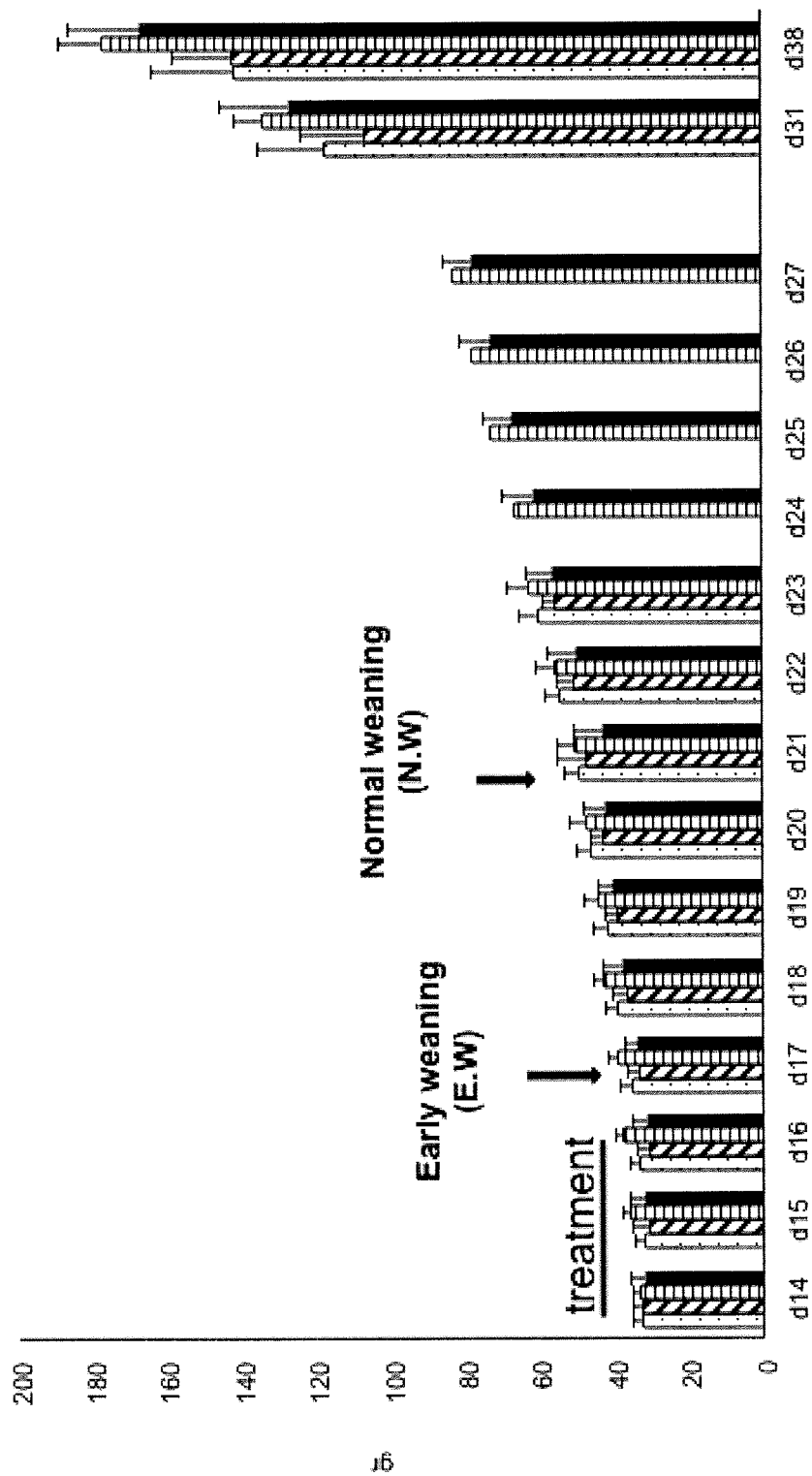

FIG. 9 shows the effect of high dose of protease (P 15 000 USP) on body weight gain of rats during treatment, early and normal weaning up to 38 days of life in comparison to control groups. Results are expressed as mean±SD. Dotted bars are control, early weaning/EW, horizontally striped bars are control, normal weaning/NR, diagonally striped bars are Enzyme mixture, early weaning/EW, Black barrs are enzyme mixture, normal weaning/NR.

USP, United States Pharmacopeia

Figure 10:
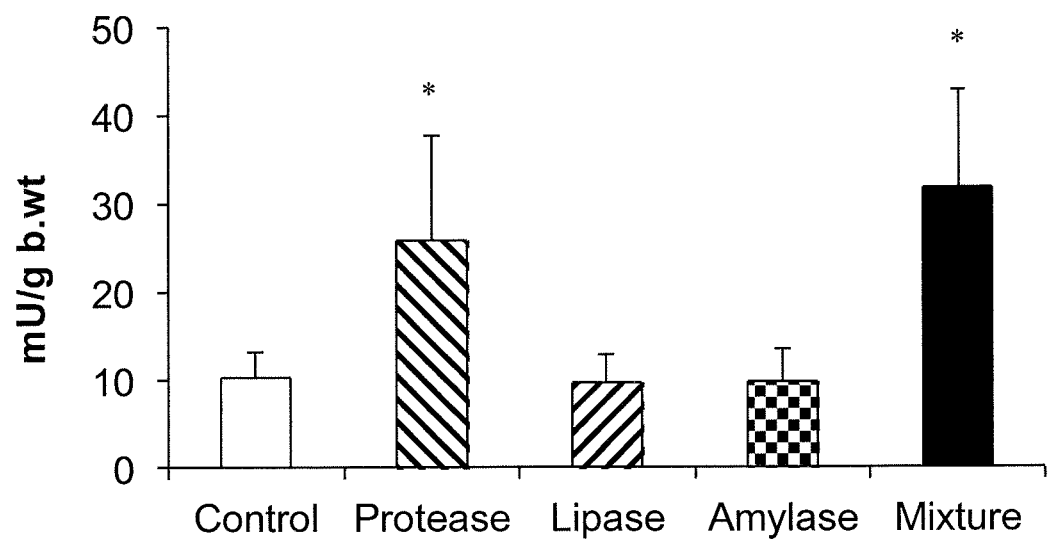

FIG. 10 shows the effect of microbial-derived enzymes with pancreatic activity: protease, lipase, amylase and their mixture on rat trypsin activity in the pancreatic homogenates after 3 d of oral gavage to suckling 14 d old rats. Treated groups were compared to control, *p<0.05.

Figure 11:
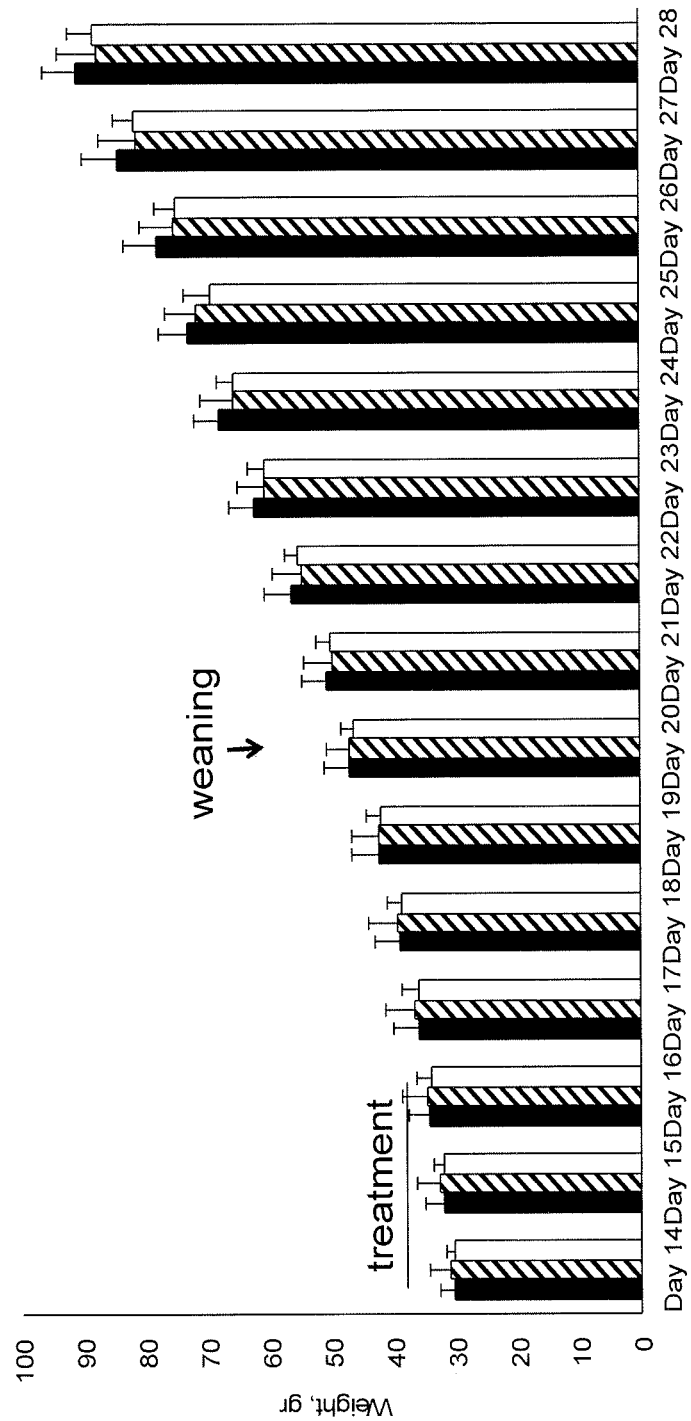

FIG. 11 shows the growth of young rats treated at age 14-16 d of life once a day with microbial-derived enzymes having lipase and amylase activities, n=7 per group. Black bars are amylase, striped bars are lipase and open bars are control.

Figure 12:
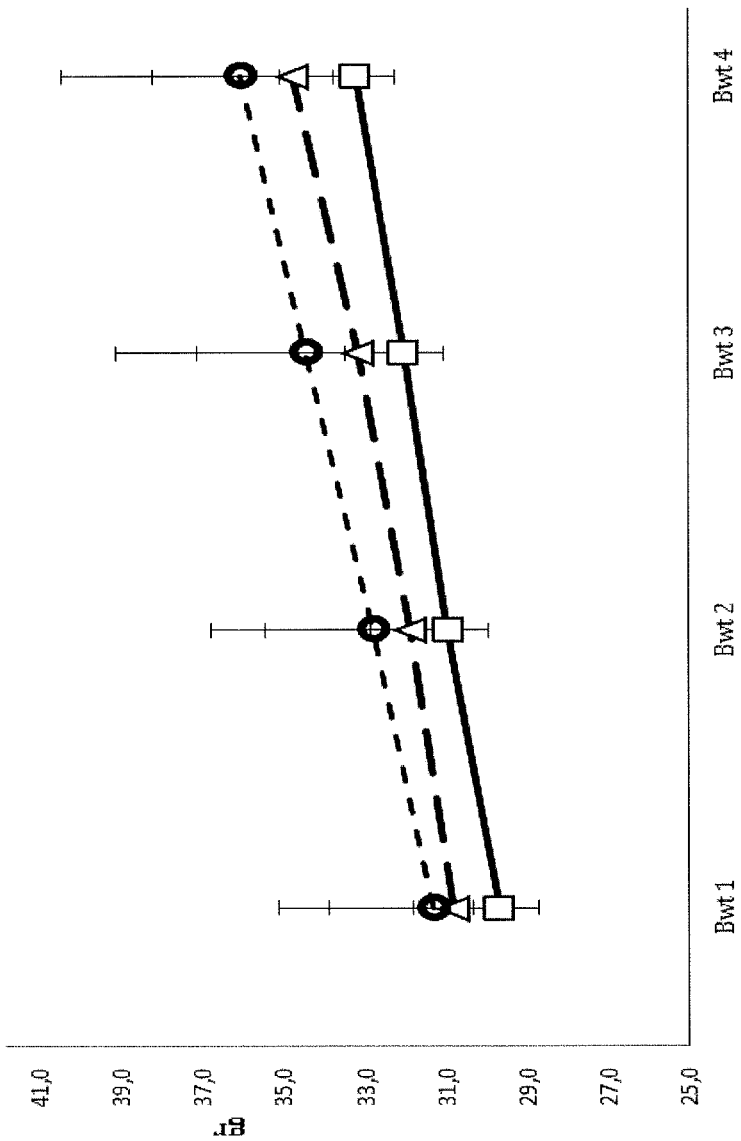

FIG. 12 shows the effects of proteases on body weight of suckling rats during 14 to 17 days of age, n=7-8 per group. Graph is demonstrating the growth of suckling pups during experiment. There is no effect of protease or papain in dose 10 000 USP on body growth was observed. Control is shown in circles, papain is shown in squares and protease is shown in triangles.

Figure 13:
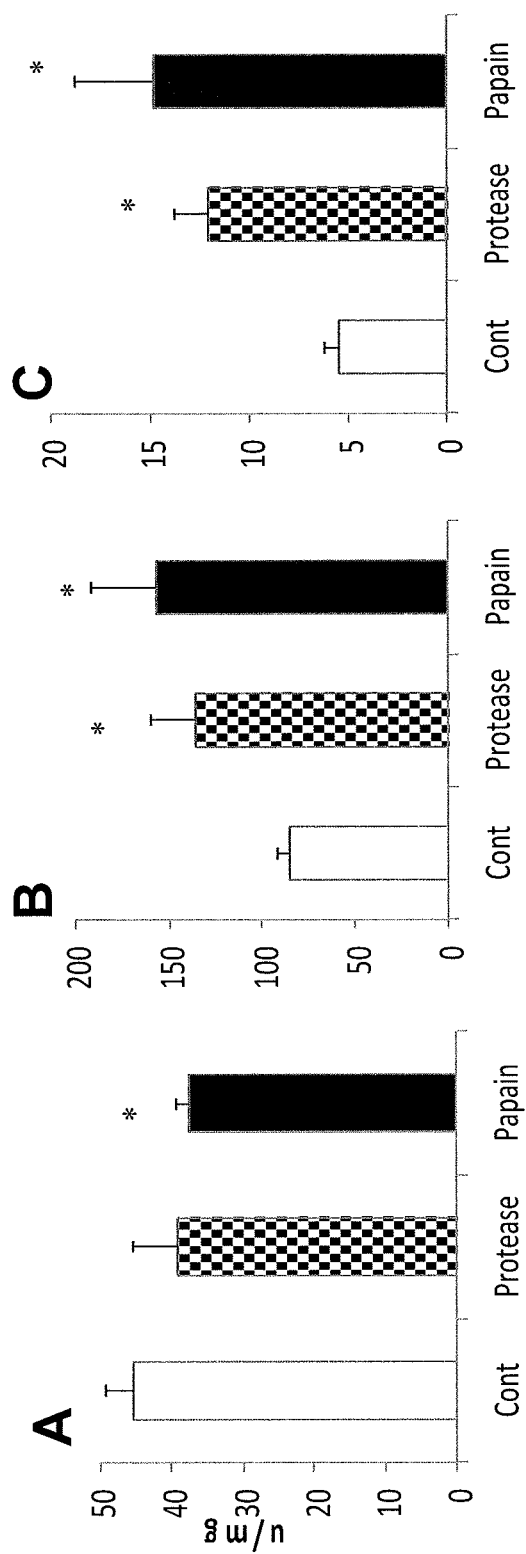

FIG. 13 shows results of activities of the brush-border enzymes lactase (13A), maltase (13B) and sucrase (13C) analyzed in the proximal part of the rats SI in groups treated with papain and protease. Results are expressed as mean±SD. *p<0.05.

Figure 14:
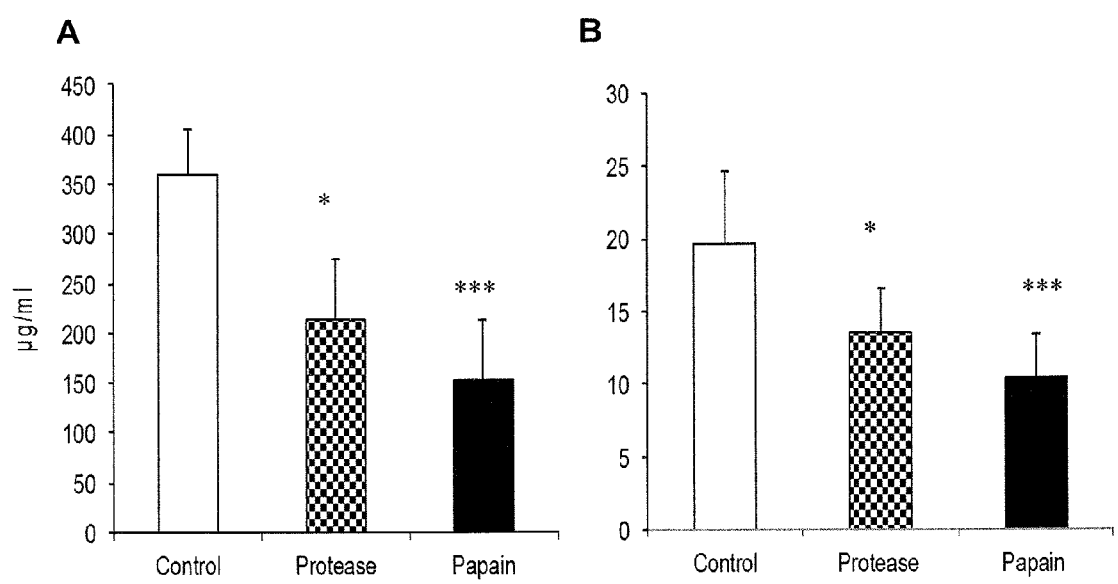

FIG. 14 shows the effect of microbial protease and fruit protease on the level of marker molecules absorption to the plasma in rats, after feeding them with cocktail of BSA (14B) and BIg G (14A) on day 17, (at 3 hours before dissection). These data are given as mean±SD. Significant results; * p<0.05; ***p<0.001.

Figure 15:
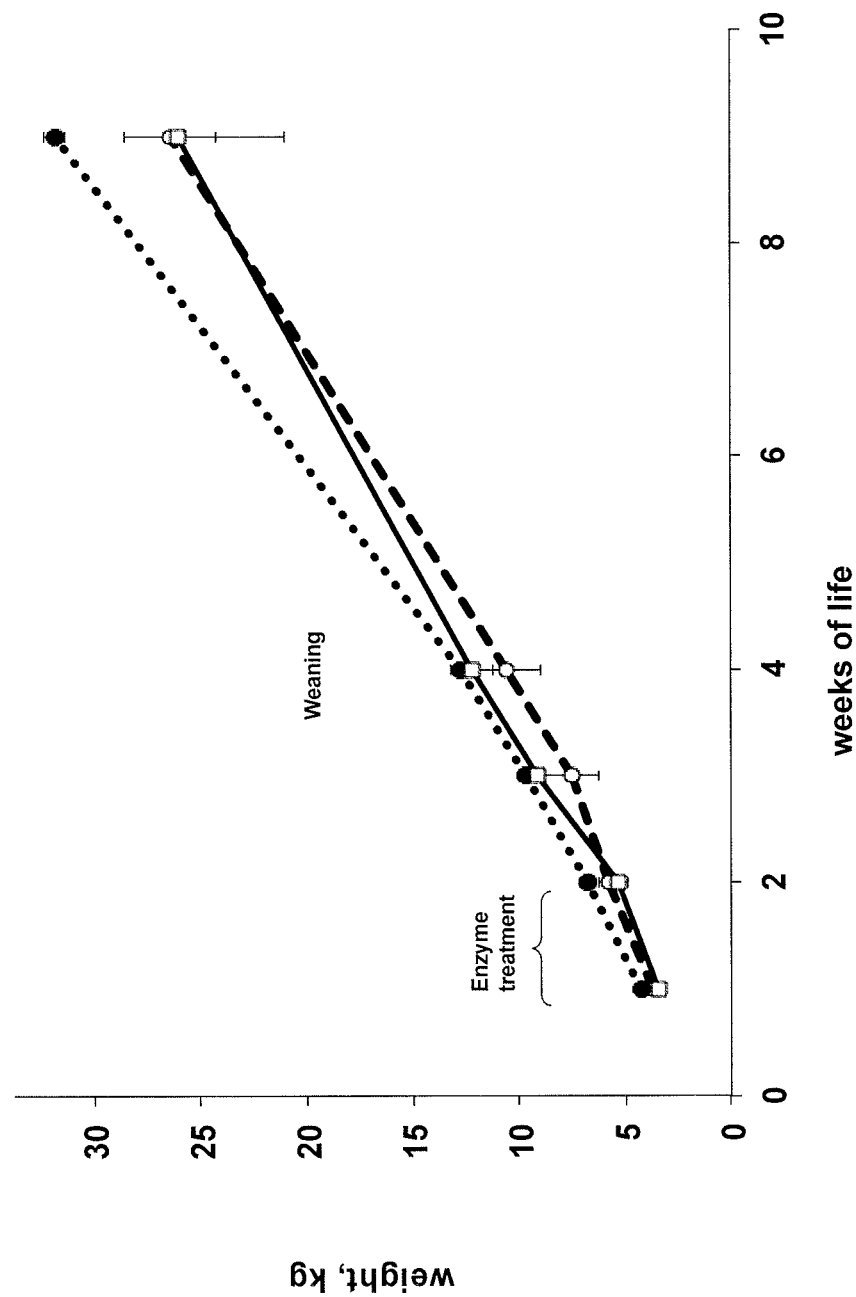

FIG. 15 shows the effect of enzyme treatment with porcine Creon and microbial enzymes mixture on pigs body growth, n=12-6 per group. Open circles are control, mixture of microbial enzymes are black circles and Creon are open squares.

Figure 16:
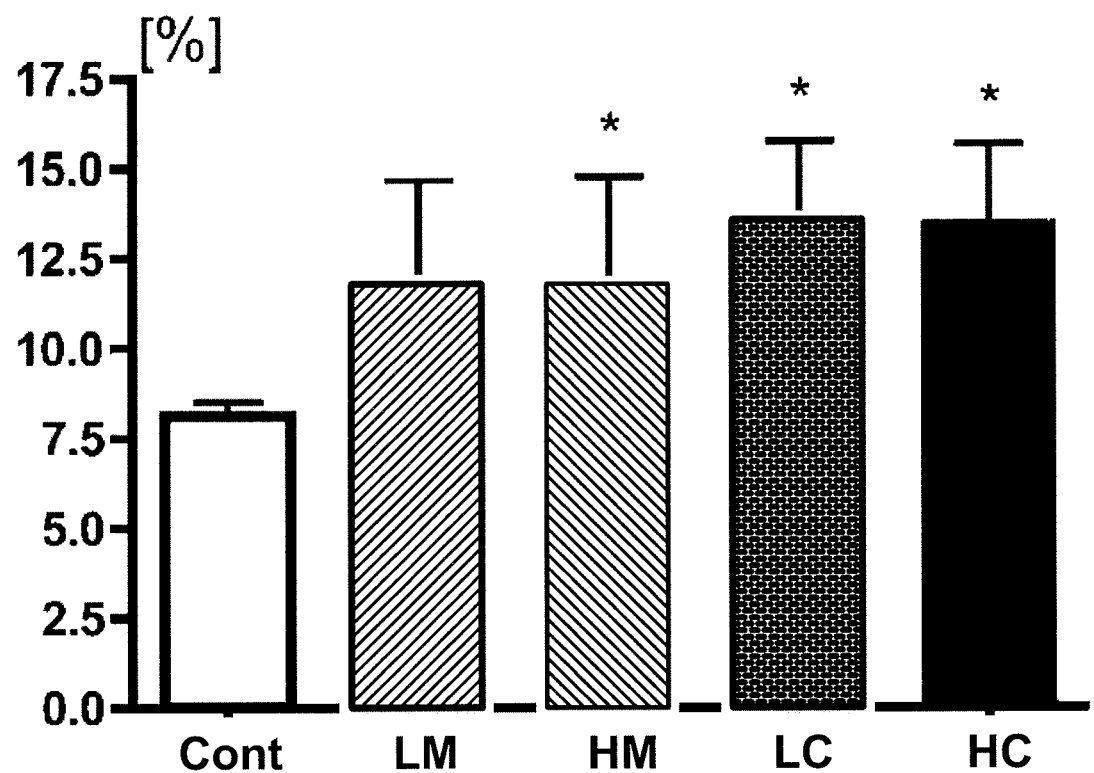

FIG. 16 shows the Crypt cell proliferation in the small intestine of suckling 14-15 d old piglets after 1 week gavage treatment (twice a day) with preparation of enzymes having pancreatic-like activities of porcine and microbial origin. Groups were compared to control, *p<0.05. Cont, control; LM, low dose mixture; HM, high dose mixture; LC, low dose Creon, HC, high dose Creon.

Figure 17:
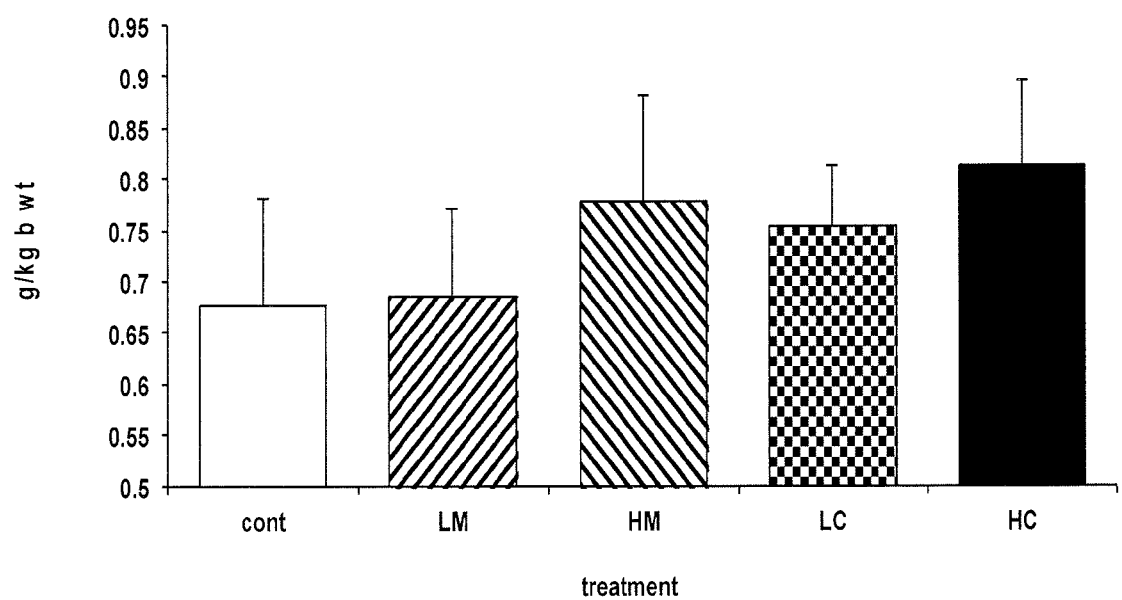

FIG. 17 shows weight of the small intestine of suckling 14-15 d old piglets after 1 week gavage treatment (twice a day) with preparation of enzymes having pancreatic-like activities of porcine and microbial origin. Cont, control; LM, low dose mixture; HM, high dose mixture; LC, low dose Creon, HC, high dose Creon. Result demonstrate tendency of small intestine to increase its weight in dose-respond manner.

Figure 18:
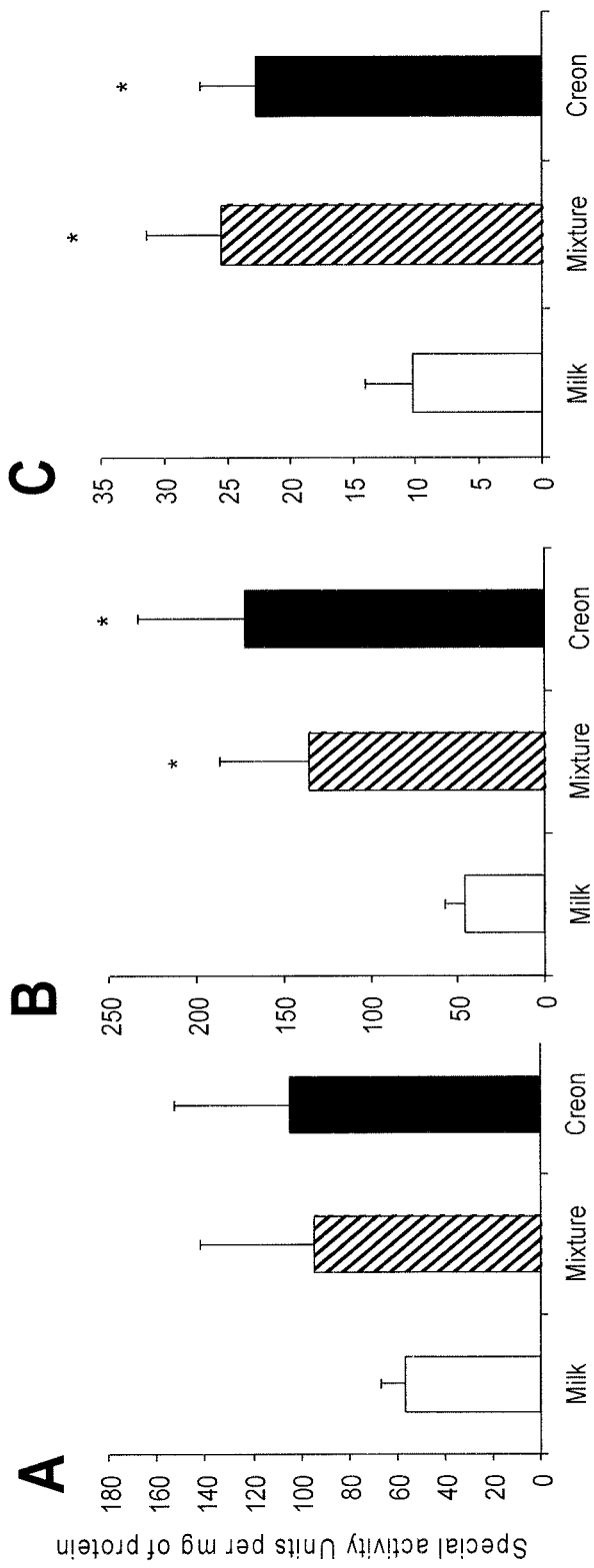

FIG. 18 disaccharidase activities: A-lactase, B-maltase, C-sucrase in the small intestine of suckling 14-15 d old piglets after 1 week gavage treatment (twice a day) with high dose preparation of enzymes having pancreatic-like activities of porcine and microbial origin. Groups were compared to control (n=3-5), *p<0.05.

Figure 19:
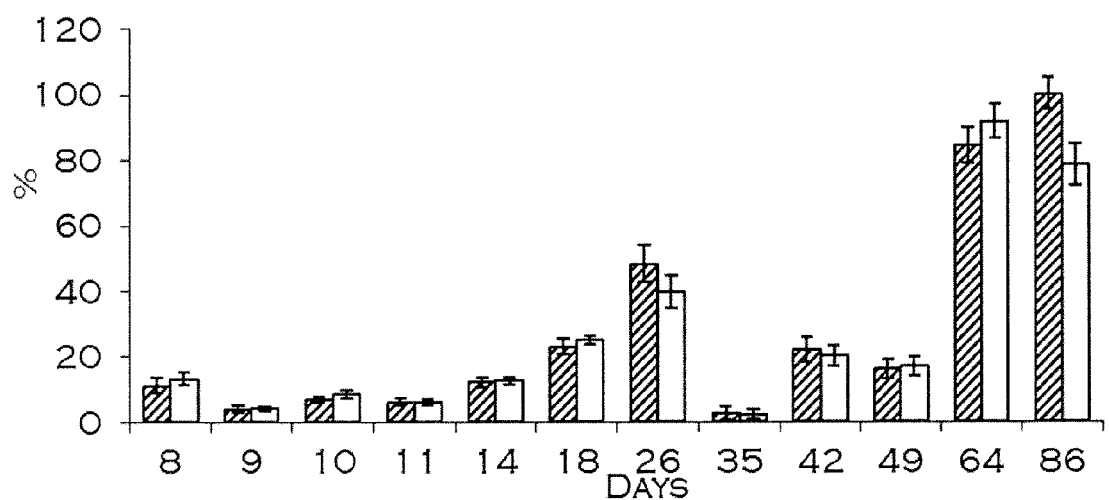

FIG. 19 shows effect of microbial-derived protease on bogy weight gain in % where striped bars show treated pigs and open bars show control.

Figure 20:
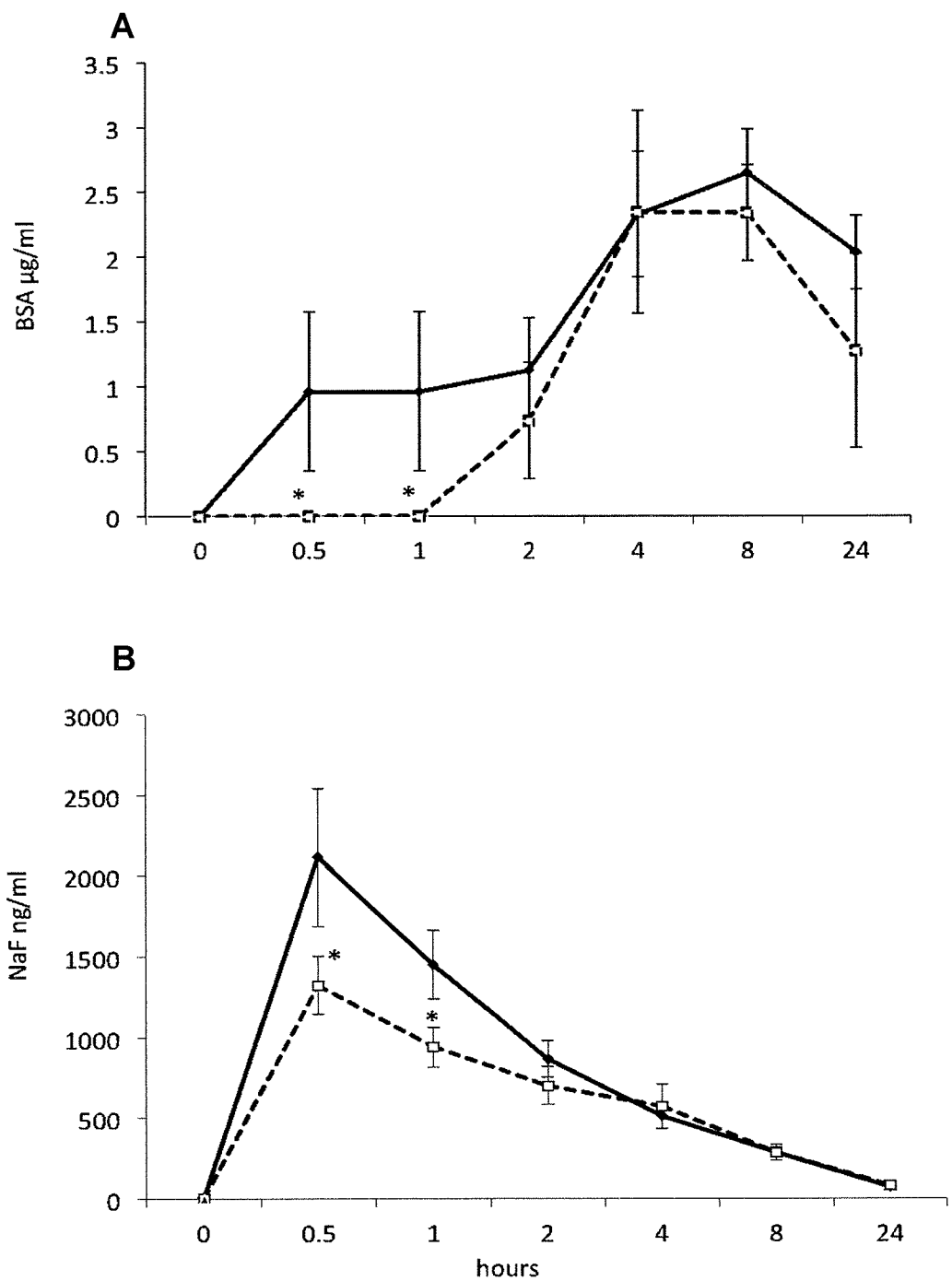

FIG. 20 shows the effects of microbial enzyme on marker molecules absorption in pigs. The results demonstrate decreased intestinal permeability for both BSA (20A) and NaF (20B) molecules in protease treated piglets (n=8) in comparison to control (n=8). *p<0.05.

Figure 21:
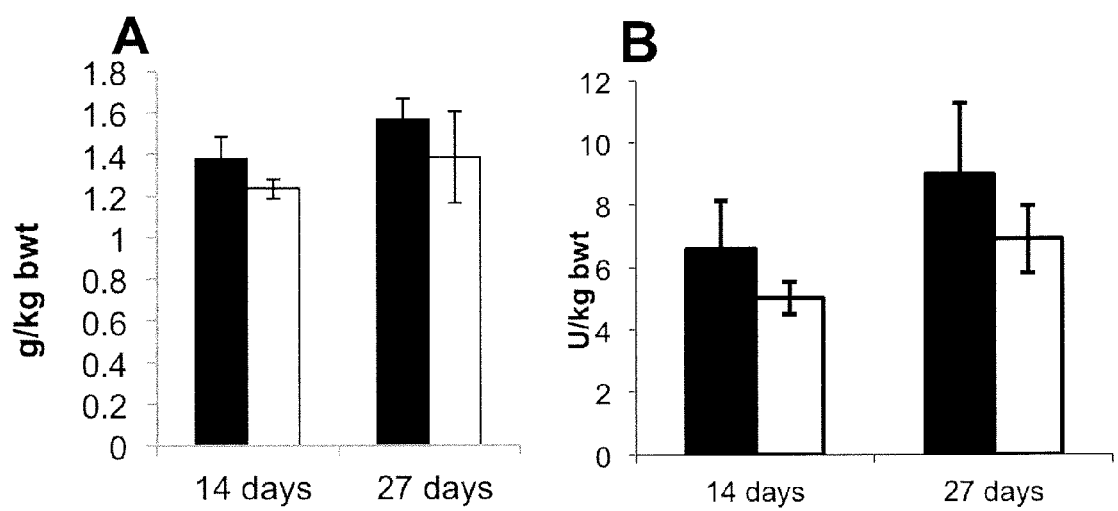

FIG. 21 shows the effect of protease on pancreatic function after 3 times administration, starting at 8 d of life and every other day, the results represent material taken at 48 h after last enzyme treatment (14 d) and at weaning time (27 d). FIG. 21A shows pancreas weight, 21B trypsin like activity. Black bars are enzyme treated and open bars are control.

DETAILED DESCRIPTION OF THE INVENTION

Definitions

As used herein the "gastrointestinal (GI) tract" is, when referring to humans, non-human mammals and avian species, intended to mean the stomach and the intestine and gut accessory organs, pancreas and liver, and sometimes to all the structures from the mouth to the anus. The upper gastrointestinal tract consists of the esophagus, stomach and duodenum. Some sources also include the mouth cavity and pharnyx. The exact demarcation between "upper" and "lower" can vary. Upon gross dissection, the duodenum may appear to be a unified organ, but it is often divided into two parts based upon function, arterial supply, or embryology.

The lower gastrointestinal tract includes most of the small intestine and all of the large intestine. According to some sources, it also includes the anus. The intestine—or bowel—is divided into the small intestine and the large intestine. The small intestine has three parts: i) duodenum where the digestive juices from pancreas and liver mix together, ii) jejunum which is the midsection of the intestine, connecting duodenum to ileum and iii) ileum which has villi in where all soluble molecules are absorbed into the blood. The large intestine also has three parts: i) cacum where the vermiform appendix is attached to the cecum, ii) colon which consists of the ascending colon, transverse colon, descending colon and sigmoid flexure, and iii) rectum. The GI tract in humans thus also include liver, pancreas, small and large intestine, if applicable to that particular species. Other mammals or avian species may have the same or different organs of the GI-tract. Thus, the particular organs included in GI-tract are species dependent.

As used herein, a "small intestine" is intended to mean the part of the 'gastrointestinal part following the stomach and followed by the large intestine, and is where the vast majority of digestion and absorption of food takes place. The small intestine in an adult human measures on average about 5 meters (16 feet), with a normal range of 3-7 meters; it can measure around 50% longer at autopsy because of loss of smooth muscle tone after death. It is approximately 2.5-3 cm in diameter. Although the small intestine is much longer than the large intestine (typically around 3 times longer), it gets its name from its comparatively smaller diameter. Although as a simple tube the length and diameter of the small intestine would have a surface area of only about 0.5 m$^2$, the surface complexity of the inner lining of the small intestine increase its surface area by a factor of 500 to approximately 200 m$^2$, or roughly the size of a tennis court.

The small intestine, both for mammals and avian species, is divided into three structural parts, i) duodenum, ii) jejenum and iii) ileum.

As used herein, "pancreatic like activity" and/or "pancreatic like action" is intended to mean any enzyme activity having the same, equal or similar activity or action as pancreatic enzymes. "Pancreatic enzymes" or "enzymes with pancreatic activity or action" are enzymes secreted by the pancreas. Examples of pancreatic enzymes or enzymes with pancreatic activity are given herein.

As used herein, "subject" is intended to mean any mammal including human having or suspected of having a disease, as well as a normal healthy subject. A "subject" includes a patient, such as a human patient having or suspected of having a disease. "Subject" as used herein also denotes a mammal, such as a rodent, e.g. a mouse or a rat, a pig, a feline, a canine, and a primate. Preferably a subject according to the invention is a human. A subject may also be of avian origin, such as a turkey, duck, hen, chicken or broiler.

As used herein, the singular forms "a", "and", and "the" include plural referents unless the context clearly dictates otherwise. Thus, for example, reference to "a biomarker" includes a plurality of such biomarkers.

As used herein "d" refers to "day" or "days".

As used herein "at least one" is intended to mean one or more, i.e. 1, 2, 3, 4, 5, 6, 7, 8, 9, 10, etc.

As used herein "infant" is intended to mean a child or baby as the very young offspring of humans. Further, as used herein a "newborn" or "neonate" is an infant who is within hours, days, or up to a few weeks from birth. As used herein, a "newborn" or "neonate" also includes mammals of non-human species as well as avian species who is within hours, days, or up to a few weeks from birth. A "newborn" or "neonate" thus refers to an infant in the first 28 days of life (less than a month old) as well as mammals of non-human species in the first 28 days of life as well as avian species in the first 7 days of life. The term "newborn" includes premature infants, postmature infants and full term newborns.

As used herein "elderly" or "old" or "older" is intended to mean the definition according to WHO and UN as of today (http://www.who.int/healthinfo/survey/ageingdefnolder/en/index.html). The definition as such is an arbitrary definition where most develop countries uses an age of 65+ to define elderly, whereas this does not adapt well to developing countries like Africa. At the moment, there is no United Nations standard numerical criterion, but the UN agreed cutoff is 60+ years to refer to the older population. Thus, the working definition of "elderly", "older" or "old" for the purposes of developing countries like Africa should be changed to the age of 50 years. It is acknowledged that this is also somewhat arbitrary but it is believed to be a better representation of the realistic working definition in developing countries like Africa.

For animal species and "old", "older" or "elderly" differs between different species, of course. The case for gerbils, as used herein, is about 24 months of age and above. The case for mice is 24 and rat is 36 months.

"Detection", "detect", "detecting" as used herein includes qualitative and/or quantitative detection (measuring levels) with or without reference to a control, and further refers to the identification of the presence, absence, or quantity of a given substance, e.g. mRNA or protein or any other substance, or activity, such as e.g. any enzymatic activity.

"Healthy" refers to a subject possessing good health. Such a subject demonstrates a normal GI tract including the intestine, e.g. the small intestine, mature or immature, and is wherein the maturation process of the intestine proceeds normal. In the context of this application, a "healthy individual" or "healthy subject" is only healthy in that they have a normal intestinal maturation process, a "healthy individual" or "healthy subject" may have other diseases or conditions that would normally not be considered "healthy".

"Treatment" or "therapy" as used herein is defined as the attempted remediation of a health problem and includes e.g. management of a patient through medical or surgical means. The treatment or therapy improves or alleviates at least one symptom of a medical condition or disease and is required to provide a cure. The term "treatment outcome" or "outcome of treatment" as used herein is the physical effect upon the patient of the treatment. Further, "treatment" includes both therapeutic and prophylactic treatment of a subject or patient. E.g. the term "prophylactic" is used to encompass the use of an enzyme mix or formulation described herein which improves intestinal maturation or alleviates at least one symptom of a medical condition or disease due to absence of intestinal maturation in a mammal such as a subject or a patient.

Persons skilled in the art will further appreciate that the enzyme mixtures or the enzyme alone described herein have utility in both the medical and veterinary fields. Thus, the enzyme mixture in all its embodiments herein may be used in the treatment of both human and non-human animals, such as horses, dogs, mice, rats, apes, monkeys, pigs, and cats. Preferably, however, the patient is human, such as a newborn infant or neonatal. Also included here are wherein the enzyme mixtures described herein in all its embodiments are used in treatment of avian species, i.e. birds, e.g. in chickens or broilers of hens, ducks, turkeys etc.

During the last decade, researchers have induced and accelerated gut maturation by using exogenous factor like PHA. As PHA is a compound accompanied by many undesirable effects and it can use only as tool, there is a need to search for a new source, ideally one that is endogenous. As revealed above, the present invention uses an enzyme mixture with pancreatic activity or action, or pancreatic like activity or action, to induce maturation of the GI tract including the intestine, e.g. the small intestine.

Figure 1A:
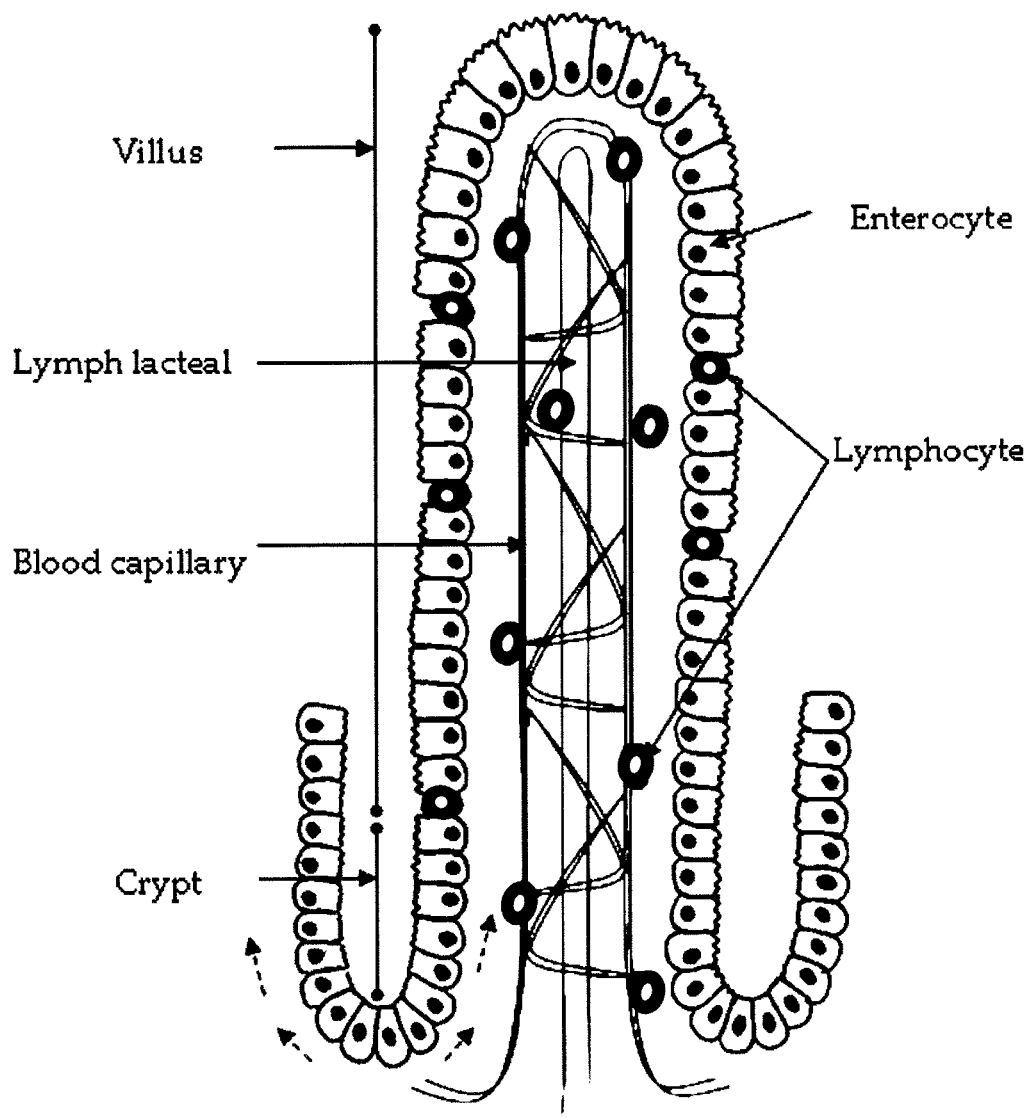
FIG. 1a-1b shows in a) a schematic illustration of villi-crypt unit. Broken arrows show the direction of enterocyte replacement and in b) photomicrographs of H&E stained distal small intestinal sections, showing the enterocytes phenotype: fetal-type (left panel), 14 d-old suckling rat, and adult-type (right panel) 6 months-old rat.
Figure 1B:
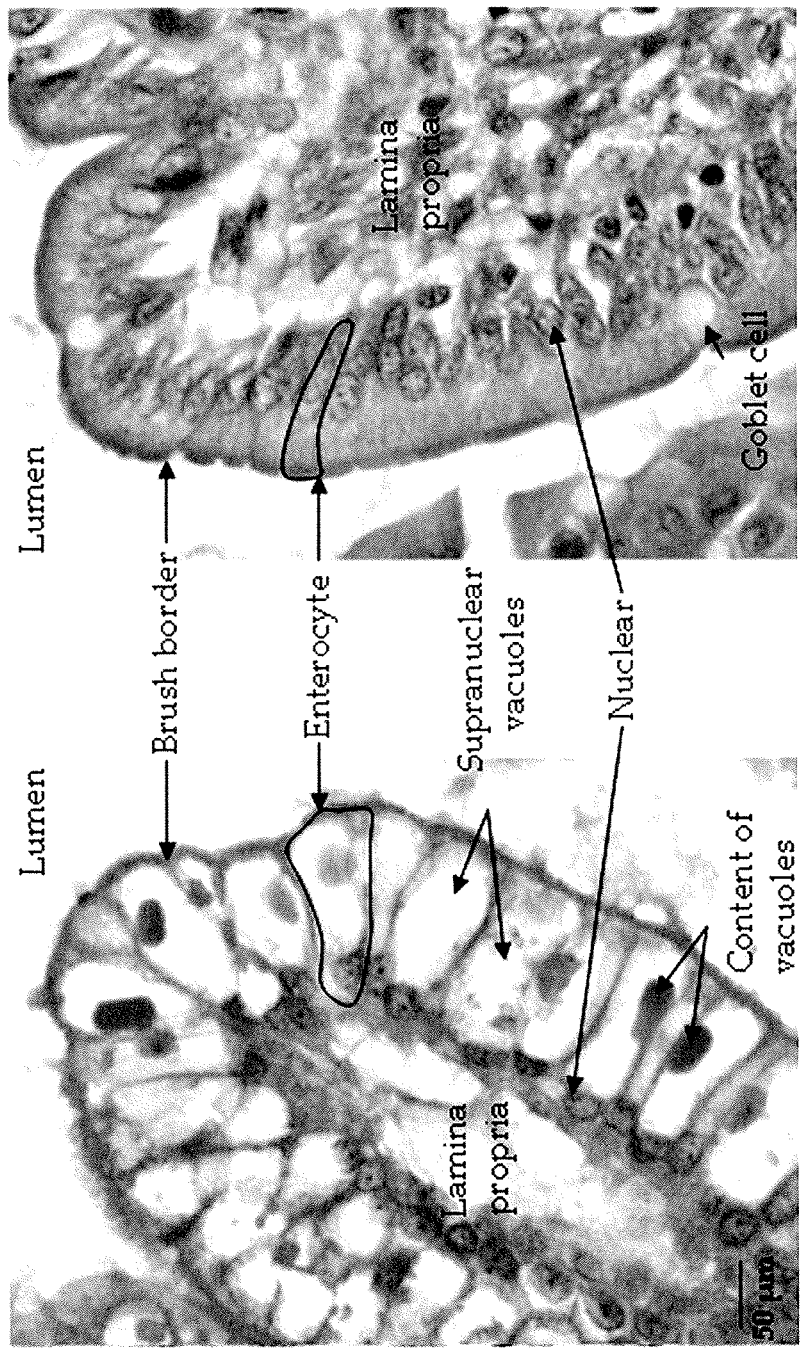

Before the full maturation of a GI tract including the intestine and accessory organs, e.g. the small intestine and pancreas, and simultaneous with the onset of maturation, many changes have been recorded—most of these events are related to the functional and architecture of the epithelial cell in the intestines and the weight of organs, e.g. the intestine as such. For instance, in rats it has been noted that there is an increase in maltase and sucrase activity of intestinal enterocytes as well as the disappearance of vacuolated epithelial cells of an immature intestine in distal parts, being replaced by adult phenotypes (see FIGS. 1a and 1b). These changes, therefore, may be used as a potential marker for the onset of gut maturation (see e.g. Baintner K. Vacuolization in the young. In: Zabielski R, Gregory P S, Westrom B (eds). *Biology of the intestine in growing animals.* Amsterdam: Elsevier Science B. V; 2002:55-110, and Walthall K, Cappon G D, Hurtt M E, et al. Postnatal development of the gastrointestinal system: a species comparison. *Birth Defects Res* 2005; 74:132-56 incorporated herein by reference).

Parallel with the events in the epithelial layer of the intestine during maturation many organs, proteins and cell profiles of the immune system in the lamina propria (LP) undergo modification as well in response to changes in the microenvironment during the maturation process. It has been shown there is an increase in inflammatory profile like IL-6 and TNF, as well as T-cell expansion, during the weaning period as compared with the suckling period.

The present invention thus in one aspect relates to a method to induce and monitor maturation of an immature GI tract including the intestine, e.g. the small intestine. Said method comprises the steps of a) administering a mixture of enzymes to the immature GI-tract, said enzymes having a pancreatic activity or action, or pancreatic like activity or action, b) analysing the maturation process of the intestine to monitor said maturation process.

Said method may also in further embodiments include the step to prevent and monitor gut involution, disorders and dysfunctions at elderly by the steps a and b in the method to induce and monitor maturation of an immature GI-tract. The enzyme mixture is described and exemplified further herein and all embodiments may be used in all the methods and uses herein.

The above method may relate to any subject of mammalian species, such as human or non-human origin or avian GI tract, e.g. the intestine, more particularly the small intestine, such as an intestine of a rat, mouse, rabbit, guinea pig or any other rodent, cat, cow, sheep, horse, or a pig. It may also be an intestine of an avian species such as a bird, a hen, turkey, or duck, or chicken or broilers thereof, or it may also be a human intestine, from an adult or a child or infant, or even a newborn infant, including a premature infant, postmature infants and full term newborns. Newborns' digestive tracts, which of course have never been used prior to birth, are filled with a greenish-black, sticky material called meconium. This has the function of standing in for fecal material and allows the intestines to develop to the point where they can process milk immediately on birth. This meconium material is passed by the child in the first few days. The digestive tract is, during suckling and breast feeding still considered as relatively immature compared to adults and the process of maturation is further induced normally during the weaning process.

Further embodiments are thus wherein the immature GI tract including the intestine, e.g. the small intestine, is of mammalian origin.

Even further embodiments are wherein the immature GI tract including the intestine, e.g. the small intestine, is of human origin.

Still even further embodiments are wherein the immature human GI tract including the intestine, e.g. the small intestine is of an infant, such as e.g. a newborn infant, including a premature infants, postmature infants and full term newborns.

Even further embodiments are wherein the immature GI-tract including the intestine, e.g. the small intestine, is of avian origin.

There are thus certain characteristics of an immature GI tract including the intestine, e.g. the small intestine, and further certain characteristics associated to a mature intestine. Characteristical changes in between the immature and mature intestine, i.e. changes during the maturation process, include i) structural changes of enterocytes from foetal type enterocytes to adult type enterocytes, ii) functional changes of enterocytes that includes a change in disaccharide activities from a predominant lactase activity in the immature mode to a sucrase and maltase activity in the adult mode, and iii) a change in weight, e.g. an increase, in organ weight, for example weight of the intestine, such as the small intestine, or the liver or pancreas. The functional change of the enterocytes may thus be used as biomarkers if the maturation process.

Analysing the maturation process of the intestine to monitor said maturation process may thus be analysing at least one of intestinal enterocyte morphology, intestinal enterocyte biomarkers and weight of the parts of the GI-tract such as the intestine, e.g. small intestine, are analysed to monitor the maturation process in the methods given herein, and wherein a change in at least one of intestinal enterocyte morphology, intestinal enterocyte biomarkers and weight of the organs of the GI tract including the intestine, e.g. the small intestine, are indicative of gastrointestinal tract maturation, such as an intestinal e.g. small intestinal maturation.

Analysing the maturation process may further include, apart from the above characteristics, analysing brush border disaccaridase activity asintestinal enterocyte biomarkers in the maturation process. Changes in disaccaridase activities from predominant lactase activity to sucrase activity and maltase activity of enterocytes in the small intestine (IEC) are indicative of gastrointestinal tract maturation, such as an intestinal e.g. small intestinal, maturation.

Various disaccharidases (maltase, isomaltase, sucrase, and trehalase) falls into this category and thus their developmental patterns are indirect contrast to that of lactase. Maltase has low activity during the first two postnatal weeks and then undergoes a 5- to 10-fold increase during the next two weeks. For sucrase, isomaltase, and threalase, the transition is even more sudden. These enzymes cannot be detected in the intestine during the first and second postnatal week, but their activities appear on approximately day 16 and rise rapidly, reaching adult levels by the end of the fourth week. When providing an enzyme mixture with pancreatic activity or action, or pancreatic like activity or action, such a change in enzyme activity will appear much quicker, after a few days such as about 2, 3, 4, 5, 6, 7, 8, 9, or 10 days.

Disaccharidase is a group of enzymes which are components of the brush border of the intestinal epithelium and which hydrolyze disaccharides to monosaccharides. The disaccaridase enzymes include but are not limited to lactase, maltase, sucrase, trehalase, isomaltase and galactosidase. Enteric infections may cause a temporary deficiency of lactase leading to the development of an osmotic-type diarrhoea. All disaccharidases are not present immediately following birth and feeding sucrose to young calves will result in diarrhoea.

Assays to measure intestinal brush-border disaccharidase activity are known in the art. It includes specific colorimetric assays of glucose with glucose oxidase of disaccharidase activities, since most naturally occurring disaccharides contain at least one molecule of glucose which is liberated on hydrolysis. The method is especially advantageous for the determination of the hydrolysis of reducing disaccharides (see e.g. Dahlqvist, A. Method for Assay of intestinal disaccharidases. ASALYTICAL BIOCHEMISTRY 7, 18-25 (1964) and Dahlqvist, A, Assay of intestinal disaccharidases, Scand J Clin Lab Invest, 44, 169-172, 1984 incorporated herein by reference) and may thus be used to measure disaccharidase activity in the methods given herein.

Assays to analyse lactase activity are known in the art and include e.g. the assay of Dahlqvist and Asp (see e.g. Dahlqvist and Asp, *Accurate assay of low intestinal lactase activity with a fluorometric method*, Analytical Biochemistry, Vol 44, pg 654-657, Dahlqvist, A. Method for Assay of intestinal disaccharidases. ASALYTICAL BIOCHEMISTRY 7, 18-25 (1964) and Dahlqvist, A, Assay of intestinal disaccharidases, Scand J Clin Lab Invest, 44, 169-172, 1984 all incorporated herein by reference) and may thus be used to measure lactase activity in the methods given herein.

Assays to analyse sucrase activity are known in the art and include the method described by Lee et al. (see e.g. Lee et al, *A method for assaying intestinal brush-border sucrase in an intact intestinal preparation*, PNAS Mar. 3, 1998 vol. 95 no. 5 2111-2116, Dahlqvist, A. Method for Assay of intestinal disaccharidases. ASALYTICAL BIOCHEMISTRY 7, 18-25 (1964) and Dahlqvist, A, Assay of intestinal disaccharidases, Scand J Clin Lab Invest, 44, 169-172, 1984 all incorporated herein by reference) and may thus be used to measure sucrase activity in the methods given herein.

Assays to analyse maltase activity are known in the art and include e.g. the assay by Dahlqvist, A. (see Assay of intestinal disaccharidases. *Scand. J. din. Lab. Invest.* 44, 169-172.1984, incorporated herein by reference) which is a modified and updated description of the author's method for the assay of intestinal disaccharidases from 1963 (supra, both incorporated herein by reference) and may thus be used to measure maltase activity in the methods given herein. In brief, an intestinal homogenate is incubated with the appropriate disaccharide, such as a maltase. The disaccharidase e.g. maltase activity is then interrupted by the addition of TRIS, and the glucose liberated is measured with a glucose oxidase reagent, and compared to standard.

Changes in intestinal enterocyte morphology in the maturation process may be changes from foetal-type intestinal enterocytes to adult type intestinal enterocytes. Said changes in morphology are thus indicative of intestinal maturation process in the methods given herein.

The function of the small intestine is the digestion of food and absorption of nutrients. The small intestine consist of three parts: the upper duodenum attached to the pyloric end of the stomach, the jejunum, and the ileum. The duodenum contains the entrances of both the pancreatic and the bile ducts, but in the rat there is only one common pancreatic-biliary duct.

The small intestine has a huge surface area formed by millions of finger-like extrusions—the villi and crypts, which are both covered by epithelial cells. In addition, the complex of specialized membrane extrusions found on the apical side of the enterocytes, the microvilli, is usually referred to as the brush border. The crypt-villus complex is considered to be the functional unit of the small intestine—see FIGS. 1a and 1b. In each intestinal crypt there is continuous cell proliferation, resulting in the production of new epithelial cells which migrate up along the villus and differentiate, simultaneously cells are shed from the top of the villi. Such complete cell replacement, called cell turnover, on the villous takes place every 2-5 days, depending on the species. In addition, in young mammals or infants, cell turnover occurs at lower rate in comparison to that in adult. There are four major types of cells making up the small intestinal mucosa, originating from the immature stem cells in the crypts: the enterocytes (absorptive cells), goblet cells (mucus-secreting), Paneth cells (secreting antibacterial peptides and enzymes) and several types of enteroendocrine cells (secreting hormones).

In neonatal rat and human infant the small intestine grows by crypt fission initiated by milk feeding, and then the cylindrical growth of the small intestine seen at weaning mostly is due to crypt hyperplasia.

During the suckling period, the immature intestine shows a high permeability for milk-borne macromolecules, hormones and other factors. The transport of macromolecules follows two pathways: specific receptor-mediated and non-specific absorption. Specific trancytosis has been reported for immunoglobulins which bind to the neonatal Fc-receptor expressed by the enterocytes in the proximal small intestine, while non-specific absorption is the pathway for the uptake of other milk proteins. The fetal-type enterocytes found universally in the distal part of small intestine contain large supranuclear vacuoles and have a high absorptive capacity for macromolecules compared to adult mature intestine. In addition, during suckling period, the intestinal mucosa expresses high activities of the brush-border enzyme lactase principally in relation to the digestion of milk components, while maltase activity is low and that of sucrase cannot be detected.

The suckling period passes gradually into the weaning period, when the intake of solid food increases and milk decreases. For rats, in the third week of life, this process is characterized by rapid growth and vast structural and functional changes in the GI tract. The crypt depth in the small intestine increases due to an increase in the cell proliferation, and the absorptive capacity of the small intestine enlarges due to epithelial hyperplasia. Important functional changes of the small intestine at this time are the increase in the mucosal brush border disaccharidase activities of maltase and sucrase with a decrease in the lactase activity. Moreover, gut permeability declines for macromolecules, resulting in intestinal "closure". The fetal phenotype enterocytes with large supranuclear "digestive" lysosomal vacuoles disappear in the distal small intestine and are replaced by the adult phenotype enterocytes.

Thus, above changes may all be used, alone or in combinations, for measurements or monitoring of the maturation process in the methods given herein.

Further, said weigh of the parts of the GI tract including the intestine, e.g. the small intestine, may be analysed in combination with the other markers of the maturation process given herein such as changes of weight of the parts of the GI tract including the intestine, e.g. the small intestine and wherein an increase of intestinal weigh is indicative of the maturation process.

Analysis of biomarkers and morphology is done in biopsies or autopsy material of a mammal. Said biopsy may be isolated from the small intestine the procedure is called a small-intestine (or small-bowel) biopsy. A larger tissue specimen may also be obtained by using an endoscope (a flexible viewing tube), or by using a thin tube with a small cutting instrument at the end. The latter procedure, using the cutting instrument, is ordered when larger specimens than those provided by endoscopic biopsy are needed, because it allows removal of tissue from areas beyond the reach of an endoscope.

As used herein a "biological sample" or "biopsy" encompasses a variety of sample types obtained from any parts of the small intestine of a mammal. A typical subject is a human infant or neonate; however, any mammal or avian species that has an intestine can serve as a source of a biological sample or biopsy. Exemplary biological samples and biopsies useful in the disclosed methods include but are not limited to biological samples disclosed herein such as e.g. solid tissue samples such as a biopsy specimen or tissue cultures or cells derived there from, and the progeny thereof. For example, biological samples include cells obtained from a tissue sample collected from an individual suspected of having an immature GI tract including the intestine, e.g. the small intestine or a mature GI tract including the intestine, e.g. the small intestine. Therefore, biological samples encompass clinical samples, cells in culture, cell supernatants, cell lysates, and tissue samples, e.g. a transrectal biopsy or endoscopic biopsy.

Several types of capsules are used for tissue collection. In each, a mercury-weighted bag is attached to one end of the capsule, while a thin polyethylene tube about 60 inches long is attached to the other end. Once the bag, capsule, and tube are in place in the small intestine, suction on the tube draws the tissue into the capsule and closes it, cutting off the piece of tissue within. This is an invasive procedure, but it causes little pain and complications are rare.

After application of a topical anesthetic to the back of the patient's throat, the capsule and the tube are introduced, and the patient is asked to swallow as the tube is advanced. The patient is then placed on the right side and the instrument tip is advanced another 20 inches or so. The tube's position is checked by fluoroscopy or by instilling air through the tube and listening with a stethoscope for air to enter the stomach.

The tube is advanced two to four inches at a time to pass the capsule through the stomach outlet (pylorus). When fluoroscopy confirms that the capsule has passed the pylorus, small samples of small intestine tissue are obtained by the instrument's cutting edge, after which the instrument and tube are withdrawn. The entire procedure may be completed in minutes.

This procedure will provide tissue specimens from the small intestine through means of a tube inserted into the stomach through the mouth. The patient is to withhold food and fluids for at least eight hours before the test.

The patient should not have anything to eat or drink until the topical anesthetic wears off (usually about one to two hours). If intravenous sedatives were administered during the procedure, the patient should not drive for the remainder of the day. Complications from this procedure are uncommon, but may occur. The patient is to note any abdominal pain or bleeding and report either immediately to the doctor.

Complications from this procedure are rare, but can include bleeding (hemorrhage), bacterial infection with fever and pain, and bowel puncture (perforation). The patient should immediately report any abdominal pain or bleeding to the physician in charge. Note: Biopsy is contraindicated in uncooperative patients, those taking aspirin or anticoagulants, and in those with uncontrolled bleeding disorders.

Tissue biopsies are then analyzed for biomarkers and morphology on gross examination of the specimen(s) or under the microscope after tissue preparation.

Further examples are small intestinal biopsies and/or autopsy tissues, or intestinal cell samples. Samples may be fresh or processed post-collection (e.g., for archiving purposes). In some examples, processed samples may be fixed (e.g., formalin-fixed) and/or wax- (e.g., paraffin-) embedded. Fixatives for mounted cell and tissue preparations are well known in the art and include, without limitation, 95% alcoholic Bouin's fixative; 95% alcohol fixative; B5 fixative, Bouin's fixative, formalin fixative, Karnovsky's fixative (glutaraldehyde), Hartman's fixative, Hollande's fixative, Orth's solution (dichromate fixative), and Zenker's fixative (see, e.g., Carson, Histotechology: A Self-Instructional Text, Chicago: ASCP Press, 1997). In some examples, the sample (or a fraction thereof) is present on a solid support.

Solid supports useful in a disclosed method need only bear the biological sample/biopsy and, optionally, but advantageously, permit convenient detection of biomarkers or morphology of interest in the sample. Exemplary supports include microscope slides (e.g., glass microscope slides or plastic microscope slides), coverslips (e.g., glass coverslips or plastic coverslips), tissue culture dishes, multi-well plates, membranes (e.g., nitrocellulose or polyvinylidene fluoride (PVDF)) or BIACORE®; chips.

Further, analysis of biomarkers, such as proteins, mRNA or enzyme activity may be determined by immunohistochemistry which includes a scoring system, such as of mRNA, protein expression or enzyme activity which may optionally be used. The scoring may be semi-quantitative; for example, with mRNA or protein expression levels recorded as 0, 1, 2, or 3 (including, in some instances plus (or minus) values at each level, e.g., 1+, 2+, 3+) with 0 being substantially no detectable mRNA or protein expression and 3 (or 3+) being the highest detected protein expression. In such methods, an increase or decrease in the corresponding protein expression is measured as a difference in the score as compared the applicable control (e.g. a standard value or a control sample); that is, a score of 3+ in a test sample as compared to a score of 0 for the control represents increased mRNA or protein expression in the test sample, and a score of 0 in a test sample as compared to a score of 3+ for the control represents decreased mRNA or protein expression in the test sample.

Immunohistochemistry (IHC) is one exemplary technique useful for detecting protein expression in the disclosed methods and uses. Antibodies (e.g., monoclonal and/or polyclonal antibodies) specific for each protein expression marker are used to detect the expression. The antibodies can be detected, as further described herein, by direct labelling of the antibodies themselves, for example, with radioactive labels, fluorescent labels, hapten labels such as, biotin, or an enzyme such as horseradish peroxidase or alkaline phosphatase. Alternatively, an indirect labelling is used where unlabeled primary antibody is used in conjunction with a labelled secondary antibody, comprising e.g. antiserum, polyclonal antiserum or a monoclonal antibody specific for the primary antibody. IHC protocols are well known in the art and are commercially available, see e.g. Antibodies: A Laboratory Manual, Harlow and Lane (Cold Spring Harbor Laboratory press, Cold Spring Harbor, N.Y. 1988) and Current Protocols in Immonology, and Current Protocols in Molecular Biology, both John Wiley and Sons, Inc., N.Y.) incorporated herein by reference.

In humans, and particularly infants and newborn of other species, it may not be suitable to use an invasive method for analysing intestinal maturation. Further, ethical constraints associated with obtaining tissue biopsies from healthy infants have forced investigators to develop non-invasive methods.

Thus, further intestinal maturation may be analysed by a non-invasive method. Said non-invasive methods may, of course, be used in any mammal such as the mammals exemplified herein or any other mammal. Further embodiments are wherein the mammal is a human, such as e.g. an adult or an infant or neonatal.

Methods for analysing intestinal maturation by non-invasive methods are known in the art and examples of such methods include the methods developed by Chapkin et al. (*Non-invasive stool-based detection of infant gastrointestinal development using gene expression profiles from exfoliated epithelial cells*, Am. J. Physiol Gastrointest Liver Physiol, 298: G582-G589, 2010, incorporated herein by reference), by Veereman-Wauters, G et al., (Journal of Pediatric Gastroenterology & Nutrition: August 1996-Volume 23-Issue 2-pp 111-117, The 13C-Octanoic Acid Breath Test: A Noninvasive Technique to Assess Gastric Emptying in Preterm Infants incorporated herein by reference, or by TRAV'ES et al. (Alcohol & Alcoholism Vol. 42, No. 5, pp. 407-412, 2007).

In brief, the method by Chapman et al. encompasses a non-invasive stool-based detection of infant gastrointestinal development using gene expression profiles from exfoliated epithelial cells. The method by Chapman is a molecular methodology whereby stool samples containing intact sloughed epithelial cells are used to quantify intestinal gene expression profiles in the developing human neonate and where particular gene sets are used as identifiers for the maturation process including structural and functional adaptation of the intestine as a response to feeding.

Exfoliated cells are isolated of its mRNA by standard procedures, e.g. directly from faeces, which contain sloughed small intestinal and colon cells, and thus, does not result in any discomfort to the subject. In brief, by using a sterile spoon about 10 g of freshly voided faecal stool specimens may be collected into a sterile 50 ml conical tube containing 20 ml of guanidinium denaturation solution (e.g. provided by AMbion, Austin, Tex.). Samples may then be mixed by hand to create a homogenous sample, which may be immediately frozen at −20° C. until transported on ice for further analysis. Samples are held at −80° C. and—if shipped or moved—on dry ice.

Poly-A mRNA may then be isolated according to any known method in the art, e.g. Davidson et al. ("*Quantification of human intestinal gene expression profiles using exfoliated colonocytes: a pilot study*", biomarkers, 8:51-61, 2003 incorporated herein by reference). Further, the integrity of the isolated mRNA may be analysed using e.g. an Agilent 2100 Bioanalyzer, and quantified using spectrophotometrical methods, e.g. by a NanoDrop, (Wilmington, Del.). Samples are then processed according to the CodeLink Gene Expression Assay manual (Applied Microarray, Temple, Ariz.), and analysed using the Human Whole Genome Expression Bioarray. Such each array contain the entire human genome derived from publicly available, well-annotated mRNA sequences. Arrays may be inspected for spot morphology. Marginal spots may be flagged as background spots (contaminated, irregularly shaped, or saturated) in the scanning software. Spots that passes the quality-control standards may, in the scanning software be categorized as good. In addition, a set L-value and reading thereof for "low" values, may indicate "near background", such as that low L-values may reflect true low gene expression levels or may have been caused by degradation of the mRNA. Further, for the purpose of normalisation, housekeeping genes may be used.

Examples of suitable genes analysed by non-invasive methods are one-, two-, and three gene sets, such as e.g. one genes: EPAS1, NR5A2, NR3C1, PCDH7, ITGB2, FGF5, TJP1, MYB, EPIM, BAD; and for two-gene sets: EPAS1 and UCP1, CTDSPL and NR3C1, NR3C1 and TNFRSF10B, FOXP4 and NR3C1, CDK4 and EPAS1, EPAS1 and SYP, NR3C1 and SLC26A2, GPR41 and TJP1, FOXP1 and NR3C1, HSPA1A and NR3C1. Further, examples of three gene sets are EPAS1, FOXE3, and SYP; CTDSPL, FOXE3 and NR3C1; EPAS1, TLR5, and UCP2; EPAS1, REG4, and UCP2; EPAS1, LIFR, and UCP2; EPAS1, NODAL, and UCP2; EPAS1, HIF3A, and UCP2; EPAS1, HOXD10, and UCP2; EPAS1, KIT, and UCP2 as well as ALOX, EPAS1, and UCP2 (see Chapkin et al., Table 2 in *Non-invasive stool-based detection of infant gastrointestinal development using gene expression profiles from exfoliated epithelial cells*, Am. J. Physiol Gastrointest Liver Physiol, 298: G582-G589, 2010, incorporated herein by reference).

The mixture of enzymes or, as in some embodiments, comprising or consisting only of one of the enzymes such as an amylase or a protease, may be administered orally, or via stomach if a tube is placed into the stomach, enterally, intraperitoneal or intravenous or any other route known in the art.

The mixture of enzymes according to the invention comprises enzymes having a pancreatic activity or action or pancreatic like action or activity. The enzyme mixture, and also in its most simple form comprising or consisting of only one of the enzymes, e.g. amylase or protease, may be used in all its embodiments in all methods and uses herein, as is evident from the appending examples and claims.

Thus, further embodiments of the enzyme mixture are wherein the mixture of enzyme comprises or consist of at least one of a protease, a lipase or an amylase. It may further comprise protease and lipase, protease and amylase or lipase and amylase, or all three enzymes together in a mixture i.e. protease, lipase and amylase.

Even further embodiments are thus wherein the enzyme mixture comprises or consist of the enzymes protease, lipase and amylase.

Commercial sources of enzyme mixtures with pancreatic activity or action, or pancreatic like activity or action, include but are not limited to, Creon® (Abbot, Inc., US).

Enzymes may also be bought separately from commercial sources, as given herein, and mixed where appropriate. The enzymes may be of eukaryotic or prokaryotic origin, or may be made by recombinant means of expressing proteins.

The pancreatic activity and pancreatic like action or activity is measured by measuring enzyme activity. Pancreatic enzymes are enzymes secreted by the panceras, the main digestive gland in our body. Pancreatic enzymes include, but are not limited to, trypsin, chymotrypsin, steapsin, carboxypeptidase, elastases, nucleases, pancreatic and amylase.

Trypsin is a protease that breaks down proteins at the basic amino acids. Chymotrypsin is a protease that breaks down proteins at the aromatic amino acids. Steapsin degrades triglycerides into fatty acids and glycerol. Carboxypeptidase is a protease that takes off the terminal acid group from a protein. Elastases are a group of enzymes that degrade the protein elastin and some other proteins. Nucleases are a group of enzymes that degrade nucleic acids, like DNAase and RNAase. Pancreatic amylase that, besides starch and glycogen, degrades most other carbohydrates. Humans lack the enzyme to digest the carbohydrate cellulose.

Thus, said mixtures may further comprise pancreatic enzymes, or, as in embodiments mentioned herein, wherein the mixture of enzyme comprises at least one of a protease, a lipase and an amylase, e.g. only a protease, only an amylase or only a lipase as well in some embodiments. Even further embodiments are wherein the enzyme mixture comprises the enzymes protease, lipase and amylase. Said enzymes may be of mammalian origin, as in Creon®, or be of any eukaryotic or prokaryotic origin, such as e.g. bacterial origin, fungal origin. If said enzymes are of prokaryotic origin, such as bacterial or fungal, they possess the same, or similar, activity as mammalian, e.g. human, pancreatic enzymes and are herein referred to as enzymes with pancreatic like activity or action. With same enzymatic activity it is to be understood that a trypsin is a protease that breaks down proteins at the basic amino acids, chymotrypsin is a protease that breaks down proteins at the aromatic amino acids, steapsin degrades triglycerides into fatty acids and glycerol, carboxypeptidase is a protease that takes off the terminal acid group from a protein, elastases are a group of enzymes that degrade the protein elastin and some other protein, nucleases are a group of enzymes that degrade nucleic acids, like DNAase and RNAase, pancreatic amylase that, besides starch and glycogen, degrades most other carbohydrates. Humans lack the enzyme to digest the carbohydrate cellulose.

Thus, further embodiments are wherein said mixture comprises enzymes with pancreatic activity or action, or pancreatic like activity or action, or, as in embodiments mentioned herein, wherein the mixture of enzyme comprises at least one of a protease, a lipase and an amylase of eukaryotic or prokaryotic origin, or any microbiological origin, bacterial, fungal, or even recombinant origin. Even further embodiments are wherein the enzyme mixture comprises the enzymes protease, lipase and amylase of eukaryotic or prokaryotic origin, or any microbiological origin, bacterial, fungal, or even recombinant origin.

Enzymes like lipase, amylase, and protease are available commercially, from e.g. Novo Nordisk A/S (DK), Sigma and Amano Enzyme, Inc., Nagoya, Japan.

Still even further embodiments are wherein the amount of enzymes is about 12 000-120 000 Ph Eur (equals USP)/kg bodyweight and day of lipase; 608-6 080 Ph Eur (38 000-380 000 USP) of protease/kg bodyweight and day, or amylase 14 458-144 580 Ph Eur (60 000-600 000 USP)/kg bodyweight and day of at least one of the enzymes. One embodiment comprises all the three enzymes, i.e. lipase, protease, and amylase.

In further embodiments, twice as much, three times as much or even four times as much are given as a daily dose of at least one of the enzymes i.e. about 25 000, 50 000, 100 000, 150 000, 200 000, 300 000, 400 000 or even 500 000 Ph Eur (equals USP)/kg bodyweight and day of lipase, 600, 1 200, 2 000, 2 500, 6 000, 12 000, 20 000, or even, 10 000 Ph Eur, e.g. 40 000, 80 000, 120 000, 160 000 US U) of protease/kg bodyweight and day, or 14 000, 28 000, 42 000, 56 000-150 000, 300 000, 450 000, or even 600 000 Ph Eur, e.g. 60 000, 120 000, 180 000, 240 000, –600 000, 1 200 000, 1 800 000, or even 2 400 000 USP) of amylase.

In each individual, dosage duration and frequency of enzyme delivery during treatment needs to be set individually. As discussed further herein, this is a routine task for someone skilled in the art.

Further, the pancreatic activity or action, or pancreatic like activity or action, may be measured by standard methods known in the art for enzyme activity of e.g. trypsin, chymotrypsin, steapsin, carboxypeptidase, elastases, nucleases, pancreatic and amylase. Examples of suitable assays are given herein. In brief, the following enzymatic assays for measuring enzyme activity may be used;

For Lipase; a Lipase Olive Oil assay may be used: The lipase samples may be assessed for activity against olive oil at pH 7.7 using slight modifications to the procedure described by Ruyssen and Lauwers. The lipase activity is determined by titrating the released fatty acids from olive oil against sodium hydroxide. The assay may be automated using a Radiometer pH-Stat titrator (Titralab™). Activity units are defined as microequivalents (mEq) of NaOH required per min to maintain a constant pH of 7.7. Fatty acids released during the assay by lipase hydrolysis of triglycerides are titrated by NaOH. The mEq of NaOH represent the mEq of fatty acid hydrogen liberated. The initial rate is equivalent to base consumption in mL/min. The specific activity ($\mu$moles/min/mg protein)=initial rate×1000× concentration of the titrant/amount of enzyme. The ratio of activity units of the Olive Oil Assay: USP assay is ca. 1.75.

The lipase activity may be determined by USP Assay for Lipase determined by titrating the released fatty acids from olive oil against sodium hydroxide as described by U.S. Pharmacopeia (Assay for lipase activity in Pancreatin, USP 24).

The lipase activity in USP units are calculated by comparison to the activity of the standard, using the lipase activity stated on the label of USP Pancreatin Lipase RS.

The activity of proteases may be determined by an USP Assay for Protease determined by using casein as a substrate as described by U.S. Pharmacopeia (Assay for protease activity in Pancreatin, USP 24). The protease activity in USP units may be calculated by comparison to the activity of the standard, using the protease activity stated on the label of USP Pancreatin Amylase and Protease RS.

The activity of amylases may be estimated using starch as substrate as described by U.S. Pharmacopeia (Assay for amylase activity in Pancreatin, USP 24). The amylase activity in USP units was calculated by comparison to the activity of the standard, using the amylase activity stated on the label of USP Pancreatin Amylase and Protease RS.

Development and maturation of the GI tract and related organs is different between species during the fetal period. It mostly depends on the gestational period. If a species has a longer gestational period, they have a more mature GI tract at the birth. Several research groups have been investigating the different steps of maturation in different mammals like, mice, rats, guinea pigs and pigs. They have shown that despite these differences, the main steps of development of the GI tract are common among mammalian an non-mammalian, such as avian, species. The main development of GI takes place in five main different steps; morphogenical changes, cytodifferentiation, birth/early suckling, suckling and weaning. Morphogenesis and cytodifferentiation changes take place during the gestation period and lead to structural and functional changes in the intestinal epithelium. Birth suckling is the time that infant is transferred from the intrauterine (amniotic liquid) to the extra uterine environment. In the suckling period the infant starts to use maternal milk as the only source of nutrition. During the weaning period, replacement of milk (high fat and low carbohydrate diet) with solid food (low fat and high carbohydrate diet) occurs. Protein level before and after weaning is in principle the same. Genetic background, body size, age, hormones secreted from intestine and other parts of the body (i.e. insulin, corticoesterone) and also milk-born hormones and as endogenous factors and diet, microflora as exogenous sources are the main factors that affect GI tract development during the postnatal period.

Rats are well studied in their development and for many studies could be used as a model. In rat pups, the main changes in the GI tract are visible after 3 weeks of life. These changes include morphological changes, epithelial cell kinetic changes, mucosal enzyme activity and transport function changes. Increase in the number of chief cells and decrease in the number of parietal cells are signs of maturation in the stomach. Increase in the number of chief cells makes the glandular part of stomach thicker (the mucosal epithelium is thinner during early age). The secretion of pepsin, after a few days of the birth is 1.5 times higher than in adults. The pH of the stomach is higher in the neonates compared to that in the adults and decreases with time. Gastrin levels are low till day 18. As in rat pups, the stomach does not secrete pepsin so the milk proteins are not broken down but are absorbed directly from the intestine intact.

In rats at day 15 of age, the weight of the GI increases due to extension of villi and crypt cells proliferation. Formation of crypts in species with shorter gestational period is slower than in those with longer gestational period. In rodents, the visible cell proliferation of crypts, takes place after the suckling period. During the postnatal period before weaning, formation of crypts is slow, while after weaning, proliferation and migration of the cells in the crypts increases.

The proliferation of stem cells takes place at the base part of the crypts. After division, one of the daughter cells is still stem cell, while another go through differentiation to become enterocytes, enteroendocrine cells, goblet or paneth cell. All of new cells, excluding Paneth cells migrate upward toward the villi. Enterocyte cells divide a few more times along the villi and change to become absorptive cells. Vacuolated fetal type enterocytes (VFE) are created in the distal part of the small intestine and then diffuse to the lower part into the jejunum and ileum. VFEs are located along the villi (mostly on the tip of the villi) and have two main functions. These cells transfer colostral and milk protein from the lumen of the intestine into the circulation and also have a digestive function. VFEs in the duodenum exist only during birth time. In the proximal part of the jejunum they remain for 3 or 4 days and then disappear. In the middle and distal section of the jejunum VFEs stay longer, until 14 days of age, and then fade away. During the weaning period, VFEs disappear from jejunum and ileum. The mature enterocytes have no large supranuclear vacuoles and have different pattern in function.

The main carbohydrate during the suckling is lactose but in the weaning period the diet changes to a rich source of sucrose and maltose. To break down disaccharides into absorbable monosaccharides, brush-border disaccharidases (lactase, maltase, and sucrase in respective periods) are required. While maturation is happening, the activity and secretion of brush border enzymes changes such that the secretion of lactase decreases and the activity of maltase and sucrase increased.

Studies in rats have shown that postponing the weaning period and extending the suckling period may delay the decrease in lactase activity but does not affect the elevation of sucrase and maltase activity.

Many of the mammalian neonates have permeable intestine for macromolecules during first days of life (i.e. rat pups has open intestine up to 20 days after birth). It means that macromolecules can be absorbed intact to the general circulation via specific FcRn receptor, e.g. maternal IgG, or unspecificaly, e.g. epidermal growth factor. Decreasing of intestinal permeability for macromolecules is one of several markers for intestinal maturation during development.

As mentioned above, many factors are responsible for maturation of GI tract and studying of GI regulation is very important issue for developing the treatment for neonates having immature gut, i.e. human preterm born babies. Neonatal immaturity and, as a result, dysfunction of GI tract is a big problem for Neonatal Intensive Care Unit because of Necrotizing enterocolitis (NEC) syndrome. NEC is mostly developing in premature infants 75-95% and has a high mortality (around 30%). The inventors along with colleagues have demonstrated that GI maturation can be induced precociously by feeding young suckling rats and pigs to the PHA, lectin from red kidney beans.

Moreover, data included herein demonstrates that exogenous enzyme preparation with pancreatic like activities, e.g. Creon and microbial enzymes preparation showed a positive and promoting effects on gut maturation and development. This phenomenon is probably possible since animals during suckling period produce a lot of endogenous enzyme inhibitors, thus effect of enzymes can be limited. The trypsin inhibitors are probably most important since active trypsin is activator of all other pro-enzymes. To further investigate this aspect three experimental sets were designed and performed in suckling rat model.

The maturation process depends on species and other factors. Normally, the process of maturation after induction takes 1-10 days, such as 1, 2, 3, 4, 5, 6, 7, 8, 9, or even 10 days.

In one embodiment, it takes about 3-10 days, in another embodiment 3-9, 3-8, 3-7, 3-6, 3-5 or 3-4 days, or 3, 4, 5, 6, 7, 8, 9, or 10 days. In one embodiment, the maturation process takes about 3 days.

Use of a Mixture of Enzymes

A further aspect of the invention is the use of a mixture of enzymes having pancreatic activity or action, or pancreatic like activity or action, to induce maturation of an immature GI tract including the intestine, e.g. the small intestine.

Said uses are wherein the immature GI tract including the intestine, e.g. the small intestine is of a new-born infant of a mammal, such as exemplified herein, e.g. a human, rat or pig, or, a human infant such as a new-born human infant. It may also be an immature GI-tract of a non-mammal, such as from an avian species e.g. a chicken, broiler, turkey or hen.

Ways of measuring maturation of the GI tract including the intestine, e.g. the small intestine, are given herein as well as examples of enzyme mixtures. The enzyme mix may, depending on circumstances, comprise at least one of the enzymes with pancreatic activity or action, or pancreatic like activity or action, e.g. at least one of a protease, a lipase of an amylase. Said mixtures may also be of a lipase or an amylase or a protease, or a protease and a lipase, or a protease and an amylase, or a lipase and an amylase, or a protease, an amylase and a lipase. Thus, in further embodiments, said enzyme mixture comprises at least two enzymes, such as a protease and a lipase; a protease and an amylase; a lipase and amylase. In still further embodiments, the enzyme mixture according to the invention comprises three enzymes, such as a protease, an amylase and a lipase. In one embodiment, it is only a protease of the above enzymes in said mixture.

Thus, further aspects of the invention encompass a mixture of enzymes having pancreatic activity or action, or pancreatic like activity or action, for inducing maturation of an immature GI tract including the intestine, e.g. the small intestine, in a mammal or avian species, as exemplified herein, e.g. in a human newborn.

A further aspect of the invention is a mixture of enzymes having pancreatic activity or action, or pancreatic like activity or action, for treatment of an immature GI-tract disorder, e.g. intestinal disorder, such as a small intestinal disorder.

Further embodiments are wherein said immature GI-tract disorder, e.g. intestinal disorder, such as a small intestinal disorder is necrotizing enterocolitis. Necrotizing enterocolitis (NEC) is a medical condition primarily seen in premature infants where portions of the bowel undergo necrosis (tissue death). The condition is typically seen in premature infants, and the timing of its onset is generally inversely proportional to the gestational age of the baby at birth, i.e. the earlier a baby is born, the later signs of NEC are typically seen. Initial symptoms include feeding intolerance, increased gastric residuals, abdominal distension and bloody stools. Symptoms may progress rapidly to abdominal discoloration with intestinal perforation and peritonitis and systemic hypotension requiring intensive medical support.

Even further aspects of the invention are use of a mixture of enzymes having pancreatic activity or action, or pancreatic like activity or action, for the preparation of a medicament for treatment of an immature GI-tract disorder, e.g. intestinal disorder, such as a small intestinal disorder, e.g. wherein said immature GI-tract disorder, e.g. intestinal disorder, such as a small intestinal disorder is necrotizing enterocolitis.

Thus, one further aspect is a method of treating an individual or subject or patient, all of which may be a newborn, with an immature GI-tract disorder, e.g. intestinal disorder, such as a small intestinal disorder, said method comprising the steps of administering to a patient in the need thereof an effective amount of a mixture of enzymes with pancreatic activity or action, or pancreatic like activity or action, to induce GI-tract, e.g. intestinal, such as a small intestinal maturation, e.g., wherein said disorder of an immature GI-tract, e.g. intestinal, such as a small intestinal, is necrotizing enterocolitis.

Thus, as mentioned throughout the application, further embodiments are wherein said subject, individual or patient in the need thereof is an infant, such as a newborn.

A further aspect of the invention provides a pharmaceutical composition comprising an enzyme mixture with pancreatic activity or action, or pancreatic like activity or action, as disclosed herein and a pharmaceutically acceptable excipient, diluent or carrier. As used herein, "pharmaceutical composition" means a therapeutically effective formulation.

A "therapeutically effective amount", or "effective amount", or "therapeutically effective", as used herein, refers to that amount which provides a therapeutic effect for a given condition and administration regimen; for example, an amount sufficient to induce maturation of the GI tract including the intestine, e.g. the small intestine. This is a predetermined quantity of active material calculated to produce a desired therapeutic effect in association with the required additive and diluent, i.e. a carrier or administration vehicle. Further, it is intended to mean an amount sufficient to reduce or prevent a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent.

In the methods, uses, kits and for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

It will be appreciated by persons skilled in the art that such an effective amount of the enzyme mixture with pancreatic activity or action, or pancreatic like activity or action, or formulation thereof may be delivered as a single bolus dose (i.e. acute administration) or, more preferably, as a series of doses over time (i.e. chronic administration).

It will be further appreciated by persons skilled in the art that the enzyme mixture with pancreatic activity or action, or pancreatic like activity or action, for use in the methods, kits and uses of the invention may be administered in combination with one or more other conventional agents for the treatment of immature gastrointestinal tract, e.g. intestine, such as small intestine.

For example, suitable conventional agents include, but are not limited to, PHA, and/or IL2.

The enzyme mixture with pancreatic activity or action, or pancreatic like activity or action, according to the invention may be formulated at various concentrations, depending on the efficacy and toxicity. In further embodiments the amount of enzymes is about 12 000-120 000 Ph Eur (equals US U)/kg bodyweight and day of lipase, 608-6 080 Ph Eur (38 000-380 000 US U) of protease/kg bodyweight and day or amylase 14 458-144 580 Ph Eur (60 000-600 000 Us U)/kg bodyweight and day of at least one of the enzymes, i.e. a protease, or an amylase or a lipase. In one embodiment, it is only a protease. One embodiment comprises all the three enzymes, i.e. lipase, protease, and amylase. Further embodiments comprise at least two of the enzymes, such as a protease and a lipase, or a protease and an amylase, and an amylase and a lipase.

In even further embodiments, twice as much, three times as much or even four times as much are given as a daily dose of at least one of the enzymes i.e. about 25 000, 50 000, 100 000, 150 000, 200 000, 300 000, 400 000 or even 500 000 Ph Eur (equals US U)/kg bodyweight and day of lipase, 600, 1 200, 2 000, 2 500, 6 000, 12 000, 20 000, or even, 10 000 Ph Eur, e.g. 40 000, 80 000, 120 000, 160 000 US U) of protease/kg bodyweight and day, or 14 000, 28 000, 42 000, 56 000-150 000, 300 000, 450 000, or even 600 000 Ph Eur, e.g. 60 000, 120 000, 180 000, 240 000, –600 000, 1 200 000, 1 800 000, or even 2 400 000 US U) of amylase.

For in vitro applications, formulations may comprise a lower concentration of a compound of the invention.

Thus, there is provided a pharmaceutical formulation comprising an amount of enzyme mixture with pancreatic activity or action, or pancreatic like activity or action, effective to treat a condition of an immature GI tract including the intestine, e.g. the small intestine, e.g. NEC (as described above).

It will be appreciated by persons skilled in the art that the medicaments and agents will generally be administered in admixture with a suitable pharmaceutical excipient, diluent or carrier selected with regard to the intended route of administration and standard pharmaceutical practice (for example, see Remington: The Science and Practice of Phamtacy, 19 edit ion, 1995, Ed. Alfonso Gennaro, Mack Publishing Company, Pennsylvania, USA, which is incorporated herein by reference.

For example, the medicaments and agents can be administered orally, buccally or sublingually in the form of tablets, capsules, ovules, elixirs, solutions or suspensions, which may contain flavouring or colouring agents, for immediate-, delayed- or controlled-release applications. The medicaments and agents may also be administered via intracavernosal injection.

Tablets may contain excipients such as microcrystalline cellulose, lactose, sodium citrate, calcium carbonate, dibasic calcium phosphate and glycine, disintegrants such as starch (for example, corn, potato or tapioca starch), sodium starch glycollate, croscarmellose sodium and certain complex silicates, and granulation binders such as polyvinylpyrrolidone, hydroxypropylmethylcellulose (HPMC), hydroxy-propylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Exemplary excipients in this regard include lactose, starch, cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The medicaments and agents can also be administered parenterally, for example, intravenously, intra-articularly, intra-arterially, intraperitoneally, intrathecally, intraventricularly, intrasternally, intracranially, intra-muscularly or subcutaneously, or they may be administered by infusion techques. They are best used in the form of a sterile aqueous solution which may contain other substances, for example, enough salts or glucose to make the solution isotonic with blood. The aqueous solutions should be suitably buffered (for example, to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and nonaqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the medicaments and agents will usually be as exemplified herein administered in single or divided doses.

It is appreciated that for the prevention or treatment of disease, the appropriate dosage of an enzyme mixture with pancreatic activity or action, or pancreatic like activity or action, will depend on the type of disease to be treated, the severity and of course of the disease, whether the enzyme mixture with pancreatic activity or action, or pancreatic like activity or action, is administered for preventative or therapeutic purposes, the course of previous therapy and the patient's clinical history and response to the enzyme mixture with pancreatic activity or action, or pancreatic like activity or action according to the present invention is suitably administered to the patient at one time or over a series of treatments depending on the type and severity of the disease. Administration may be, for example, by one or more separate administrations, or by continuous infusion.

For repeated administrations over several days or longer, depending on the condition, the treatment is repeated until a desired suppression or alleviation of the disease symptoms occurs, and a desired GI-tract, e.g. intestinal, such as a small intestinal, maturation. However, other dosage regimens may be useful and are not excluded. The effectiveness of enzyme mixture with pancreatic activity or action, or pancreatic like activity or action, in alleviating the symptoms, preventing or treating disease may be improved by serial administering or administration in combination with another agent that is effective for the same clinical indication, such as another enzyme, or one or more conventional therapeutic agents known for the intended therapeutic indication, or any other substance with effect such as i.e. PHA or IL2.

The enzyme mixture, medicaments and agents can also be administered intranasal or by inhalation and are conveniently delivered in the form of a dry powder inhaler or an aerosol spray presentation from a pressurized container, pump, spray or nebuliser with the use of a suitable propellant, e.g. dichlorodifluoromethane, trichlorofluoro-methane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations may be arranged so that each metered dose or puff contains at least 1 mg of a compound of the invention for delivery to the patient. It will be appreciated that the overall daily dose with an aerosol will vary from patient to patient, and may be administered in a single dose or, more usually, in divided doses throughout the day.

It may be preferable to use a sustained-release drug delivery system, such as a microsphere. These are designed specifically to reduce the frequency of injections. An example of such a system is Nutropin Depot which encapsulates recombinant human growth hormone (rhGH) in biodegradable microspheres that, once injected, release rhGH slowly over a sustained period. This system may thus be useful as a slow release for delivering at least one enzyme composition according to the invention, alone or in a mixture. Sustained-release enzyme compositions also include liposomally entrapped enzymes. Liposomes containing the enzymes are prepared by methods known per se. See, for example Epstein et al., Proc. Natl. Acad. Sci. USA S2:3688-92 (1985); Hwang et al., Proc. Natl. Acad. Sci. USA 77: 4030-4 (1980); U.S. Pat. Nos. 4,485,045; 4,544, 545; 6,139,869; and 6,027,726, which are incorporated herein by reference. Ordinarily, the liposomes are of the small (about 200 to about 800 Angstroms), unilamellar type in which the lipid content is greater than about 30 mole percent (mol. %) cholesterol; the selected proportion being adjusted for the optimal enzyme therapy.

Alternatively, polypeptide medicaments and agents can be administered by a surgically implanted device that releases the drug directly to the required site.

An alternative method of enzyme delivery is the thermosensitive ReGel injectable. Below body temperature, ReGel is an injectable liquid while at body temperature it immediately forms a gel reservoir that slowly erodes and dissolves into known, safe, biodegradable polymers or enzyme. The active drug or enzyme is delivered over time as the biopolymers dissolve.

Enzyme mixture with pancreatic activity or action, or pancreatic like activity or action as described herein in all its embodiments, can also be delivered orally. Such a system employs a natural process for oral uptake.

A Kit

Further aspects of the invention encompass a kit for inducing maturation of a GI tract including the intestine and accessory organs, e.g. the small intestine and pancreas, or being a kit to improve body weight gain, said kit comprising a) a mixture of enzymes with pancreatic activity or action, or pancreatic like activity or action, to induce GI tract maturation, e.g. intestinal maturation, or to improve body weight gain b) instructions to induce GI tract, e.g. intestinal, maturation according to any of the methods described herein or to improve body weight gain.

The enzyme mixture is described further herein and all its embodiments may be used in the kit format. In some embodiments, a kit includes positive or negative controls and control samples, such as a cell line or tissue known to be mature or immature samples or tissues of intestine of species to be analysed, such as a mammal, e.g. a human new-born, or an avian species such as a bird, e.g. a turkey, duck, hen, chicken or broiler thereof.

In some embodiments, a kit includes instructional materials disclosing, for example, means of use of the enzyme mixture with pancreatic activity or action, or pancreatic like activity or action, for induction of GI-tract, e.g. intestinal, such as a small intestinal maturation according to the detection means, or means of use for a particular reagent. The instructional materials may be written, in an electronic form (e.g., computer diskette or compact disk) or may be visual (e.g., video files). The kits may also include additional components to facilitate the particular application for which the kit is designed. Thus, for example, the kit can include buffers and other reagents routinely used for the practice of a particular disclosed method. Such kits and appropriate contents are well known to those of skill in the art.

The kit may further comprise, in an amount sufficient for at least one assay, the enzyme mixture described herein to as a separately packaged reagent, as well as separate instructions for its use to induce GI-tract, e.g. intestinal, such as a small intestinal, maturation.

Instructions for use of the packaged reagent are also typically included. Such instructions typically include a tangible expression describing reagent concentrations and/or at least one assay method parameter such as the relative amounts of reagent and sample to be mixed, maintenance time periods for reagent/sample admixtures, temperature, buffer conditions and the like.

Certain kit embodiments can include a carrier means, such as a box, a bag, a satchel, plastic carton (such as moulded plastic or other clear packaging), wrapper (such as, a sealed or sealable plastic, paper, or metallic wrapper), or other container.

In some examples, kit components will be enclosed in a single packaging unit, such as a box or other container, which packaging unit may have compartments into which one or more components of the kit can be placed. In other examples, a kit includes a one or more containers, for instance vials, tubes, and the like that can retain, for example, one or more biological samples to be tested.

Other kit embodiments include, for instance, syringes, cotton swabs, or latex gloves, which may be useful for handling, collecting and/or processing a biological sample. Kits may also optionally contain implements useful for moving a biological sample from one location to another, including, for example, droppers, syringes, and the like. Still other kit embodiments may include disposal means for discarding used or no longer needed items (such as subject samples, etc.). Such disposal means can include, without limitation, containers that are capable of containing leakage from discarded materials, such as plastic, metal or other impermeable bags, boxes or containers.

Anti-Aging Effect

Enzyme mixture with pancreatic activity or action, or pancreatic like activity or action in all its embodiments described herein may according to the invention also be used to feed an elderly population of most species, e.g. subjects defined herein, to prevent or limit aging of the gastro-intestinal tract. The present invention thus provides an enzyme mixture with pancreatic activity or action, or pancreatic like activity or action for use in preventing, postponing, limiting, reducing aging of the GI-tract in a subject. It may thus further be used for treating aging as an anti-aging composition or mixture. As used herein, an anti-aging effect means to postpone, limit, reduce, reverse or even prevent aging of the GI-tract.

Aging of the GI-tract is often seen as impaired absorption of molecules from the GI-tract, resulting in loss of body weight, reduced exocrine pancreatic function, morphological changes of vili, mucosa, crypt depth, reduction in intestinal disaccharidase, increased permeability for macromolecules. This will result in a malnutrition, maldigestion and malabsorption of the elderly subject which may result in a shortening of life and have negative impact on age-related sicknesses, e.g. osteroporosis, sarcopeny, muscle fatigue, cholesteremia, etc.

Thus, the enzyme mixtures described herein in all its embodiments may be used in an anti-aging composition or formulation as f.ex. a food, a feed supplement or a medicament for preventing aging of the GI-tract, or preventing gut involution, disorders and disfunctions of elderly.

Further examples are as described in grater details elsewhere herein are wherein the mixture of enzyme comprises at least one of protease, lipase and amylase. It may further comprise protease and lipase, protease and amylase or lipase and amylase, or all three enzymes together in a mixture i.e. protease, lipase and amylase.

Thus, the enzyme mixture described herein, in all its embodiments, may be used for the manufacture of a medicament, food- or feed-supplement for treating or preventing aging of the GI-tract.

The enzyme mixture provided herein may further be used in postpone, limit, reduce, reverse or even prevent aging of the GI-tract, or to prevent gut involution, disorders and disfunctions.

The enzyme mixture provided herein may further be used in a specific embodiment comprising amylase. Amylase stimulates growth, i.e. improvement of body weight gain, as seen in e.g. FIG. 11, but less or no maturation. Proteases, however are excellent stimulators of maturation of the GI-tract, but stimulates growth or improvement of body weight gain less (see e.g. FIGS. 7 and 4). Thus, one aspect of the invention provides a mixture of enzymes comprising amylase to stimulate growth, i.e. increase in body weight or improvement of body weight gain.

A further aspect provides a mixture of enzymes comprising both an amylase and a protease, as described in further embodiments herein, stimulating both growth, i.e. gain in body weight or improvement of body weight gain as well as maturation of an immature GI-tract, or even preventing gut involution, disorders and disfunction of a GI-tract of an elderly subject.

Thus, in further aspects of the invention a use of a mixture of enzymes having pancreatic activity or action, and/or pancreatic like activity or action to induce an increase in body-weight or improve body weight gain in a subject.

Further aspects are use of a mixture of enzymes having pancreatic activity or action, and/or pancreatic like activity or action for the preparation of a medicament for increasing body-weight or improving body weight gain in a subject.

Thus, the uses to increase or improve body-weight gain, both as a medicament and as a use, are wherein the mixture of enzymes having pancreatic activity or action, and/or pancreatic like activity are according to any of the embodiments of the enzyme mixtures as described herein. Particularly, for the use to increase bodyweight, are wherein mixture of enzyme comprises or consists of amylase. Examples of doses of amylase and other enzymes are mentioned elsewhere herein and may also be used for improving body weight gain.

Any composition, mixture or formulation mentioned herein in all its embodiments may be used together with an acceptable carrier and/or diluent, which may be pharmaceutically acceptable, salts and other nutrients if appropriate.

Non-limiting examples which embody certain aspects of the invention will now be described.

EXAMPLES

Below are experiments and examples shown. The first one involved set of three enzyme which had pancreatic-like actions (Creon), and the remaining one was free from pancreatic-like action (Rovabio), introduced in two doses by intragastric gavage to 14 days old suckling rats model. Rovabio™, e.g. Rovabio™ Excel AP, is a concentrated powder whose main enzymatic activities are xylanase and β-glucanase obtained from a fermentation broth of *Penicillium funiculosum*. Rovabio™ Excel AP product hydrolyses pentosans and β-glucans in vegetable raw materials. Thus, Rovabio™ does not possess any pancreatic or pancreatic like activity.

Assays for measuring endo-1,4-β-xylanase activity are based on the enzymatic hydrolysis of a standard wheat arabinoxylan solution, the activity being determined by the reduction in relative viscosity (viscometer developed by Orange Leaf Company), or by measuring absorbance at 590 nm that enables endo-1,4-β-xylanase activity to be determined by a colorimetric method with a chromophore substratum.

Assays for endo-1,3(4)-β-glucanase activity includes measuring absorbance at 590 nm that enables endo-1,3(4)-β-glucanase activity to be determined by a colorimetric method with a chromophore substratum.

Assays for cellulase (endo 1,4-β-glucanase) activity include the reaction, catalysed by cellulase, involving the endohydrolysis of the 1,4-β-D-glucosidic bonds in cellulose (lichenin and cereal β-D-glucans) forming β-1,4 glucan oligosaccharides. Assays are available form e.g. Adisseo (France).

In the second experiment we studied the link between inflammation cascades and intestine maturation by blocking cyclooxygenase pathway using Ibuprofen and Celecoxib, administered orally one hour prior to introduce of the enzymes. In both experiments there was particular emphasis on morphological and functional changes as parameters.

The results showed only Creon have increased the weight of intestine, sucrase and maltase activity, and the ratio of adult phenotype along the villi with significant values. Also the responses of the immune system to each one was various. However, small single dose of anti-inflammatory drug could not block maturation; instead it left very mild effect on enterocyte development.

Our results demonstrates that a mix of pancreatic enzyme participate in the gut maturation. Furthermore this maturation could be T-cell independent as with Creon. On the other hand, the maturation was slightly inhibited with Celocoxib, suggesting that the clooxgynase pathway maybe involved in the mechanism(s) that induced maturation in this model, if it blocked in precise way.

Previous published data about precocious maturation in pre-weaning rats, showed the maturation of gut was always consistent with increasing the weight of organs like the intestine and pancreas furthermore the morphological and functional changes in the enterocytes of intestine. The examples below study the effect of the following enzyme mixes: Creon® and Rovabio® on gut development, we found that only Creon®—which have pancreatic like activity—shown effect on intestine maturation, moreover these effects were dose-related.

Similarly to organ weight, Creon® have shown some effects on disaccharidases activities, as there was significant increase in sucrase and maltase activity, while these changes were not observed in the case of Rovabio®.

The higher sucrase and maltase expression in the intestine of rats indicates the presence of a higher number of mature enterocytes in it. The results revealed that only the intestine which gave high sucrase and maltase activity, expressed high levels of matured entrocytes, so only Creon® induced expressions of new mature enterocytes.

By comparing the effect of Creon® (animal origin) on intestine specifically, it seems that Creon® was potent.

However, nonpancreatic like enzyme preparation (Rovabio®) yielded no effects on intestine weight, disaccharide-sases nor on the development of enterocytes to mature phenotypes, supporting the ability or possibility of pancreatic enzymes to induce maturation which is safer than other materials like PHA, opening a door for a new generation of therapies for treatment of immature intestine.

Although the effects of Creon® on the digestive system are similar, responses of the immune system to each differs. There were slightly decreased and increased immune cell expansions with Creon®. It was noted that both CD25 and CD45 marker shrunk and expanded together within both enzymes.

This variation could be explained in two ways depending on the location of the material, if it was in the lumen or in L.P. In studies performed in the 1930s, pancreatic enzymes were shown to be quite effective in preventing food allergies, due to its roles in food digestion and the breaking up of food antigens into small fragments, preventing sensitivity of intestinal epithelial cells to many intact antigens, furthermore, individuals who do not produce enough pancreatic enzymes will typically suffer from multiple allergies and, and for this reason pancreatic enzymes have been used as anti-inflammatory materials. Thus both Creon® can decrease the sensitivity of cell to luminal antigens which could be decreased some inflammatory mediators leading to decrease of immune cells in LP later on, as with Creon®.

Both of the anti-inflammatory drugs Celocoxib® (selective COX2 blocker) and Ibuprofen (nonseletive blocker of COX2 and COX1) did not abolish the effects of Creon® on the intestine. However, the effect of Creon® did slightly decrease in the presence of Celocoxib® but not with Ibuprofen®. Those pups which were pretreated with Celocoxib® showed a decrease in sucrase and maltase activity, and a decrease in the adult phenotype ratio along the villi as compared with the Creon® group. These findings indicate some signs of a delay in gut maturation in the Celocoxib® pretreated group.

In spite of both Ibuprofen® and Celocoxib® having the same mechanism of action the outcomes was dissimilar, this distinctive effect may be related to the half life which is 2 hr, and 12 hr for Ibuprofen® and Celocoxib® respectively or may be due to different targets for each drug.

However, the reason why there was little action with Celocoxib® could be due to its dose, which was the minimum allowed dose administered once daily while the recommended dose (loaded dose) was four times more than what was used, and administered twice daily.

Since no significant data was noticed in groups which were pretreated with drugs and fed with Creon® as compared with the group fed with Creon® only, the full answer for roles of inflammatory mediators is still vague. Moreover, we do not consider other factors like, other inflammatory pathways which cannot be blocked by nonsteroidal anti-inflammatory drugs [NSAIDs], severity and duration of COX expression.

The results below demonstrates that enzymes with pancreatic like activity or action participates in the signalling pathways involved in the gut maturation. Interestingly, the importance of T-cell expansion not being observed in Creon®-induced maturation in preweaning rats suggests that the gut maturation could be T-cell independent.

Materials and Methods for Example 1 and 2.
Animal Model:

This study was performed on rats (*Rattus norvegicus*) of Sprague-Dawley stock (Mol: SPRD Han; Taconic M&B A/S, Ry, Denmark) conventionally bred in the Departmental animal unit in a controlled environment with a temperature of about 20±1° C., with a relative humidity of 50±10% and a dark-light cycle of 12:12 h. Dams with their litters housed individually in a polycarbonate cage on chopped aspen wood bedding with free access to water and chow from a lid feed hoper.

Experimental Procedures:

In both of the following experiments 14-d-old pups were weighed and divided into groups and further to subgroups depending on the aim of each experiment. Pups were fed intragastrically via a feeding tube (0.96 mm outer diameter, PE50, Becton Dickinson, Sparks, Md., USA), in a volume 0.01 mL/g b.wt. The dose(s) for each pup was repeated once daily in corresponding manner for three days (14, 15, 16-d-old).

At 17 days of age, all the pups were separated from their dams and then anesthetized by a subcutaneous injection of a mixture of Azaperone® (Stresnil; Janssen Pharmaceutica, Beerse, Belgium), 30 µg/g body weight (b.wt), and Ketamine® (Ketalar; Pfizer, New York, N.Y., USA), 170 µg/g b.wt. Once sure of anesthesia, the abdomen and thorax were then opened, euthanized via heart puncture. The small intestine was, after it was dissected out, length measured and then divided into two equally long proximal and distal parts, both of which were flashed with cold saline followed by a measurement of each one's weight. A 2 cm piece was collected from the midsection of the distal part and fixed in bouin's solution for 24 hr at room temperature for morphological changes measurements, while the rest parts of it were immediately frozen on dry ice and stored for functional analysis.

Assay of Disaccharidases:

The distal part of the small intestine was homogenized in cold 0.9% NaCl (1:10 w/v). Then, the disaccharidase activities were measured by the Dahlqvist A method, by incubating the homogenates with the appropriate disaccharide for 1 h at 37° C., thereafter the liberated glucose was measured by using a glucose oxidase reagent (Sigma chemicals), as described in Dahlqvist, A, in 1984 (Assay of intestinal disaccharidases, Scand J Clin Lab Invest, 1984; 44: 169-172).

Protein Estimation:

The protein contents were determined by the method of Lowry et al (Lowry O H, Rosebrough N J, Farr A L & Randall R J Protein measurement with the Folin phenol reagent, *J Biol Chem*; 1951:193, 265-275.), modified for 96-well microplates as described in Pierzynowsk et al (Pierzynowsk S G, Westrom B R, Svendsen J & Karlsson B W. Development of exocrine pancreas function in chronically cannulated pigs during 1-13 weeks of postnatal life. *J Pediatr Gastroenterol Nutr* 1990; 10:206-212), and using serial dilutions of BSA (Sigma chemicals) as a standard.

Histology and Morphomertry:

All the samples from the distal SI were embedded into paraffin, cut laterally into 5 mm thick sections, deparaffinated, and stained with hematoxylin and eosin according to standard procedures. All the samples were then imaged by using an Olympus PROVIS microscope (objective ×10) utilizing an Olympus DP50 camera (Olympus, Tokyo, Japan). Morphomertic analysis by measuring the ratio of the length of the adult-like epithelium to whole villi length was done by using ImageJ 1.36 program (National Institute of Health, Bethesda, Md.).

Immunohistochemistry (Staining of Immune Cells):

All samples from distal part were embedded, cut, deparaffinated, followed by incubation in PBS pH 7.2 containing 0.5% peroxidise, washed in PBS (pH 7.2), and incubated overnight at 4° C. with specific primary Abs. It was rabbit polyclonal Ab against rat CD45 (diluted 1:50) and mouse Ab against rat CD25 (diluted in 1:50), markers expressed on all leukocytes and effector T cells respectively (3).

The next day, the samples were washed in PBS followed by incubation for two hours at room temperature with secondary Abs (antibodies) conjugated with horseradish peroxidase, it was anti rabbit (diluted 1:1400) and anti mouse Abs (diluted 1:1000) for CD45 Ab and CD25 Ab respectively. To visualize the targets of CD45 and CD25, complex of 3,3-diaminobenzidine tetrahydrochloride (Sigma Chemicals) was used as the substrate. Before mounting, all the samples were counterstained with haematoxylin. Thereafter, different images for treated and control group were viewed, using the same microscope and same program which were prescribed, followed by calculating numbers of CD45 and CD25 per cubic millimeter.

Calculations and Statistics

In order to compensate for individual variations in BW, the organ measurements are presented per g BW. All data are presented as mean values and standard deviations. Statistical comparisons between all groups were carried out using a one-way ANOVA analysis (SigmaStat 2.0; Jandel Scientific, San Rafael, Calif., USA) with all pairwise multiple-comparison procedures (Student Newman-Keuls method). Differences were considered to be significant when $P<0.05$.

Example 1

The $1^{st}$ experiment involved three litters (n=34), each litter receiving one enzyme mix as explained below. The pups in each litter were divided into three groups: One group received a dose of one enzyme mix (see below) and was referred to as high dose, while the second group received a dose five times lower than the first group and was referred to as low dose while the last group received DW (distilled water) and this group is referred to as control.

The first group fed with Creon® (Abbotte, Germany) in doses of 1.5 and 0.3 mg/g b.wt (body weight) for high and low dose respectively, diluted in a DW with final volume of 0.01 mL/g b.wt for both. The second group were treated with Rovabio (Adisseo, France) respectively. In both cases, the dose was 0.5 and 0.1 mg/g b.wt for high and low doses respectively, diluted in DW giving final volume of 0.01 mL/g b.wt for both. The third group was treated with microbial-derived enzyme mixture in high dose 0.7 mg/g b.wt. and low dose as 0.14 mg/g b.wt., in volume 0.01 mL/g b.wt. The control group of the above litters received the same volume of DW (0.01 mL/g b.wt).

Each enzyme preparation contains such composition of enzymes with corresponding activities: 150 mg of Creon capsule (lipase 10 000 USP, potease 37 500 USP, amylase 33 200 USP); 100 mg of microbial enzyme mixture powder (lipase 17 600 USP, protease 12 500 USP, amylase 1 875 USP) and for 1 g of Rovabio Exel AP(endo-1,4-beta-xylanase 22 000 visco units and endo-1,3(4)-beta-glucanase 2 000 AGL units (explanation: 1 visco unit of endo-1,4-β-xylanase is defined as the amount of enzyme which will hydrolyze the substrate, reducing the viscosity of the solution, to give a change in relative fluidity of 1 (dimensionless) unit/mn/g of enzyme under the conditions of the assay (viscometer developed by Orange Leaf company); 1 AGL unit is defined as the release of oligomers from a chromophore-bound glucan which are not precipitable by ethanol, equivalent to an absorbance of 0.82 units at 590 nm).

Example 2

The $2^{nd}$ exp. includes four litters; all pups (n=36) were randomly divided into two groups (Creon: 150 mg of capsule (lipase 10 000 USP, potease 37 500 USP, amylase 33 200 USP and water), the dose of Creon was 1.5 mg/g b.wt), then each group divided into subgroup pretreated one hour prior to enzyme feeding with anti-inflammatory drugs, Ibuprofen or Celecoxib (celecoxib; Pfizer, New York, N.Y., USA) the dose of drugs was 0.01 mg/g b.wt per day for both, diluted to give volume 0.01 mL/g b.wt. Thus six groups were obtained water/water, Ibupofen/water, Celecoxib/water, water/Creon, Ibuprofen/Creon and Celecoxib/Creon.

Results

Example 1 and 2

Effect of Enzymes on Gut Maturation

There were no significant effects detected from Creon on proximal parts nor any from Rovabio doses on intestinal weight as compared with the control group (Table 1). In spite of there being little change in the intestinal length, none of the enzymes gave significant values (Table 1).

Figures 2A, 2B:
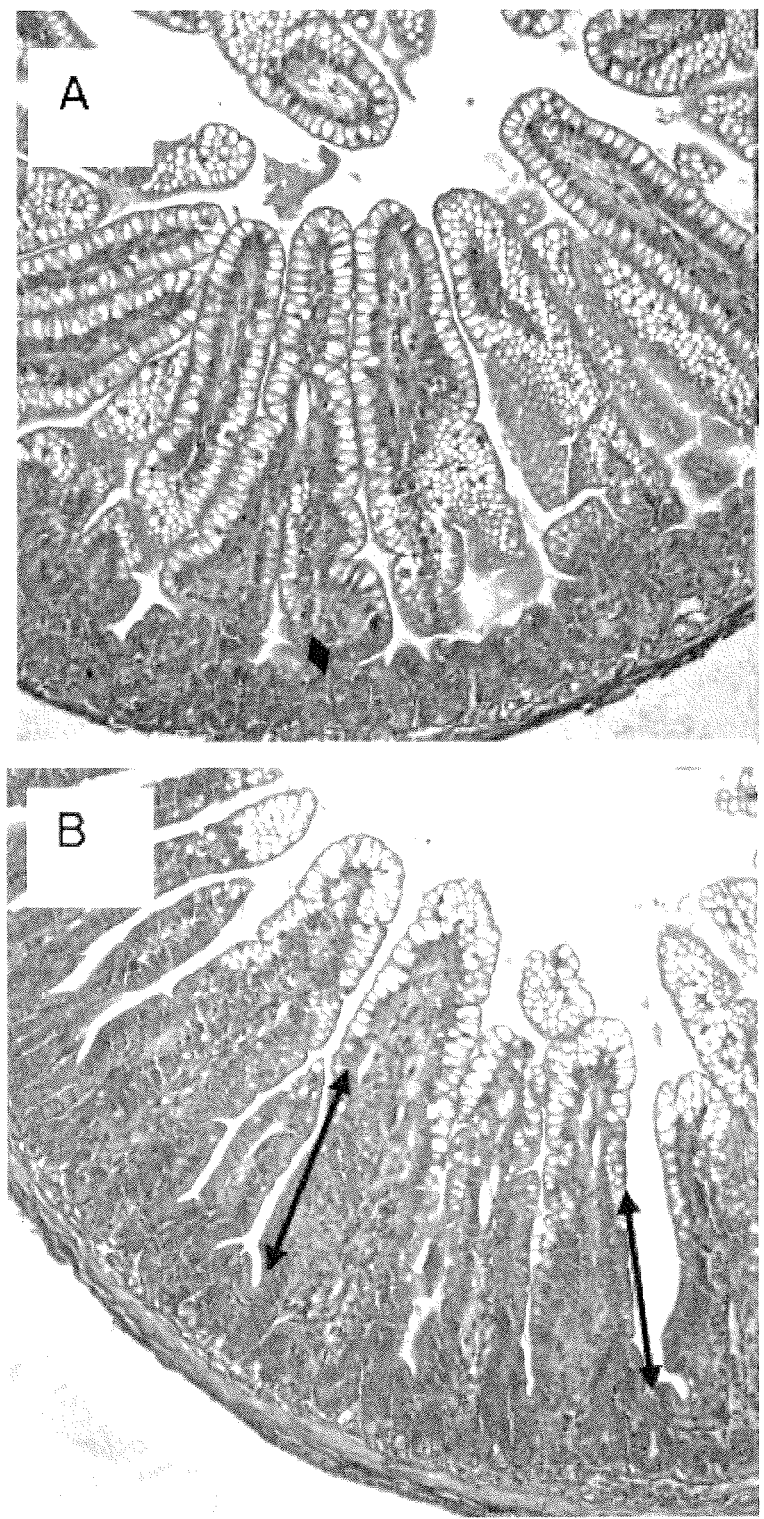
FIG. 2a-c shows the results of photomicrographs of the distal part of rats intestine following the high dose of B. Creon, and C. Robavio treatment, respectively as compared to A. water control.
Figure 2C:
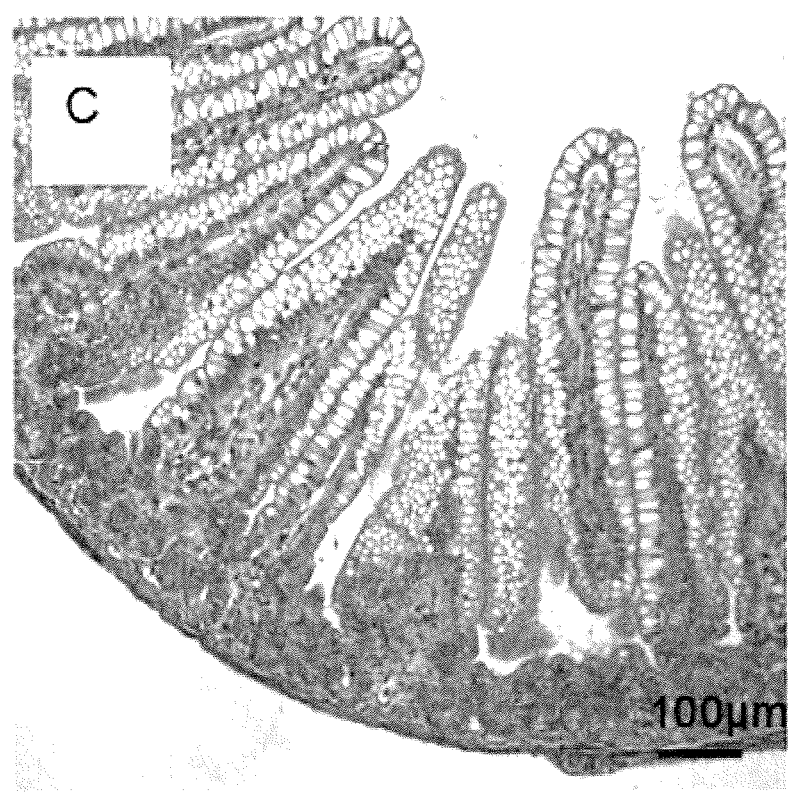

Effect on the Structure and Maturation of Enterocytes:

Both doses of Rovabio did not show any effect on class switching of enterocyte to mature phenotype as compared with that of the control group. In contrast, the enterocytes were highly affected and replaced by a new generation of adult phenotypes in response to high doses of Creon. The morphometric analyses as a percentage of mature entrocytes to whole villi height were 32% with Creon, as compared with control (Table 3 and FIG. 2a-c).

Effect on the Immune Cell in LP:

With both markers CD45 and CD25, no significant decrease and increase in response to Creon were observed as compared with control (Table 4).

Effect on Disaccharidases:

In both cases of Creon treated rat pups, a significant increase in maltase and sucrase activities could be seen in the distal SI homogenate, as compared with control, while no effect could be detected in lactase activity (Table 2).

Effect of Anti-Inflammatory Drugs on Creon-Induced Maturation

Effect on the Small Intestine (Weight and Length):

In Example 2 the effect of Creon on intestinal weight and length could not be cancelled in pups which were pre-treated with Ibuprofen and Celecoxib (Table 5).

Effect on the Structure of Villi:

The morphometric analysis of mature cells appeared to be unaffected in the presence of Ibuprofen, whereas there is slightly decrease in case of Celocoxib (Table 6).

Effect on Disaccharidases:

All disaccharidases activities have appeared to be unaffected in Ibuprofen pretreated pups, while it was slightly inhibited in Celocoxib pretreated pups especially with sucrase and maltase (Table 7).

TABLE 1

| | | Small intestine | | | | | |
|---|---|---|---|---|---|---|---|
| | | Length, cm/g bwt | | Proximal wt, mg/g bwt | | Distal wt, mg/g bwt | |
| Treatment | Dose | Mean | SD | Mean | SD | Mean | SD |
| Control (water) | — | 1.53 | 0.06 | 18.83 $^A$ | 1.05 | 17.49 $^A$ | 2.00 |
| Pancreatic enzymes of | low | 1.53 | 0.07 | 19.04 $^{AB}$ | 2.32 | 18.63 $^{AB}$ | 0.70 |
| animal origin | high | 1.50 | 0.10 | 21.08 $^B$ | 2.43 | 19.54 $^B$ | 0.80 |
| Control (water) | — | 1.50 | 0.09 | 17.51 $^A$ | 1.01 | 14.91 $^A$ | 0.71 |
| Pancreatic-like enzymes of | low | 1.63 | 0.12 | 15.49 $^{AB}$ | 1.15 | 16.39 $^{AB}$ | 1.21 |
| microbial origin | high | 1.55 | 0.11 | 19.53 $^B$ | 0.92 | 17.15 $^B$ | 1.44 |
| Control (water) | — | 1.55 | 0.12 | 17.55 | 1.08 | 15.51 | 0.51 |
| Nonpancreatic-like enzymes of | low | 1.52 | 0.04 | 17.78 | 1.73 | 17.24 | 1.51 |
| microbial origin | high | 1.58 | 0.04 | 17.71 | 0.75 | 16.95 | 1.60 |

Table 1 shows the results of a comparison between the effects of different doses of Creon (animal origin) and Rovabio (non-pancreatic like enzymes of microbial origin) as compared to their respective control on intestine length, and weight of proximal, and distal part. Values are means for all observations with standard deviation (n=3-7). Results considered to be significant if P<0.05. The different capital letters showed significant differences between compared groups.

TABLE 2

| | Disaccharidase specific activity, U/mg | | | | | |
|---|---|---|---|---|---|---|
| | Lactase | | Maltase | | Sucrase | |
| Treatment | Mean | SD | Mean | SD | Mean | SD |
| Control (water) | 99.86 | 19.96 | 81.03 $^A$ | 8.87 | 2.39 $^A$ | 0.92 |
| Pancreatic enzymes of animal origin | 79.82 | 3.48 | 152.99 $^B$ | 12.50 | 15.08 $^B$ | 1.22 |
| Pancreatic-like enzymes of microbial origin | 103.09 | 11.15 | 124.82 $^B$ | 21.32 | 8.95 $^B$ | 1.81 |

Table 2 shows the results of the effect of high doses of Creon® as compared to control on disaccharidase activity (lactase, maltase sucrase) in distal part of rat intestinal homogenates. Values are means for all observations with standard deviation (n=4-5). Results considered to be significant if P<0.05. The different capital letters showed significant differences between compared groups.

TABLE 3

| | Mature epithelium, % | |
|---|---|---|
| Treatment | Mean | SD |
| Control (water) | 8.92 $^A$ | 1.84 |
| Pancreatic enzymes of animal origin | 38.89 $^C$ | 5.54 |
| Pancreatic-like enzymes of microbial origin | 28.08 $^B$ | 7.42 |
| Nonpancreatic-like enzymes of microbial origin | 7.46 $^A$ | 3.25 |

Table 3 shows the effects of the high doses of Creon (animal origin), and Robavio (non-pancreatic like enzymes of microbial origin), on appearance of adult like enterocytes along the villi in the distal part of intestine. Results are expressed as means with SD (n=4-5). Results considered to be significant if P<0.05. The different capital letters showed significant differences between compared groups.

TABLE 4

| | Small intestine | | | |
|---|---|---|---|---|
| | CD45+, cells/mucosa | | CD25+, cells/mucosa | |
| Treatment | Mean | SD | Mean | SD |
| Control (water) | 91.14 | 24.61 | 89.01 | 45.08 |
| Pancreatic enzymes of animal origin | 64.24 | 33.13 | 53.71 | 48.50 |
| Control (water) | 30.96 | 20.84 | 29.88 | 20.86 |
| Pancreatic-like enzymes of microbial origin | 62.44 | 17.22 | 62.40 | 27.93 |

Table 4 shows a comparison between the effects of the high dose of Creon (enzymes of animal origin) on immune cells in the LP of distal small intestine. The figure shows numbers of leukocytes (CD45), and affector T-cell (CD25) after treated with the previous materials as compared with their respective control. Results are expressed as means with SD (n=3-8). No significant differences between groups are observed.

TABLE 5

| | | Small intestine | | | | | |
|---|---|---|---|---|---|---|---|
| | Drug pre- | Length, cm/g bwt | | Proximal wt, mg/g bwt | | Distal wt, mg/g bwt | |
| Treatment | treatment | Mean | SD | Mean | SD | Mean | SD |
| Control (water) | none (water) | 1.66 | 0.05 | 16.23 $^A$ | 0.88 | 14.39 $^A$ | 1.30 |
| | Ibuprofen | 1.60 | 0.15 | 16.24 $^A$ | 1.25 | 13.81 $^A$ | 1.08 |
| | Celexosib | 1.64 | 0.09 | 16.32 $^A$ | 1.55 | 14.45 $^A$ | 2.28 |
| Pancreatic enzymes | none (water) | 1.83 | 0.11 | 22.29 $^B$ | 1.16 | 17.79 $^B$ | 0.51 |
| of animal origin | Ibuprofen | 1.82 | 0.13 | 21.40 $^B$ | 3.42 | 18.02 $^B$ | 1.07 |
| | Celexosib | 1.80 | 0.10 | 20.93 $^B$ | 2.03 | 18.17 $^B$ | 1.88 |

Table 5 shows effect of Creon at dose 1.5 mg/g body weight on small intestine length and weight in presence of Ibuprofen and Celecoxib. Figure shows effect of NSAIDs in absence and presence the prescribed dose of Creon. Results presented as means with standard deviation (n=4-6). Results considered to be significant if P<0.05; the different capital letters showed significant differences between compared groups.

TABLE 6

| Treatment | Drug pre-treatment | Mature epithelium, % | |
|---|---|---|---|
| | | Mean | SD |
| Control (water) | none (water) | 10.62$^A$ | 0.88 |
| | Ibuprofen | 8.78$^A$ | 1.44 |
| | Celexosib | 7.98$^A$ | 1.82 |
| Pancreatic enzymes of animal origin | none (water) | 39.24$^B$ | 17.21 |
| | Ibuprofen | 40.29$^B$ | 18.31 |
| | Celexosib | 30.84$^B$ | 9.38 |

Table 6 illustrates the percentage of mature entrocytes along villi for each group of treatment. Values are expressed as means with standard deviations. Results considered to be significant if P<0.05; the different capital letters showed significant differences between compared groups.

TABLE 7

| Treatment | Drug pre-treatment | Disaccharidase specific activity, U/mg | | | | | |
|---|---|---|---|---|---|---|---|
| | | Lactase | | Maltase | | Sucrase | |
| | | Mean | SD | Mean | SD | Mean | SD |
| Control (water) | none (water) | 113.51 | 10.83 | 78.28$^A$ | 19.70 | 1.02$^A$ | 1.48 |
| | Ibuprofen | 114.17 | 11.76 | 82.75$^A$ | 13.72 | 1.12$^A$ | 1.41 |
| | Celexosib | 100.91 | 6.31 | 72.24$^A$ | 11.98 | 1.28$^A$ | 1.64 |
| Pancreatic enzymes of animal origin | none (water) | 108.04 | 17.93 | 222.27$^B$ | 22.09 | 21.89$^B$ | 9.92 |
| | Ibuprofen | 115.86 | 21.64 | 211.45$^B$ | 56.84 | 22.21$^B$ | 11.65 |
| | Celexosib | 105.41 | 14.63 | 190.22$^B$ | 36.75 | 18.09$^B$ | 6.94 |

Table 7 shows the disaccharidase activity in distal part of rat intestinal homogenates for each group as showed in the bottom of the columns. Values are expressed as means with standard deviation (n=4-5). Results considered to be significant if P<0.05; the different capital letters showed significant differences between compared groups.

Example 3-5

Material & Methods for Examples 3-5

All experiments were performed in young suckling rats by feeding them from 14 days of age via stomach tube for 3 continuous days (ones a day). One day after last treatment rats were euthanized and plasma and organs proceeded to study structural and functional changes of gastrointestinal system.
Animals The examples 3-5 were carried out on *Rattus norvegicus* (14 day old pups) from Sprague-Dawley strain (Mol: SPRD Han; Taconic M & B, Denmark). The dams were placed in the animal facility under standard environment (20±10, 50±10 RH %, 12:12 hr light-dark cycle) in individual polycarbonate cages with the bedding material inside it. They had free access to the rodent laboratory chow (RM1, SDS, Essex, England) and the bottled tap water placed over their cages. The cage of pregnant females was checked regularly to define the birth date as day 0. The litter size for each dam was restricted to 12 or 13 pups, to reduce variability. Pups were restricted to reach to the solid food by using 7 cm wall extensor over each cage. The pups were kept with their dam until dissection day (day 17). The protocol for this experiment was approved by the Lund University Ethical Review Committee for Animal Experiments and conducted according to the European Community regulation concerning the protection of experimental animals.
Feeding Procedure and Dissection All the experiments were done in split-litter model.
Source of Enzymes All enzymes used in experiments are commercially available and can be purchased from Sigma Aldrich:
1) α-Amylase from *Aspergillus oryzae*
2) Lipase from *B. cepacia*
3) Proteinase from *Aspergillus melleus*

Example 3

Set I

In this set suckling pups were divided into five groups; control (water) amylase 10 000 USP/rat/day, lipase 4 000 USP/rat/day, protease 15 000 USP/rat/day, and mixture of these enzyme with corresponding activities per rat and day.

This study was evaluating the effects of different pancreatic-like enzymes on the gut maturation and functioning and had 3 individual litters; n=12, n=10 and n=13, totally n=7 pups per each group. Each of the enzymes (Amylase, Protease and Lipase) (Sigma Aldrich) was available in the powder form and was resolved in distilled water prior to stomach feeding during days 14, 15 and 16. The volume of administered enzymes and distilled water (for control groups) was 0.01 ml/g BW. Each time, prior to the feeding procedure, the pups were weighed. At day 17, pups were starving for 2 hours prior to feeding with marker molecule solution containing BSA (1.25 mg/g BW) and BIgG (1.25 mg/g BW), administration volume 0.025 ml/g BW. Then 3 hours later, the pups were sedated with $CO_2$ and anaesthetized by subcutaneous injection with a mixture of ketamine (Ketalar®, Pfizer, New York, USA, NaCl and azaperone (Stresnil®, Janssen Pharmaceutica, Beerse, Belgium), 0.01 ml/g BW. After opening the abdomen of the rats, 1 ml of blood was collected from heart by using syringes containing protease inhibitor and EDTA (50 µl) as anticoagulant and was transferred into ice-chilled tubes. After this, the pancreas was immediately dissected and rinsed with cold 0.9% NaCl, weighted and stored at −70 C. The SI was removed and its length was measured then divided into two halves, proximal and distal. Each segment was flushed out with cold 0.9% NaCl to clean the lumen and was then weighed separately. About 2 cm from middle part of these segments was taken for histology and the rest of the intestine was frozen in −70 for disaccharidase analysis, Dahlqvist method (1984). The stomach was removed and its content was collected into the tube (for measuring its pH) and frozen. Then cecum was dissected out, opened, rinse and weighed as well as liver and lymphoid organs spleen and thymus were dissected and weighted. All samples taken for histology were immediately fixed in the Bouin's solution for 24 hours then were transferred into the 70% ethanol. The plasma were collected after centrifuging at 3,000 for 15 minutes at 4° C. and frozen at −20° C. for further studies.

Example 4

Set II

The second study was about comparing the effect of different doses of protease (15000 USP, 7500 USP, 3750 USP and 1850 USP) on the development of the GI tract with control. In this experiment 2 litters of pups were used (n=13 and n=12). Pups were divided into five groups to fed with different doses of protease; 15000 USP (n=3), P7500 USP (n=6), P 3750 USP (n=6), P 1875 USP (n=5) and water as a control (n=5). The feeding was during 3 continuous days, once a day. 24 hours after the last feeding, on day 17, similar dissection steps and analytical procedures as mentioned for the previous experiment were followed.

Example 5

Set III

In the last study, the health and the growth of the pups were monitored for 3 weeks. Pups where treated at age 14 day of life with the protease 15 000 USP/rat/day for 3 days once a day (on days 14, 15, and 16). This study performed using 3 litters (n=9, n=11 and n=10) where pups were divided into 2 groups; enzyme treated and control. After last feeding rat were further divided into subgroups: early weaning started on day 17 (n=8) and normal weaning started on day 21 (n=6). All animals were monitored via weighing for one week on a daily basis and then once a week for the next 2 weeks.

Intestinal Morphology

All samples collected for histology were fixed with Bouin's solution for 24 hours and then stored in 70% ethanol, dehydrated, embedded into the paraffin and then cut into sections with 5 μm thickness. The tissue sections were transferred onto the slides, rehydrated and stained with H&E according to the standard technique. After mounting under cover slips samples were examined using light microscopy to estimate ratio between total length of the villus and length of the adult type enterocytes using ImageJ program.

Intestinal Enzymology

The proximal samples of the SI were de-frozen and weighted and then homogenized with 9 parts of 0.9% NaCl (9 w/v). The homogenates (50 μl diluted samples) were incubated with the appropriate disaccharide (50 μl of 0.056M sucrose, maltose and lactose) for 1 hour at 37° C. After this, the liberated glucose was determined by adding glucose oxidase reagent (Sigma Chemicals), and incubated for 30 minutes. Then samples were transferred into the 96-well plate in triplication and the absorbance was measured at 450 nm. To measure the protein contents of the homogenates, Lowry method, was used, where BSA (Bovine Serum Albumin) was used as a standard. The results are presented as specific activity units per mg of protein (u/mg).

Plasma Concentration of Marker Molecules

The plasma level of marker molecules was quantified by using immunoassay rocket electrophoresis and SRI (single radial immunodiffusion) for plasma BSA and BIgG respectively.

Stomach PH

The contents of the stomach were de-frozen and then resolved with 1 ml of cold 0.9% NaCl. After resolving, they were centrifuged and the pH was measured in the supernatant using pH-meter.

Calculation and Statistic

All data are presented as mean±standard deviation (SD). Statistical comparisons between each group and control group were performed using the t-test. Results were considered as significant when $P<0.05$.

Results and Discussion for Examples 3-5:

Decreased intestinal permeability for macromolecule absorption, changes in disaccharidase activity from predominant lactase to maltase and sucrase as well as changes in structure of the small intestinal mucosa from the fetal type enterocytes to the adult types, demonstrated precociously induced maturation by protease enzyme. These effects on gut were found to be dose-dependent for protease.

Example 3

Effects of Individual Pancreatic-Like Enzymes, Amylase, Lipase, Protease and their Mixture on Gut Maturation Set I. Effects of Individual Enzymes with Pancreatic-Like Activity on Body and Organ Weights Table 8 shows the body weight of rats treated for 3 days with individual enzymes or their mixture and weights of the digestive and lymphoid organs. The results show that groups treated with protease and mixture had lower body weight compared to that in the other groups and control, may be due to diarrhoea observed after receiving the first dose. After one day of losing weight, they start to gain weight in a regular basis again. The result showed significant increase in organs along digestive tube: small intestine and cecum as well as accessory organ pancreas. Moreover both proximal and distal parts of SI had significantly higher weight, while the length of the SI was longer in comparison to other groups and control. In addition, in the pups treated with protease and mixture, the weight of the thymus was significantly lower compared to that in control showing developmental changes in immune system, while spleen weight was unchanged.

TABLE 8

Effects of pancreatic-like enzymes and distilled water (control) on suckling rats GI and lymphoid organs

| Group | Body weight (gr) | Pancreas (mg/g BW) | Stomach (mg/g BW) | pH | SI length (cm/g BW) | Proximal SI (mg/g BW) |
|---|---|---|---|---|---|---|
| Control (n = 7) | 36.1 ± 2.1 | 3.4 ± 0.3 | 6.8 ± 0.6 | 4.3 ± 0.2 | 1.4 ± 0.1 | 17.0 ± 2.3 |

TABLE 8-continued

Effects of pancreatic-like enzymes and distilled water (control) on suckling rats GI and lymphoid organs

| Group | | | | | | |
|---|---|---|---|---|---|---|
| Amylase (n = 7) | 37.2 ± 2.3 | 3.5 ± 0.4 | 6.8 ± 0.4 | 4.0 ± 0.2 | 1.5 ± 0.0 | 16.6 ± 1.9 |
| Protease (n = 7) | 33.6 ± 1.9* | 4.3 ± 0.4** | 7.2 ± 0.7 | 3.5 ± 0.3* | 1.7 ± 0.1** | 24.7 ± 3.5** |
| Lipase (n = 7) | 36.8 ± 2.2 | 3.7 ± 0.5 | 6.9 ± 0.8 | 4.0 ± 0.3 | 1.5 ± 0.1 | 17.5 ± 1.7 |
| Mixture (n = 7) | 33.6 ± 1.8* | 4.3 ± 0.4** | 7.3 ± 0.5 | 3.4 ± 0.4* | 1.7 ± 0.1* | 28.1 ± 2.3** |

| Group | Distal SI (mg/g BW) | Liver (mg/g BW) | Cecum (mg/g BW) | Thymus (mg/g BW) | Spleen (mg/g BW) |
|---|---|---|---|---|---|
| Control (n = 7) | 14.5 ± 0.6 | 33.5 ± 3.7 | 2.6 ± 0.5 | 4.9 ± 0.4 | 3.4 ± 0.3 |
| Amylase (n = 7) | 15.2 ± 2.3 | 33.7 ± 1.3 | 2.5 ± 0.3 | 5.1 ± 0.2 | 3.6 ± 0.7 |
| Protease (n = 7) | 17.8 ± 2.5** | 35.8 ± 2.5 | 4.0 ± 0.5** | 3.96 ± 0.4* | 3.4 ± 0.5 |
| Lipase (n = 7) | 15.2 ± 0.9* | 34.5 ± 1.8 | 2.4 ± 0.4 | 4.9 ± 0.8 | 3.5 ± 0.4 |
| Mixture (n = 7) | 17.6 ± 0.6** | 37.3 ± 2.8 | 4.5 ± 0.4** | 3.9 ± 0.9* | 3.3 ± 0.3 |

Figure 3:
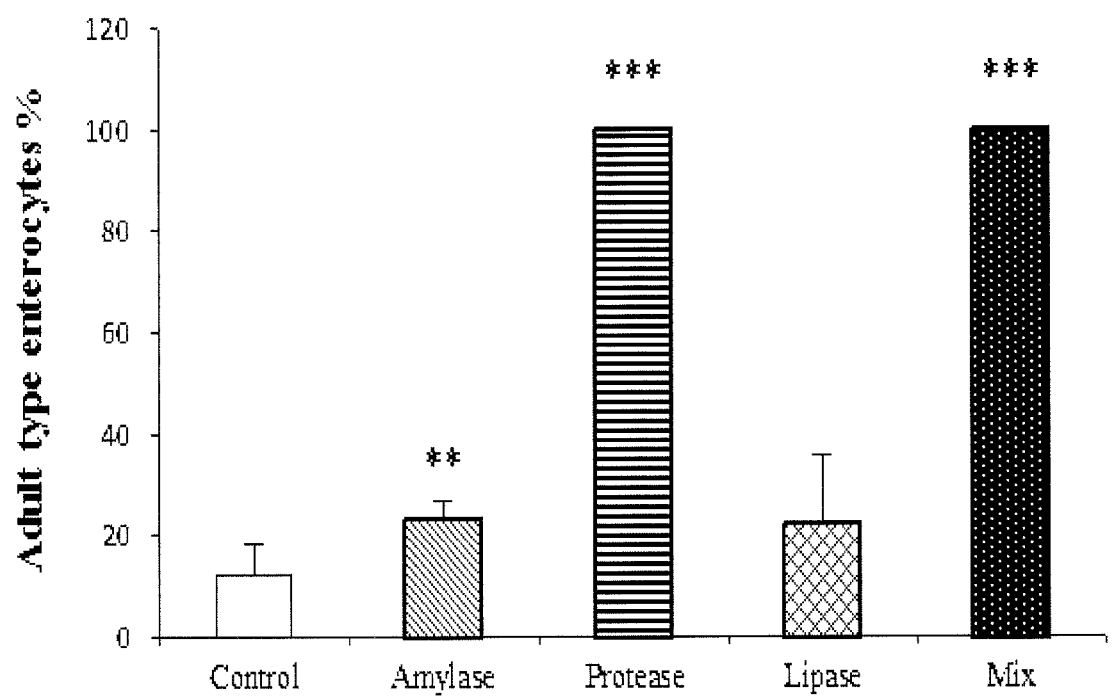
FIG. 3 shows the maturation degree of the epithelium in the distal part of rats' small intestine induced by different enzyme treatments. Results expressed as a mean±SD. Each treated group was compared to control using Student t-test. Significant results; P<0.05 (*), P<0.01 (), P<0.001 (*).
Figure 4:
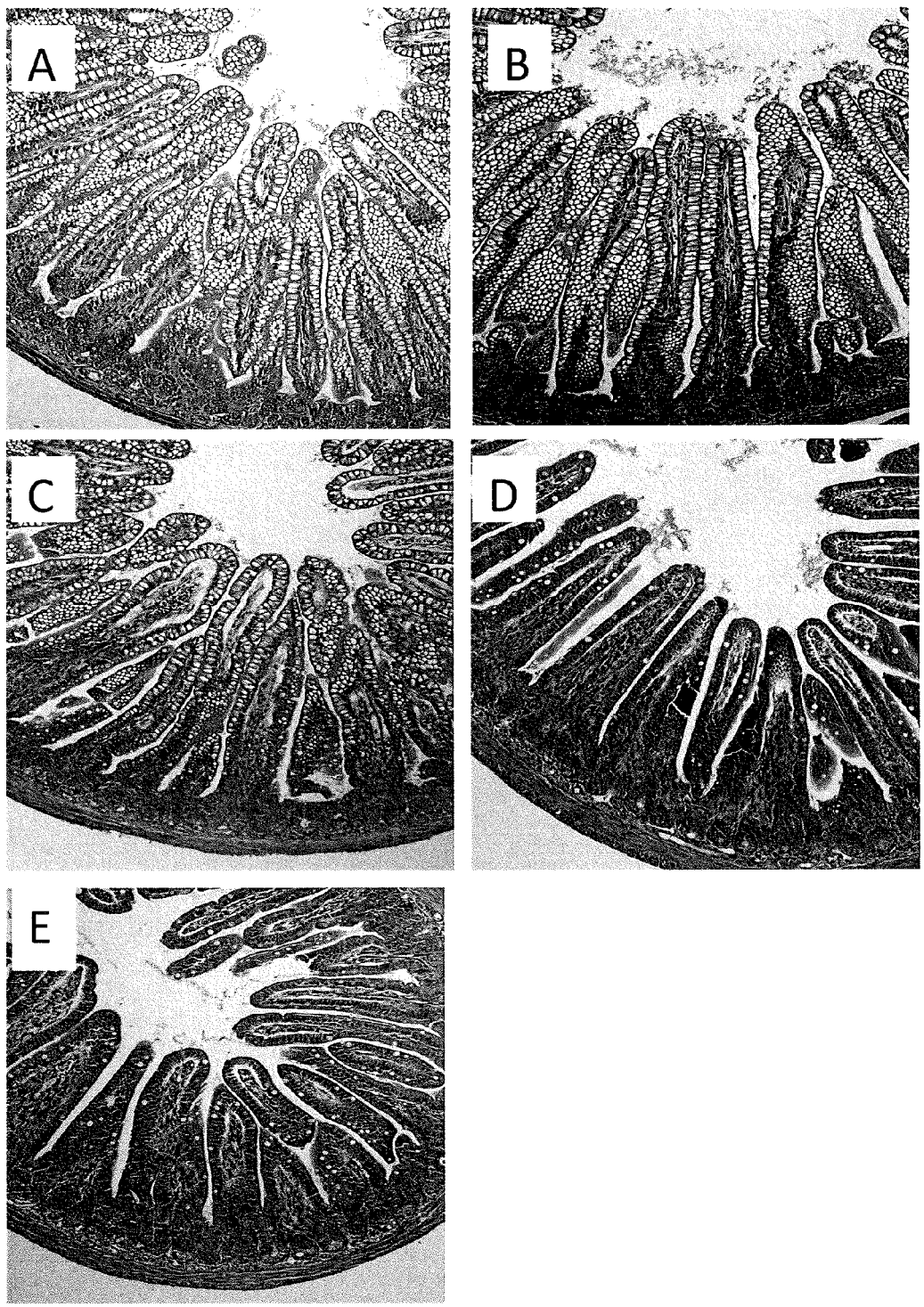
FIG. 4 shows photomicrograph of the H&E stained sections from the distal part of the rats' small intestine demonstrating the presence of the fetal-type enterocytes containing supranuclear vacuoles in control (A), lipase (B), and amylase (C) treated groups, while protease (D) and enzymes mixture (E) treated groups demonstrate mucosa with total replacement of enterocytes containing supra-nuclear vacuoles with adult-type epithelium. Original magnification ×10.

In Table 8 the weight of different gastrointestinal and lymphoid organs presented per gram body weight (g BW), expressed as mean ± SD. Each group were compared to control by Student' t-test. The significant differences are demonstrated with $P < 0.05$(*), $P < 0.01$(**).
SI, small intestine; BW, body weight Intestinal Morphology The slides prepared from the distal part of SI were analysed for the present of foetal and adult type enterocytes. In the control group, foetal-type epithelium with vacuolated enterocytes expanded along the whole villi (87.7%), where as in groups treated with amylase and lipase these cells limited to the middle and the tip of the villi (A=77%, L=77%) (FIG. 3). In pups treated with protease and mixture, all of the vacuolated enterocytes were replaced with adult type enterocytes (FIG. 4).

Disaccharidase Activity

Figures 5A, 5B:
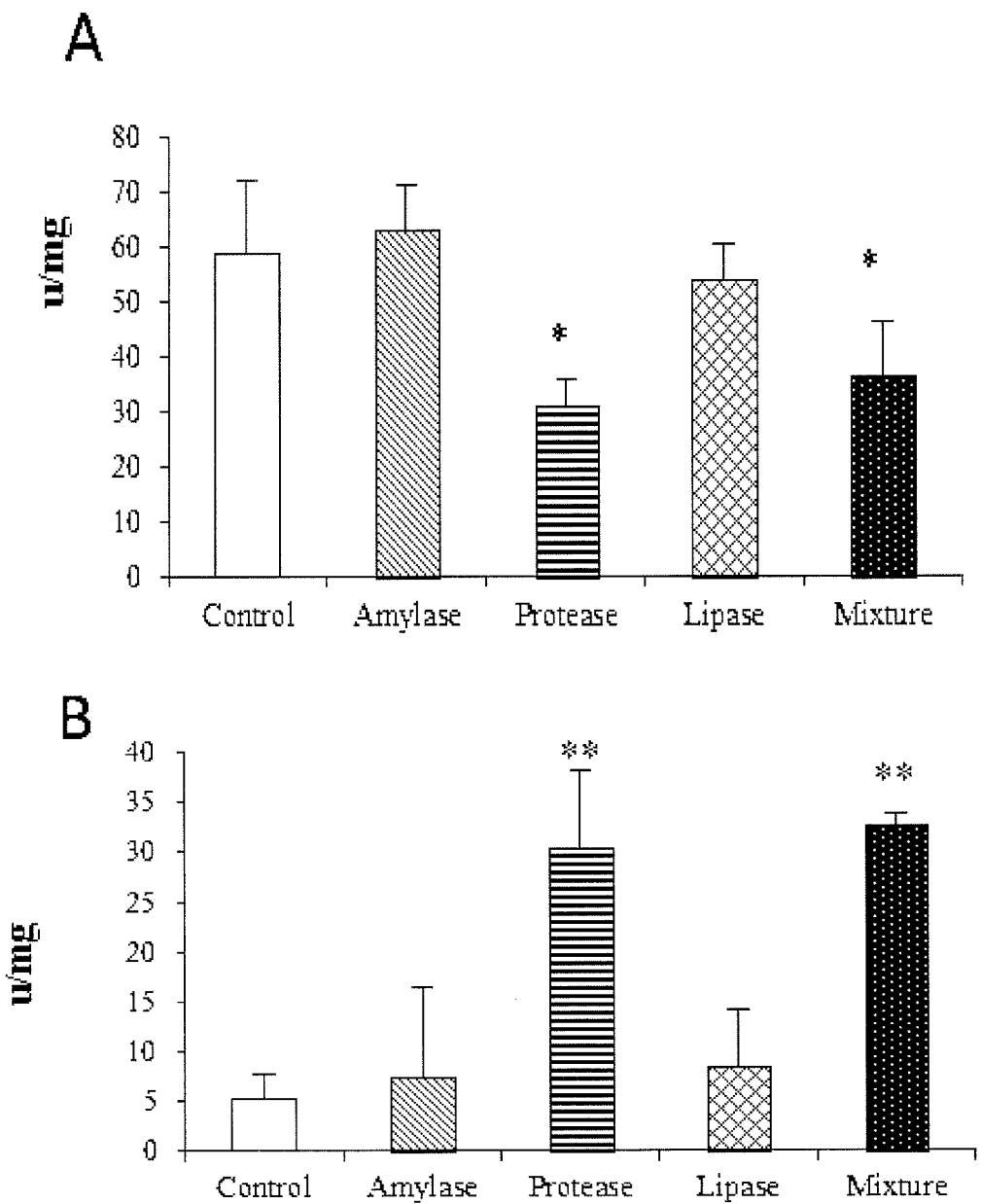
FIG. 5 shows changes in brush-border enzyme activities for lactase (A), sucrase (B) and maltase (C) in the proximal part of the small intestine after administration of individual enzymes (amylase, lipase and protease) or their mixture to 14 d old rat during 3 days. Results are expressed as mean±SD. Treated groups were compared to control using Student t-test. Significant differences; P<0.05 (*), P<0.01 (**)
Figure 5C:
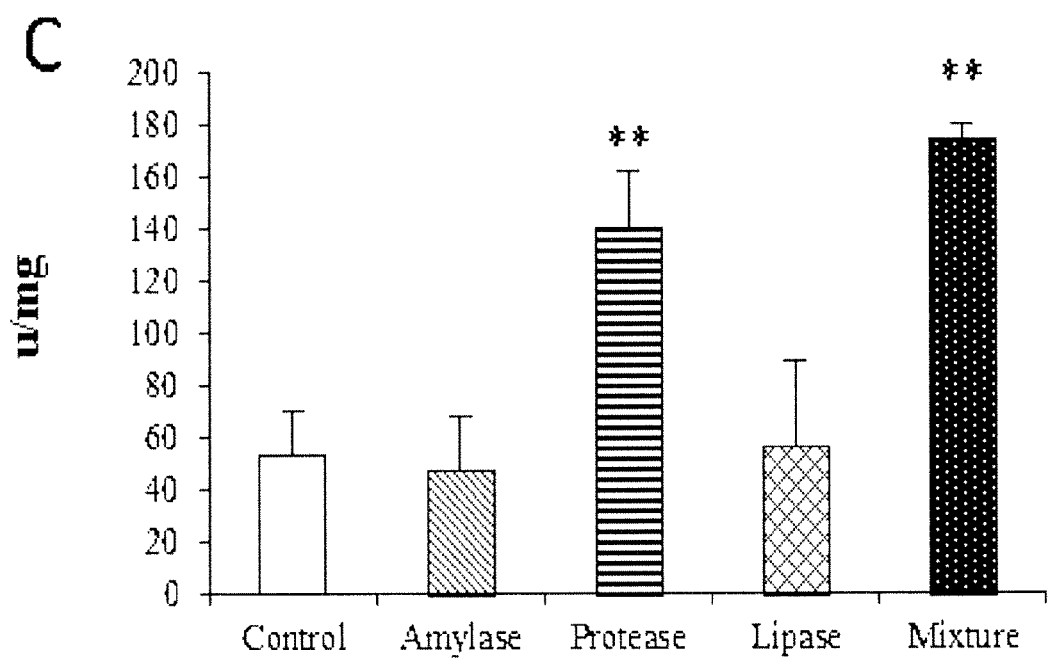

The activities of the brush-border disaccharidases, maltase, sucrase and lactase were analyzed in the proximal part of the small intestine (SI). In groups treated with protease and mixture, the activity of lactase decreased while maltase and sucrase activities were significantly increased. In contrast, lactase activity was higher in control, lipase and amylase groups while the sucrase and maltase activities stayed in a lower level (FIG. 5).

Effect on the pH

Stomach contents of the protease and mixture treated groups had significant lower pH compared to that in the control, amylase and lipase groups (Table 8).

Effects on Macromolecule Absorption

Figure 6:
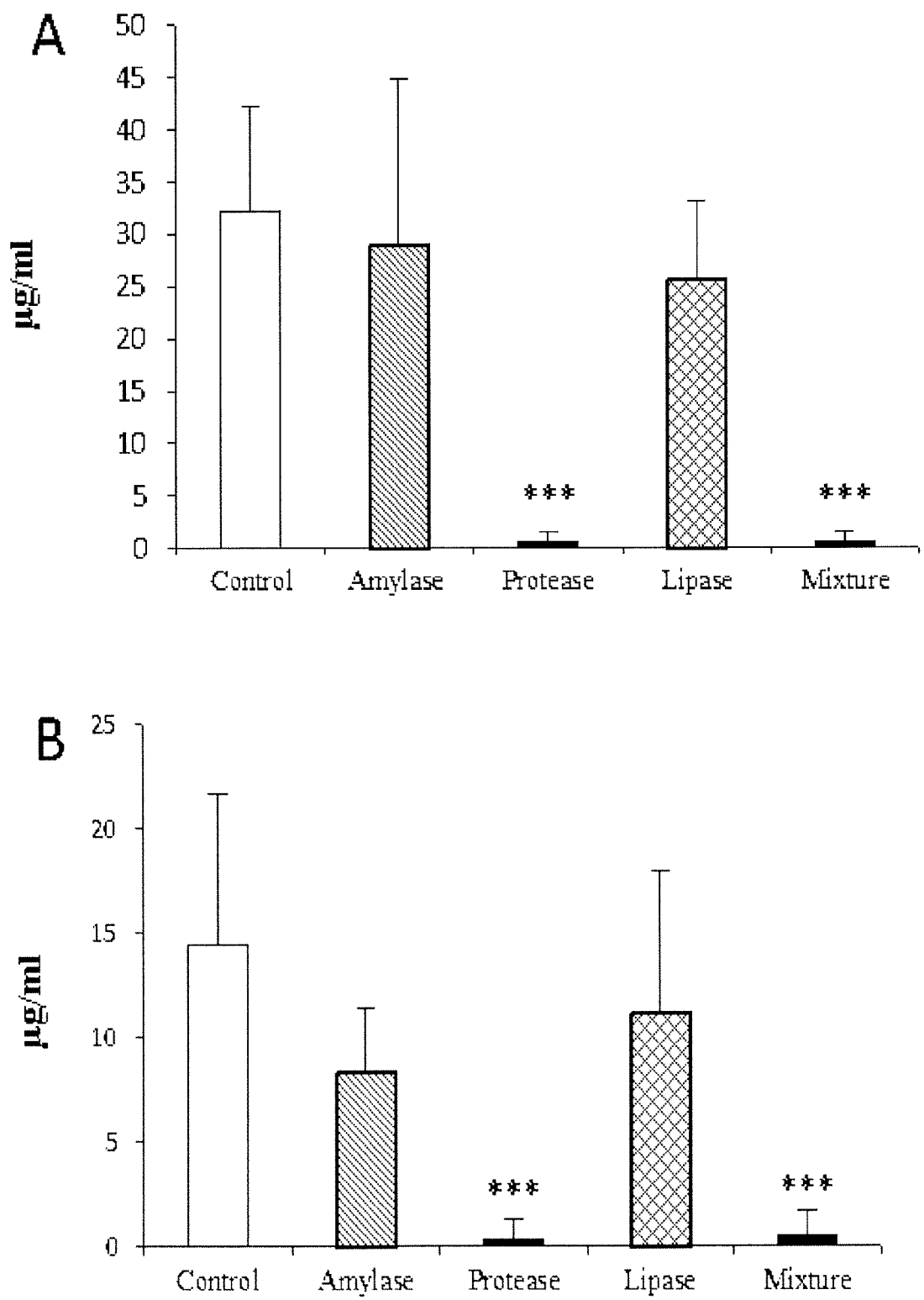
FIG. 6 shows the effect individual enzyme administration: amylase, protease, lipase and their mixture (administered to the 14 d old rats for 3 days), on the level of marker molecules absorption BIgG (A) and BSA (B) to the plasma in comparison to control. The results are given as mean±SD. Treated groups were compared to control using Student t-test. Significant results; P<0.001 (***).

The uptake of marker molecule both BSA and BIgG was significantly lower among the groups treated with protease and enzyme mixture, demonstrating decreasing of intestinal permeability (intestinal "closure"). In contrast, the intestinal macromolecular absorption capacity in control group and the pups treated with amylase and lipase remained in a higher level (FIG. 6).

Conclusion (Set I)

The results of this experiment evaluated that the administration of protease but not lipase to suckling rats induces morphological and functional development and maturation of the small intestine (SI), while amylase showed sign on maturation only in distal small intestine. Nevertheless, the results demonstrate that effect of protease in the most prominent for both gastrointestinal (GI) system growth and maturation, while lipase has effect only on distal intestinal growth and showed no other signs of maturation.

Example 4

Set II. Effects of Different Doses Enzymes with Pancreatic-Like Activity on Body and Organ Weights This study designed to compare the effects of different doses of protease on gut development to find the sufficient range of enzyme treatment. Table 9A demonstrates the weight of different organs, Table 9B showed the mean body weights of rats during treatment period (from 14 to 16 d of age and the day of dissection, 17 d of life) and FIG. 7. shows the rats body weight during treatment. The group treated with the highest dose of protease had signs of diarrhoea after receiving the first dose on day 14. The results of digestive organs demonstrate that rats treated with protease 15 000 USP and 7 500 USP had increased weight for GI organs and the length of the SI was longer in this group compared to that in control. Additionally, the thymus weight was significantly lower in the highest dose compare to control.

TABLE 9A

Effects of different doses of protease (15000 USP, 7500 USP, 3750 USP, 1875 USP) and distilled water (control) on suckling rats GI and lymphoid organs.

| Group | Pancreas (mg/g BW) | Stomach (mg/g BW) | pH | SI length (cm/g BW) | Proximal SI (mg/g BW) | Distal SI (mg/g BW) |
|---|---|---|---|---|---|---|
| Control (n = 5) | 3.2 ± 0.2 | 6.2 ± 0.2 | 4.4 ± 0.6 | 1.4 ± 0.1 | 15.7 ± 1.6 | 13.2 ± 1.8 |
| P (15000 USP) (n = 3) | 4.8 ± 0.2*** | 6.9 ± 0.7 | 3.4 ± 0.8* | 1.8 ± 0.1*** | 28.2 ± 1.7*** | 18.6 ± 1.0* |
| P (7500 USP) (n = 8) | 3.4 ± 0.4 | 6.3 ± 0.4 | 3.9 ± 0.7 | 1.8 ± 0.1** | 19.3 ± 2.0** | 15.4 ± 1.7 |
| P (3750 USP) (n = 8) | 3.2 ± 0.3 | 6.4 ± 0.3 | 4.1 ± 0.4 | 1.5 ± 0.1 | 17.6 ± 1.5 | 14.7 ± 1.1 |
| P (1875 USP) (n = 5) | 3.0 ± 0.4 | 6.1 ± 0.3 | 4.1 ± 0.2 | 1.5 ± 0.0 | 16.4 ± 0.8 | 13.3 ± 1.4 |

| Group | Liver (mg/g BW) | Thymus (mg/g BW) | Cecum (mg/g BW) | Spleen (mg/g BW) |
|---|---|---|---|---|
| Control (n = 5) | 32.5 ± 2.5 | 5.3 ± 0.5 | 2.3 ± 0.2 | 3.2 ± 0.6 |
| P (15000 USP) (n = 3) | 38.5 ± 2.4* | 3.0 ± 0.2*** | 4.2 ± 0.1*** | 3.0 ± 0.3 |
| P (7500 USP) (n = 8) | 33.0 ± 1.6 | 4.8 ± 0.6 | 3.0 ± 0.2*** | 3.1 ± 0.1 |
| P (3750 USP) (n = 8) | 32.8 ± 1.7 | 5.6 ± 0.8 | 2.8 ± 0.3 | 3.3 ± 0.5 |
| P (1875 USP) (n = 5) | 31.7 ± 1.1 | 5.6 ± 0.3 | 2.3 ± 0.2 | 3.3 ± 0.4 |

The weight of different gastrointestinal and lymphoid organs presented per gram body weight (g BW), expressed as mean ± SD. Each group were compared to control by Student' t-test. The significant differences are demonstrated with $P < 0.05$(*), $P < 0.01$(), and $P < 0.001$ (*).
SI, small intestine; P, protease; BW, body weight

TABLE 9B mean body weights during treatment period and (14-16 d of life) and day of dissection (17 d)

| | Bwt 1/Day 14 | Bwt2/Day 15 | Bwt3/Day 16 | Bwt4/Day 17 |
|---|---|---|---|---|
| Protease 15 000USP | 28.7 | 27.4* | 28.2* | 30.1* |
| Protease 7500USP | 28.9 | 30.6 | 32.2 | 33.6 |
| Protease 3750USP | 28.5 | 30.5 | 32.3 | 33.3 |
| Protease 1875USP | 28.2 | 31.7 | 32.9 | 34.8 |

Intestinal Morphology

The slides prepared from the distal part of SI were analysed for the maturation degree of mucosa by measuring the appearance of adult type enterocytes. In the control group, fetal-type epithelium with vacuolated enterocytes still expanded along the whole villi, while in groups treated with proteases P 7500 USP, 3750 USP and 1875 USP these cells limited to the middle and the tip of the villi, and in P 15000 USP group all of the vacuolated enterocytes disappeared by giving place to adult type enterocytes demonstrating dose-dependent effect of protease treatment on intestinal morphology (FIG. 8).

Effect on the pH

Stomach contents of the protease 15000 USP treated group had lower pH compared to that in the control, and groups treated with other doses (Table 9).

Conclusion (Set II)

The results of this experiment evaluated that the effects of protease on the gut maturation and development were dose dependent. Hence, range with activity between 15 000 USP and 7 500 USP must be deeply investigated to find the optimal effective dose.

Example 5

Effects of Individual Enzymes with Pancreatic-Like Activity on Body and Organ Weights In this set of experiment, after feeding pups with protease in dose 15 000 USP, their health and growth were monitored, in daily basis for the treatment days and one week after weaning, then every week for two more weeks. Some of rats after first treatment showed signs of diarrhea for highest dose of protease. Generally, the results demonstrated earlier observed decrease in growth after first treatment with highest dose of protease in comparison to control group (FIG. 9).

The early and normal weaning did not show difference in growth between enzyme and control groups, however after normal weaning (NW) the body weight for both control and enzymes groups were significantly higher compared to early weaned (EW) rats.

Conclusion (Set III)

All the pups were gaining weight regularly and had no systematic problem or growth disorder.

The early weaning showed no disadvantage for both groups, control and protease enzyme treated. However at second week after weaning, the body weight for both control and enzyme treated groups were lower compared to that in normally weaned groups.

General Conclusion Experiment 3-5

The results from this study have demonstrated that pancreatic-like enzymes of microbial origin might contribute in GI development after 3 days exposure. Furthermore, the protease has the most prominent effect on gut growth as well as structural and functional maturation of gut organs compared to other enzymes. However, amylase also had some effects on SI maturation seeing from change in the enterocyte replacement, while lipase had effect on small intestinal growth in the distal portion, respectively. Effects of enzymes on the gut maturation were concluded from alteration in the mucosal disaccharidase pattern (increased activity of sucrase and maltase and decreased lactase activity), gut "closure" (decreased intestinal permeability for macromolecules) and changes in mucosa morphology (the replacement of the supranuclear vacuole-containing enterocytes (fetal-type) with adult-type enterocytes).

Example 6

Effects of Individual Pancreatic-Like Enzymes, Amylase, Lipase, Protease and their Mixture on Exocrine Pancreatic Secretion The same rat model as in Experiments 3-5 was used.

The effect of microbial-derived enzymes with pancreatic activity: protease, lipase, amylase and their mixture on exocrine pancreatic secretion after 3 d of oral gavage to suckling 14 d old rats (see experiment 3-5 above). Treated groups were compared to control, *p<0.05

As seen in FIG. 10, the results demonstrated that protease is the most efficient enzyme for stimulation of the pancreatic function in young rat.

Example 7

Effect of Microbial Derived Amylase and Lipase on Growth of Rats

This study was done to consider the effect of separated enzymes on body growth. The experiment is completing study done earlier to investigate effects of protease on body growth and was performed in similar mode (see experiment 3-5 above).

Suckling pups were divided into 3 groups depending on the treatment; amylase, lipase and water (n=7 per group). The enzymes are available in the market in form of powders and were resolved in distilled water prior to stomach feeding during 14-16 d of age, ones a day. The administered dose for each single enzyme feeding was 4 000 USP for lipase/rat and 10 000 USP for amylase/rat. The control group received vehicle.

FIG. 11 shows the growth of young rats treated once a day at age 14-16 d of life with microbial-derived enzymes having lipase and amylase activities, n=7 per group.

The result demonstrates the clear effect of amylase to stimulate growth of young rats in comparison to lipase and control group.

Example 8

Study on Papain Vs Microbial-Derived Protease

The laboratory animals used in this experiment were *Rattus norvegicus* (14 day old pups) from Sprague-Dawley strain. The dams were placed in the animal facility under standard environment (20±10, 50±10 RH %, 12:12 hr light-dark cycle) in individual polycarbonate cages with the bedding material inside it, with access to the rodent laboratory chow and the bottled tap water placed over the cages. The pregnant rats were checked regularly to define the birth date as day 0. The litter size for each dam was limited to 12 or 13 pups, to reduce variability. Pups were restricted to reach to the solid food by using 7 cm wall extensor over each cage and were kept with their dam until dissection day (day 17).

Suckling pups were divided into 3 groups depending on the treatments; microbial protease as a positive control, water as negative control and enzyme from papaya fruit (papain) (in total; protease=7, papain=8, control=7). The enzymes are available in the market in form of powders and were resolved in distilled water prior to stomach feeding during 14-16 d of age. The administered dose for each enzyme was 10000 USP/animal. The volume of administered enzymes and water (for control groups) was 0.01 ml/g b.wt. Prior to the feeding procedure, the pups were weighed. At day 17, pups were starving for 2 hours prior to the feeding with marker molecule solution containing BSA, as a marker for unspecific absorption (1.25 mg/g b.wt) and BIgG for specific absorption (1.25 mg/g b.wt), in 0.025 ml/g b.wt. Three hours later, the pups were anaesthetized and organs were dissected out for analyses.

Effects of Fruit Papain on Body and Organ Weight

Results are shown in Table 10 below showing effects of fruit papain on body and organ weight in comparison to microbial protease. By analysing the results from organ weights, it was obvious that pups treated with papain had heavier pancreas, cecum, proximal and distal SI while protease-treated pups showed significant increased weight in cecum, proximal and distal part of SI. There was also an increased weight of distal part of SI among group treated with trypsin. This increased in weight can be explained by hyperplasia, increased rate of stem cells proliferation in the SI.

TABLE 10

Effects of fruit papain on body and organ weight.

| Treatment | Body weight (gr) | Pncrease (mg/g BW) | Stomach (mg/g BW) | SI length (cm/g BW) | Proxima SI (mg/g BW) | Distal SI (mg/g BW) |
|---|---|---|---|---|---|---|
| Control (n = 7) | 36.1 ± 4.38 | 3.39 ± 0.48 | 6.88 ± 0.85 | 1.55 ± 0.10 | 16.88 ± 0.88 | 14.5 ± 0.6 |
| Protease(n = 7) | 34.8 ± 3.31 | 3.87 ± 0.34 | 6.71 ± 0.41 | 1.59 ± 0.18 | 20.24 ± 2.37** | 15.2 ± 2.3** |
| Papain(n = 8) | 33.2 ± 5.00 | 4.07 ± 0.46* | 7.13 ± 0.45 | 1.72 ± 0.17 | 21.49 ± 1.57*** | 17.8 ± 2.5** |

| Treatment | Liver (mg/g BW) | Cecum (mg/g BW) | Thymus (mg/g BW) | Spleen (mg/g BW) |
|---|---|---|---|---|
| Control (n = 7) | 32.43 ± 1.2 | 2.617 ± 0.27 | 4.91 ± 0.60 | 3.14 ± 0.30 |
| Protease(n = 7) | 32.22 ± 1.37 | 2.89 ± 0.47** | 4.95 ± 0.93 | 3.18 ± 0.23 |
| Papain(n = 8) | 33.33 ± 1.52 | 3.42 ± 0.45*** | 4.65 ± 0.92 | 3.46 ± 0.44 |

The weight of different gastrointestinal and lymphoid organs presented per gram body weight (g BW), expressed as mean ± SD. Each group was compared with control by t-test. The significant differences were demonstrated with $P < 0.05(*)$, $P < 0.01()$, $P < 0.001(*)$.
SI, small intestine Effects of Proteases on Body Weight The effects of proteases on body weight of suckling rats during 14 to 17 days of age, n=7-8 per group is shown in FIG. 12, where control is circles, papain is squares, and protease triangles on respective line. The figure is demonstrating the growth of suckling pups during the experiment. There is no effect of protease or papain in dose 10 000 USP on body growth was observed. In FIG. 12 the effects of proteases on body weight of suckling rats during 14 to 17 days of age, n=7-8 per group is shown. The graph is demonstrating the growth of suckling pups during experiment. No effect of protease or papain in dose 10 000 USP on body growth was observed.

Effect on Intestinal Disaccharidase Activity

The activities of the brush-border enzymes lactase, maltase and sucrase were analyzed in the proximal part of the SI in groups treated with papain and protease. Results are expressed as mean±SD. *p<0.05 in FIG. 13, where 13A shows lactase, 13B maltase and FIG. 13C sucrase.

In protease and papain groups the activity of maltase and sucrase were significantly increased compared to control. These functional changes demonstrate intestinal functional maturation where predominant lactase activity is decreasing while maltase and sucrase activity significantly increases. Such changes usually occur during weaning period due to dietary changes from milk to solid diet, however the animals in this experiment were used during their suckling period, having only milk as a diet. Hence the direct effect of papain and protease on small intestine cells might be concluded.

Effect on Macromolecule Absorption

The specific uptake of macromolecules was significantly lower among the pups treated with papain and protease as showed for BIgG absorption demonstrating decreased unspecific absorption. Furthermore, BSA concentration in rat plasma was significantly decreased in group treated with papain. In contrast, the intestinal macromolecular absorptive capacity in control group and the pups treated with bromelain and trypsin remained in a higher level, as shown in FIG. 14. Decreased absorption of BIgG and BSA can be explained by disappearance of neonatal Fc receptor (FcRn) in intestinal villi and decreased amount of supranuclear vacuoles due to replacement of adult type enterocytes lacking this ability. In general, result demonstrated decreasing of small intestinal permeability after protease and papain treatment. In FIG. 14, the effect of microbial protease and fruit protease on the level of marker molecules absorption to the plasma, after feeding them with cocktail of BSA (14B) and BIg G (14A) on day 17, (at 3 hours before dissection) is shown. These data are given as mean±SD. Significant results; * p<0.05; ***p<0.001

Conclusion

The results demonstrates that fruit derived protease, here papain, can provoke precocious functional maturation of small intestine in young rats.

Experiment 9

Gut Maturation—Suckling Pig Model I

All piglets were kept with sow during experimental procedure. Piglets from 3 litters divided into 5 groups and treated with low 1 capsule and high dose 5 capsules per 15 ml of milk of Creon enzyme preparation (porcine origin: 150 mg of Creon capsule (lipase 10 000 USP, potease 37 500 USP, amylase 33 200 USP) and mixture of microbial derived enzymes having pancreatic-like activity 200 mg of powder mixture per 15 ml of milk as a low dose and 1000 mg of powder mixture in 15 of cow milk as a high dose (in activity per 100 mg of mixture powder (lipase 17 600 USP, protease 12 500 USP, amylase 1 875 USP); while control group received only vehicle (n=6 per group). The administration volume was 2 ml/kg b.wt. for all groups. Totally: control (n=12), porcine Creon (n=12: low dose of Creon (LC) n=6, high dose of Creon (HC) n=6), microbial enzymes mixture (n=24: low dose of mixture (LM) n=12: high dose of mixture (HM) n=12)

Piglets were treated via stomach tube twice a day (8-9 am and 5-6 pm) starting at age 7-8 d of life and for one week. At age 14-15 d of life (next day after last evening treatment) the half from each groups of piglets were fed with macromolecule marker cocktail (Bovine serum albumin (BSA) in concentration 125 mg/ml and sodium fluorescein (NaF) in concentration 2.5 mg/ml; the administration volume was 4 ml/kg b.wt) to study intestinal permeability in vivo. Blood was collected at 0, ½, 1, 2, and 4 hours after marker-cocktail feeding. Then studied piglets were euthanized and gut organs dissected out and proceed for analyses. The rest of piglets were followed up to the slaughter.

The effect of enzyme treatment with porcine Creon and microbial enzymes mixture on body growth is shown in FIG. 15, as control (open circles), mixture of microbial enzymes (black circles) and Creon (open squares), n=12-6 per group.

The effect on intestinal crypt proliferation is shown in FIG. 16. The crypt cell proliferation in the small intestine of suckling 14-15 d old piglets after 1 week gavage treatment (twice a day) with preparation of enzymes having pancreatic-like activities of porcine and microbial origin. In FIG. 16 Cont is control; LM is low dose mixture; HM is high dose mixture; LC is low dose Creon, HC is high dose Creon. Groups were compared to control, *p<0.05

The weight of small intestine of suckling 14-15 d old piglets after 1 week gavage treatment (twice a day) with preparation of enzymes having pancreatic-like activities of porcine and microbial origin is shown in FIG. 17. Cont is control; LM is low dose mixture; HM is high dose mixture; LC is low dose Creon, HC is high dose Creon. Result demonstrate tendency of small intestine to increase its weight in dose-respond manner.

Disaccharidase activities in the small intestine of suckling 14-15 d old piglets after 1 week gavage treatment (twice a day) with high dose preparation of enzymes having pancreatic-like activities of porcine and microbial origin is shown in FIG. 18, where A is lactase, B is maltase and C is sucrase. Groups were compared to control (n=3-5), *p<0.05

Experiment 10

Gut Maturation—Suckling Pig Model II

All piglets were kept with sow until the weaning day. Piglets from 5-6 litters divided into 2 groups and treated with microbial protease (Sigma) (enz group) or water (cont) (n=28 per group), total 56. The dose of enzymes was 60 mg/ml with activity 1000 USP per 1 mg, the administration volume was 4 ml/kg b.wt, the frequency of administration was every second day (ones a day). Treatment via gavage feeding was started at 8 d of age and was done 3 times, (i.e. 8, 10, 12 d of life).

48 h after last feeding 12 piglets (6 contr, 6 enz) were separated from sow and transported to Dept, euthanized and proceed for organs dissected: stomach, small intestine, cecum, pancreas and liver.

Separate piglets (6 enzyme treated and 6 control pigs) were fed with marker molecule solution (Bovine serum albumin (BSA) in concentration 125 mg/ml and sodium fluorescein (NaF) in concentration 2.5 mg/ml; the administration volume was 4 ml/kg b.wt) at age 14 d of life and 27 d of life (the weaning day). Blood was collected at 0, %, 1, 2, 4, 8, and 24 hours after marker-cocktail feeding.

Additionally, at weaning, 27 d of life, 12 piglets (6 cont and 6 enz) were separated from sow and transported to Dept, euthanized and proceed for organs dissected: stomach, small intestine, cecum, pancreas and liver. The rest was weaned according to standard procedure and followed to monitor their body weight up to the slaughter.

Effect of Microbial-Derived Protease on Bogy Weight Gain

FIG. 19 shows the effect of microbial derived proteases on body weight gain in % where striped bars show treated piglets and open bars show control.

Effects of Microbial Enzyme on Marker Molecules Absorption

FIG. 20 shows the effects of microbial enzyme on marker molecules absorption in vivo. The results demonstrate decreased intestinal permeability for both BSA (20A) and NaF (20B) molecules in protease treated piglets (n=8) in comparison to control (n=8). *p<0.05

Effect of Protease on Exocrine Pancreatic Function

The effect of protease on pancreatic function after 3 times administration, starting at 8 d of life and every other day, the results represent material taken at 48 h after last enzyme treatment (14 d) and at weaning time (27 d) is shown in FIG. 21. FIG. 21A shows pancreas weight and 21B trypsin like activity. Black bars are enzyme treated, open bars are control.

Conclusion

Results indicated stimulating effect of enzyme treatment on young pig gut.

Example 11

Long-Lasting Anti-Aging Dietary Effect on Old Monglian Gerbils

This example will show the long-lasting anti-aging dietary effect on old Monglian gerbils, specifically analyzing gastro intestinal tract (GIT) mucosa amorphology and function of pancreatic like enzymes (lipase, amylase and proteinase of microbal origin).

The morphological and biochemical changes in the gastrointestinal tract and general health after long dietary treatment by pancreatic like enzymes of microbial origin of old animals will be analysed. Particularly, it will be exploring of the brain-GIT function in the old gerbil after long-lasting dietary effect of Pancreatic like enzymes.

Description of the Research Started Apr. 2, 2011 and Lasting by the End September 2011

The experiment will a) investigate gastrointestinal tract after long-lasting dietary effect by pancreatic like enzymes to old gerbils, b) study the level of the dietary fat, protein, carbohydrate and mineral metabolities in the blood after long-lasting dietary effect by pancreatic like enzymes to old gerbils and c) study hormonal profile of aging animals.

Experimental Setup

Aging model of Mongolian gerbil (n=48, ca 24 month of age).
    Control group—(n=24) recessive standard diet
    Treatment group—(n=24) recessive standard diet+selected pancreatic like enzymes
        Dietary treatment with pancreatic like enzymes during 6 month—expecting prolong life
        Behavior test of studied animal during experiment—expecting improvement mobility
        Electron microscopy study of gerbil intestine—improved integrity of the intestine
        Immunohistohemical study of gerbil's gut mocosa—enhanced GALT function
        Morphological analyses: vili length—enhanced length; muscosa sickness—enhanced; crypt depth—enhanced; intestinal disschardises—enhanced; host pancreatic enzyme and gal production—enhanced
        Gut functional test: in vitro macromolecule absorption—minimized

The invention claimed is:

1. A method of treating a subject having an immature GI-tract, the method comprising:
    administering a mixture comprising about 25,000-500,000 USP/kg bodyweight per day of lipase, about 37,500-1,250,000 USP/kg bodyweight per day of protease, and about 58,100 to 2,490,000 USP/kg bodyweight per day of amylase to a subject in need thereof, analysing a biological sample collected from said subject for maturation of the GI-tract, wherein at least one of intestinal enterocyte morphology or intestinal enterocyte biomarkers is analysed to monitor said maturation.

2. The method of claim 1, wherein the immature GI-tract is in a newborn human.

3. The method of claim 1, wherein a change in at least one of intestinal enterocyte morphology, intestinal enterocyte biomarkers, and weight of the intestine is indicative of GI-tract maturation, wherein an increase of the weight of the intestine is indicative of maturation.

4. The method of claim 1, wherein the mixture of enzymes is administered orally.

5. A method of treating an immature GI-tract disorder in a subject in need thereof, wherein the immature GI-tract disorder is necrotizing enterocolitis and wherein the method comprises administering to the subject a mixture comprising about 25,000-500,000 USP/kg bodyweight per day of lipase, about 37,500-1,250,000 USP/kg bodyweight per day of protease, and about 58,100 to 2,490,000 USP/kg bodyweight per day of amylase to induce GI-tract maturation.

6. The method of claim 5, wherein the subject in the need thereof is an infant.

\* \* \* \* \*